(12) United States Patent
Matsuoka et al.

(10) Patent No.: US 7,915,050 B2
(45) Date of Patent: Mar. 29, 2011

(54) REGULATORY GENES FOR PLANT DIFFERENTIATION AND GROWTH, AND USE OF THE SAME

(75) Inventors: Makoto Matsuoka, Nagoya (JP); Hidemi Kitano, Nagoya (JP); Motoyuki Ashikari, Nagoya (JP); Miyako Ueguchi, Nagoya (JP); Isomaro Yamaguchi, Bunkyo-ku (JP); Masatoshi Nakajima, Bunkyo-ku (JP)

(73) Assignee: National University Corporation Nagoya University, Aichi (JP)

( * ) Notice: Subject to any disclaimer, the term of this patent is extended or adjusted under 35 U.S.C. 154(b) by 475 days.

(21) Appl. No.: 11/918,378

(22) PCT Filed: Mar. 28, 2006

(86) PCT No.: PCT/JP2006/306242
§ 371 (c)(1),
(2), (4) Date: Feb. 27, 2008

(87) PCT Pub. No.: WO2006/112238
PCT Pub. Date: Oct. 26, 2006

(65) Prior Publication Data
US 2009/0031441 A1    Jan. 29, 2009

(30) Foreign Application Priority Data

Apr. 14, 2005  (JP) ................................ 2005-116432

(51) Int. Cl.
*G01N 33/00* (2006.01)
*C07K 14/00* (2006.01)
(52) U.S. Cl. .......................................... 436/86; 530/350
(58) Field of Classification Search .................. None
See application file for complete search history.

(56) References Cited

U.S. PATENT DOCUMENTS
2004/0123343 A1    6/2004 La Rosa et al.

FOREIGN PATENT DOCUMENTS
WO    WO-2006/128921 A2    12/2006

OTHER PUBLICATIONS

EMBL AC AK074026, "Oryza sativa Japonica Group cDNA clone:J033079J03, full insert sequence." (Jul. 19, 2003).
EMBL AC AY136305, "Arabidopsis thaliana unknown protein (At3g05120) mRNA, complete cds." (Aug. 29, 2002).
Hartweck, Lynn M. et al., "Rice Gibberellin Insensitive DWARF1 Is a Gibberellin Receptor That Illuminates and Raises Questions about GA Signaling," *The Plant Cell*, vol. 18:278-282 (2006).
Swain, Stephen M. et al., "Tall tales from sly dwarves: novel functions of gibberellins in plant development," *Trends in Plant Science*, vol. 10(3):123-129 (2005).
Supplementary European Search Report for Application No. 06730190.3, dated Apr. 21, 2009.

Ashikari, Motoyuki et al., "Rice gibberellin-insensitive dwarf mutant gene *Dwarf 1* encodes the α-subunit of GTP-binding protein," *Proc. Natl. Acad. Sci. USA*, vol. 96:10284-10289 (1999).
European Union Chromosome 3 Arabidopsis Sequencing Consortium, The Institute for Genomic Research & Kazusa Dna Research Institute, "Sequence and analysis of chromosome 3 of the plant *Arabidopsis thaliana*," *Nature*, vol. 408:820-822 (2000).
GenBank Accession No. AL163816, Obermaier, B. et al., *Arabidopsis thaliana* Nov. 15, 2007.
GenBank Accession No. NM_111384, *Arabidopsis thaliana* Apr. 30, 2008.
Gomi, Kenji et al., "GID2, an F-box subunit of the SCF E3 complex, specifically interacts with phosphorylated protein and regulates the gibberellin-dependent degradation of SLR1 in rice," *The Plant Journal*, vol. 37:626-634 (2004).
Gubler, Frank et al., "Gibberellin Signaling in Barley Aleurone Cells. Control of SLN1 and GAMYB Expression," *Plant Physiology*, vol. 129:191-200 (2002).
Harberd, Nicholas P., "Relieving DELLA Restraint," *Science*, vol. 299:1853-1854 (2003).
Hironori, Ito et al., "Shokubutsu no katachi Zukuri Idenshi kara Mita Bunshi Mechanism IV. Saibo Bunko o Unagasu Signal Dentatsukei A. Shokubutsu Hormon no Yakuwari Gibberellin no Joho Dentatsu," *Protein, Nucleic Acid and Enzyme*, vol. 47(12):1676-1681 (2002).
Ikeda, Akira et al., "*slender* Rice, a C onstitutive Gibberellin Response Mutant, Is Caused by a Null Mutation of the SLR1 Gene, an Ortholog of the Height-Regulating Gene GAI/RGA/RHT/D8," *The Plant Cell*, vol. 13:999-1010 (2001).
Itoh, Hironori et al., "A role for the ubiquitin-26S-proteasome pathway in gibberellin signaling," *Trends in Plant Science*, vol. 8(10):492-497 (2003).
Itoh, Hironori et al., "The Gibberellin Signaling Pathway Is Regulated by the Appearance and Disappearance of SLENDER RICE1 in Nuclei," The Plant Cell, vol. 14:57-70 (2002).
Lovegrove, Alison et al., "Gibberellin-photoaffinity labelling of two polypeptides in plant plasma membranes," The Plant Journal, vol. 15(3):311-320 (1998).
MATDB—entry At3g05120 (2006).
MATDB—entry At3g63010 (2006).
MATDB—entry At5g27320 (2006).
Nakajima, Masatoshi et al., "Partial Purification and Characterization of a Gibberellin-Binding Protein from Seedlings of Azukia angularis," Biochemical and Biophysical Research Communications, vol. 241:782-786 (1997).
Peng, Jinrong et al., "The Arabidopsis GAI gene defines a signaling pathway that negatively regulates gibberellin responses," Genes & Development, vol. 11:3194-3205 (1997).

(Continued)

*Primary Examiner* — Nashaat T Nashed
(74) *Attorney, Agent, or Firm* — Nelson Mullins Riley & Scarborough LLP; Jeanne M. DiGiorgio, Esq.

(57) ABSTRACT

An objective of the present invention is to provide gibberellin-binding proteins, genes encoding such proteins, and applications therefor. The proteins of the present invention function as cytoplasmic receptors for gibberellin and mediate gibberellin response in plants. Plants overexpressing such genes exhibited gibberellin-hypersensitive phenotypes, such as increased plant height. In contrast, plants in which the genes were mutated exhibited gibberellin-insensitive phenotypes, and thus became dwarfed. Accordingly, plant differentiation and growth can be regulated by introducing the gibberellin-binding genes of the present invention or by suppressing the expression of same.

8 Claims, 12 Drawing Sheets

OTHER PUBLICATIONS

Sakamoto, Tomaoki et al., "An Overview of Gibberellin Metabolism Enzyme Genes and Their Related Mutants in Rice," Plant Physiology, vol. 134:1-12 (2004).

Sasaki, Akie et al., "Accumulation of Phosphorylated Repressor for Gibberellin Signaling in an F-box Mutant," Science, vol. 299:1896-1898 (2003).

Silverstone, Aron L. et al., "The Arabidopsis RGA Gene Encodes a Transcriptional Regulator Repressing the Gibberellin Signal Transduction Pathway," The Plant Cell, vol. 10:155-169 (1998).

Sponsel, Valerie M. et al., "Gibberellin Biosynthesis and Inactivation," Plant Hormones, Biosynthesis, Signal Transduction, Action!, Peter J. Davies, Ed., Chpt. B2, pp. 63-94 (2004).

Sun, Tai-ping, "Gibberellin Signal Transduction in Stem Elongation & Leaf Growth," Plant Hormones, Biosynthesis, Signal Transduction, Action!, Peter J. Davies, Ed., Chpt. D2, pp. 304-320 (2004).

Ueguchi-Tanaka, Miyako et al., "Gibberellin Insensitive DWARF1 encodes a soluble receptor for gibberellin," Nature, vol. 437:693-698 (2005).

International Search Report for Application No. PCT/JP2006/306242, dated May 30, 2006.

McGinnis, Karen M. et al., "The Arabidopsis *SLEEPY1* Gene Encodes a Putative F-Box Subunit of an SCF E3 Ubiquitin Ligase," *The Plant Cell*, vol. 15:1120-1130 (2003).

Sakamoto, Tomaoki et al., "An Overview of Gibberellin Metabolism Enzyme Genes and Their Related Mutants in Rice," *Plant Physiology*, vol. 134:1642-1653 (2004).

FIG. 2
a
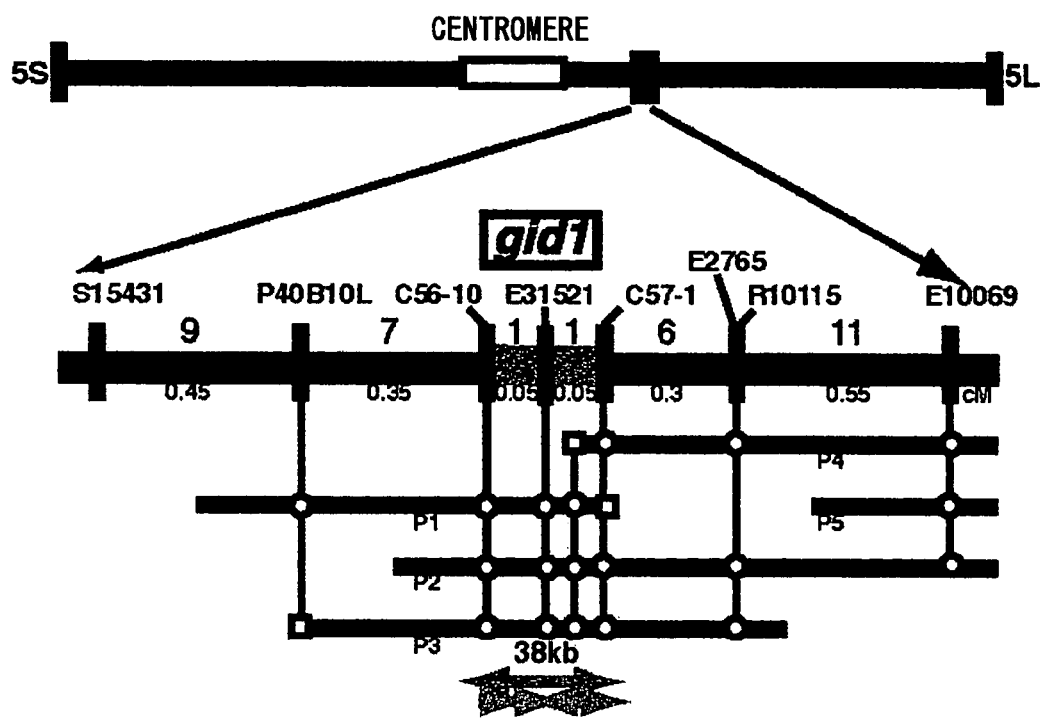
b
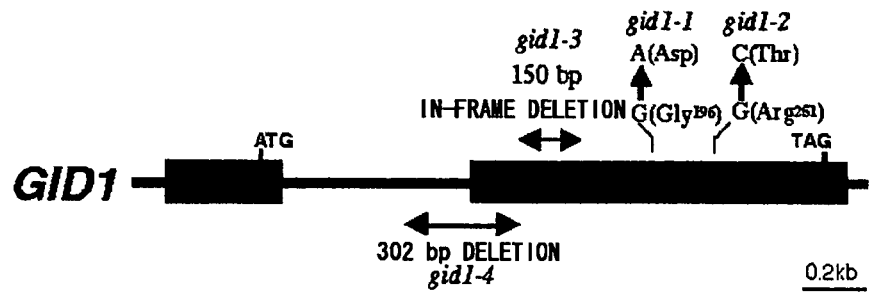

FIG. 3 a

MAGSDEVNRNECKTVVPLHTWVLISNFKLSTNILRRADGTFERDLGETLDRRVPANARPL

EGVSSFDHIIDQSVGLEVRITRAAAEGDAEEGAAAVTRPILEFLTDAPAAEPFPVIIFFH
　　　　　　　DELETION (gid1-3)

GGSFVHSSASSTIYDSLCRRFVKLSKGVVVSVNYRRAPEHRYPCAYDDGWTALKWVMSQP

FMKSGGDAQARVFLSGDSSGGNIAHHVAVRAADEGVKVCGNILLNAMFGGTERTESERRL
　　　　　　D(gid1-1)

DGKYFVTLQDRDWTWKAYLPEDADEDHPACNPFGPNGKRLGGLPPAKSLIIVSGLDLTCD
　　　T(gid1-2)

RQLAYADALREDGHHVKVVQCENATVGFTLLPNTVHTHEVMEEISDFLNANLYY
　　　　　　　　　　　　　　　　　　(SEQ ID NO: 2)

b

```
GID1 PILEFLTDAPAAEPFPVIIFFHGGSFVHSSASSTIYDSLCRRFVKLSKGVVVSVNYRRAP 158
HSL  DRVVRPDAANATAVVVYIHGGGFVLGSRTH--DGYMAVVAAAAGNRVISVDYRLAPEDQ- 122

GID1 EHRYPCAYDDGWTALKWVMSQPFMKSGGDAQARVFLSGDSSGGNIAHHVAVRAADEGVKV 217
HSL  EHPYPAALEDAVAAYRWLAEQAAAAELGI-DPS-RIAVAGDSAGGNLAAAVVLRARDEGPL 180

GID1 -CGNILLNAMFGGTERTESERRLDGKYFVTLQDR-DWTWKAYLPEDADEDHPACNPFGPN 276
HSL  PAAQVLISPLLDLSSSASSLPGVCRADLIDAAILP ADITRCAPLYDERASLRL--A 238

GID1 GKRLGGLPPAKSLIIVSGLDLTCDRQLAYADALREDGHHVKVVQCENATVGFTLLPNTVH 336
HSL  SDILSGRG--PTILQTAERDLLKDEAEAKLVAKAGVPAELRVYPGMIHGFIMFPEA 295

GID1 THEVMEEISDFLNANLYY 352 (POSITION 99 TO 351 IN SEQ ID NO: 2)
HSL  RSALR--QAAFIHRA 311 (SEQ ID NO: 3)
``` c

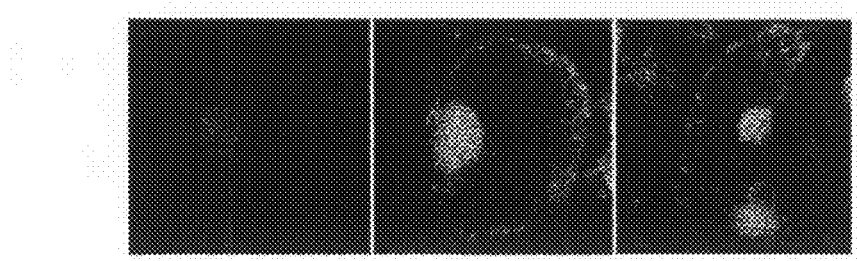

FIG. 5

```
OsGID1      ---MAGSDEVNRNECKTVVPLHTWVLISNFKLSYNILRRADGTFERDLGEYLDRRVPANARPLEGVSSFDHIIDQSVGLE
AtGID1a     ---MAAASDEVNLIESRTVVPLNTWVLISNFKVAYNILRRPDGTFNRHLAEYLDRKVTANANPVDGVFSFDVLIDRRINLL
AtGID1b     ---MAGGNEVNLNECKRIVPLNTWVLISNFKLAYKVLRRPDGSFNRDLAEFLDRKVPANSFPLDGVFSFDHVDS-TTNLL
AtGID1c     ---MAGSEEVNLIESKTVVPLNTWVLISNFKLAYNLLRRPDGTFNRHLAEFLDRKVPANANPVNGVFSFDVIIDRQTNLL
5g23530-D   ------MATDSQPNQKLTLPLKTRIALTVISTMTDNAQRPDGTINRRFLRLFDFRAPPNPKPVNIVSTSDFVVDQSRDLW
5g06570-E   ------------------MGSLGEEPQVAEDCMGLLQLLSNGTVLRSESIDLITQQIPFKN-NQTVLFKDSIYHKPNNLH
5g62180-F   -------------------MSEPSPIADPYAYLNIVNNPDGSITRDLSNFPCTAATPDPSPLNPAVSKDLPVNQLKSTW
3g48700-G   -------------------MDSEIAADYSPMLIIYKSGRIER---LVGETTVPPSSNPQNGVVSKDVVYSPDNNLS
1g47480-H   -------------------MESTKKQVSLELLPWLVVHTDGTVER---LAGTEVCPPGLDPITGVFSKDIIIEPKTGLS
5g16080-I   MATISFSHNHQSSDNRRGGSHHHRHGPVVEEIEGLIKVFNDGCVER---PPIVPIVSPTIHPSSKATAFDIKLSNDT--W
1g68620-J   MGGTKLTHVTTTNPN-----NSNIHGPVVDEVEGLIKVYKDGHVER---SQLLPCVDPSLPLELGVTCSDVVIDKLTNVW

OsGID1      VRIYRAAAEGDAEEGAAAVTRPILEFLTDAPAAEPFPVIIFFHGGSFVHSSASSTIYDSLCRRFVKLSKGVVVSVNYRRA
AtGID1a     SRVYRPAYADQEQPPSILDLEKPVDG-------DIVPVILFFHGGSFAHSSANSAIYDTLCRRLVGLCKCVVVSVNYRRA
AtGID1b     TRIYQPASLLHQTRHGTLELTKPLSTT------EIVPVLIFFHGGSFTHSSANSAIYDTFCRRLVTICGVVVSVDYRRS
AtGID1c     SRVYRPADAG--TSPSITDLQNPVDG-------EIVPVIVFFHGGSFAHSSANSAIYDTLCRRLVGLCGAVVSVNYRRA
5g23530-D   FRLYTPHVSGD----------------------KIPVVVFFHGGGFAFLSPNAYPYDNVCRRFARKLPAYVISVNYRLA
5g06570-E   LRLYKPISASNRT--------------------ALPVVVFFHGGGFCFGSRSWPHFHNFCLTLASSLNALVVSPDYRLA
5g62180-F   LRLYLPSSAVNEGNVS-----------------SQKLPIVVYYHGGGFILCSVDMQLFHDFCSEVARDLNAIVVSPSYRLA
3g48700-G   LRIYLPEKAATAETE------------------ASVKLPLLVYFHGGGFLVETAFSPTYHTFLTAAVSASDCVAVSVDYRRA
1g47480-H   ARIYRPFSIQPGQ--------------------KIPLMLYFHGGAFLISSTSFPSYHTSLNKIVNQANVIAVSVNYRLA
5g16080-I   TRVYIPDAAAASP--------------------SVTLPLLVYFHGGGFCVGSAAWSCYHDFLTSLAVKARCVIVSVNYRLA
1g68620-J   ARLYVPMTTTKSS--------------------VSKLPLIVYFHGGGFCVGSASWLCYHEFLARLSARSRCLVMSVNYRLA

OsGID1      PEHRYPCAYDDGWTALKWVMSQ--------PFMRSGGDAQARVFLSGDSSGGNIAHHVAVRAADEG--------VKVCGN
AtGID1a     PENPYPCAYDDGWIALNWVNSR--------SWLKSKKDSKVHIFLAGDSSGGNIAHNVALRAGESG--------IDVLGN
AtGID1b     PEHRYPCAYDDGWNALNWVKSR--------VWLQSGKDSNVYVYLAGDSSGGNIAHNVAVRATNEG--------VKVLGN
AtGID1c     PENRYPCAYDDGWAVLKWVNSS--------SWLRSKKDSKVRIFLAGDSSGGNIVHNVAVRAVESR--------IDVLGN
5g23530-D   PEHRYPAQYDDGFDALKYIEEN-------HGSILPANADLSRCFFAGDSAGGNIAHNVAIRICREPRS--SFTAVKLIGL
5g06570-E   PEHRLPAAFEDAEAVLTWLWDQAVSDGVNHWFEDGTDVDFDRVFVVGDSSGGNIAHQLAVRFGSGS---IELTPVRVRGY
5g62180-F   PEHRLPAAYDDGVEALDWIKTS-------DDEWIKSHADFSNVFLMGTSAGGNLAYNVGLRSVDSVS---DLSPLQIRGL
3g48700-G   PEHPIPTSYDD-SWTALKWVFSHIAGSG-SEDWLNKHADFSKVFLAGDSAGANITHHMTMKAAKDKLSPESLNESGISGI
1g47480-H   PEHPLPTAYED-SWTALKNIQ-----AI-NEPWINDYADLDSLFLVGDSAGANISHHLAFRAKQSDQ------TLKIKGI
5g16080-I   PEHRLPAAYDDGVNVVSWLVKQQISTGG-GYPSWLSKCNLSNVFLAGDSAGANIAYQVAVRIMASGK---YANTLHLKGI
1g68620-J   PENPLPAAYEDGVNAILWLNKARNDN------LWAKQCDFGRIFLAGDSAGGNIAQQVAARLASP-----EDLALKIEGT

OsGID1      ILLNAMFGGTERTESERRLDGKYFVTLQ--DRDWYWKAYLPEDADRDHPACNPFGPNGRRLGGLPFAKSLIIVSGLDLTC
AtGID1a     ILLHPMFGGNERTESEKSLDGKYFVTVR--DRDWYWKAFLPEGEDREHPACNPFSPRGKSLEGVSFPKSLVVVAGLDLIR
AtGID1b     ILLHPMFGGQERTQSEKTLDGKYFVTIQ--DRDWYWRAYLPEGEDRDHPACNPFGPRGQSLKGVNFPKSLVVVAGLDLVQ
AtGID1c     ILLNPMFGGTERTESEKRLDGKYFVTVR--DRDWYWRAFLPEGEDREHPACSPFGPRSKSLEGLSFPKSLVVVAGLDLIQ
5g23530-D   ISIQPFFGGEERTEAEKQLVGAPLVSPD--RTDWCWKAM---GLNRDHEAVNVGGPNAVDISGLDYPETMVVVAGFDPLK
5g06570-E   VLMGPFFGGEERTNSENGPSEALLSLDL---LDKFWRLSLPNGATRDHHMANPFGPTSPTLESISLEPMLVIVGGSELLR
5g62180-F   ILHHPFFGGEERSESEIRLMNDQVCPPIV--TDVMWNDLSLPVGVDRDHEYSNPTVGDGSEKLEKIGRLRWKVMMIGGEDD
3g48700-G   ILVHPYFWSKTPVDDKETTDVAIRTWIESVWTLASPNSKDGSDDPFINVVQSESVDLSG-LGCGKVLVMVAEKDALVRQG
1g47480-H   GMIHPYFWGTQPIG-AEIKDEARKQMVDGWWEFVCPSEK-GSDDPWINPFADGSPDLGG-LGCERVMITVAEKDILNERG
5g16080-I   ILIHPFFGGESRTSSEKQQHHTKSSALTLSASDAYWRLALPRGASRDHPWCNPLMSSAG-AKLPTTMVFMAEFDILKERN
1g68620-J   ILIQPFFYSGEERTESERRVGNDKTAVLTLASSDAWWRMSLPRGANREHPYCKPVKMIIKSSTVTRTLVCVAEMDLLMDSN

OsGID1      DRQLAYADALREDG-HHVKVVVQCENATVGFYLLPNT----VHYHEVMEEISDFLNANLYY---------- (SEQ ID NO:2)
AtGID1a     DWQLAYAEGLKKAG-QEVKLMHLEKATVGFYLLPNN----NHFHNVMDEISAFVNAEC------------- (SEQ ID NO:5)
AtGID1b     DWQLAYVDGLKKTG-LEVNLLYLKQATIGFYFLPNN----DHFHCLMEELNKFVHSIEDSQSKSSPVLLTP (SEQ ID NO:7)
AtGID1c     DWQLKYAEGLKKAG-QEVKLLYLEQATIGFYLLPNN----NHFHTVMDEIAAFVNAECQ----------- (SEQ ID NO:9)
5g23530-D   DWQRSYYEWLKLCG-KKATLIEYPNMFHAFYIFPELP----EAGQLIMRIKDFVDERVASLSA-------- (SEQ ID NO:10)
5g06570-E   DRAKEYAYKLKKMGGKRVDYIEFENKEHGFYSNYPSS----EAAEQVLRIIGDFMNNLS------------ (SEQ ID NO:11)
5g62180-F   PMIDLQKDVAKLMKKKGCVEVVEHYTGGHVHGAEIRDP----SKRKTLFLSIKNFIFSVL---------- (SEQ ID NO:12)
3g48700-G   WGYWEKLGKSRWNG-EVLDVVETKGEGHVFHLRDPN---SEKAHELVHRFAGFIKGDK------------ (SEQ ID NO:13)
1g47480-H   KMYYERLVKSEWKG--KVEIMETKEKDHVFHIFEPD---CDEAMEMVRCLALFINQVEA----------- (SEQ ID NO:14)
5g16080-I   ---LEMCKVMRSHG-KRVEGIVHGGVGHAFHILDNSSVSRDRIHDMMCRLHNFIHPS------------- (SEQ ID NO:15)
1g68620-J   ---MEMCDGNE----DVIKRVLHKGVGHAFHILGKSQLAHTTTLEMLCQIDAFIHHYDPLN--------- (SEQ ID NO:16)
```

FIG. 12
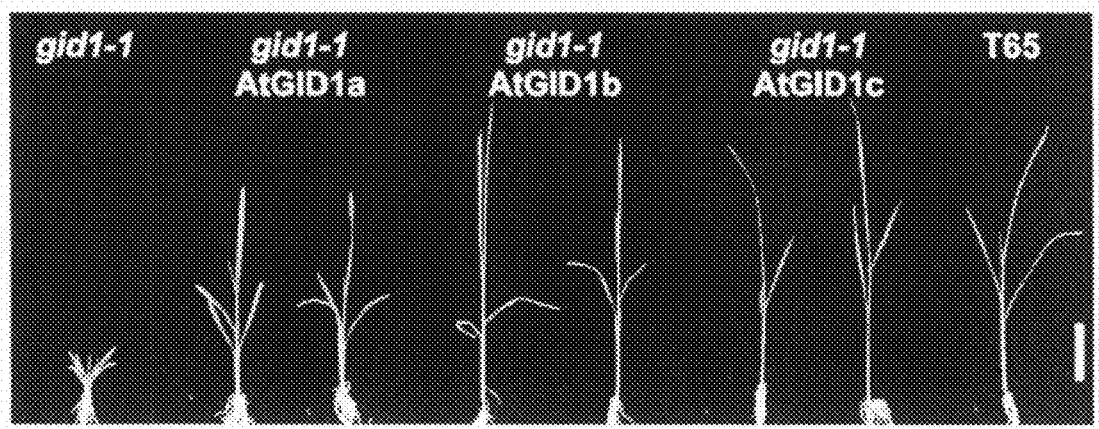
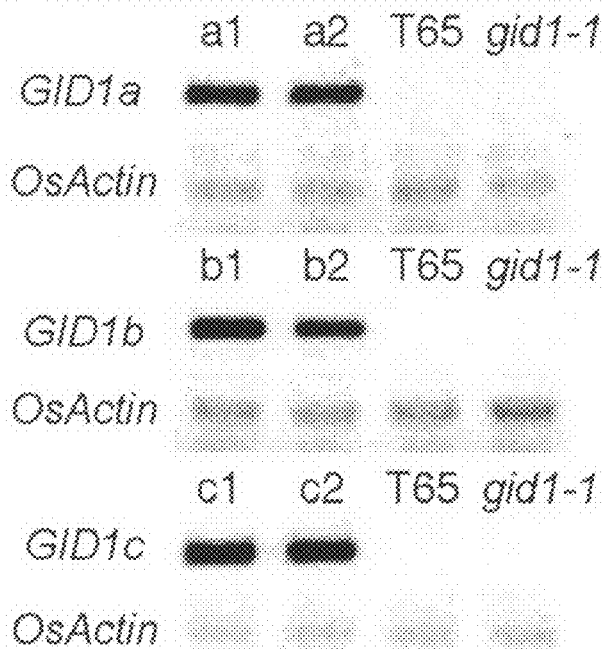
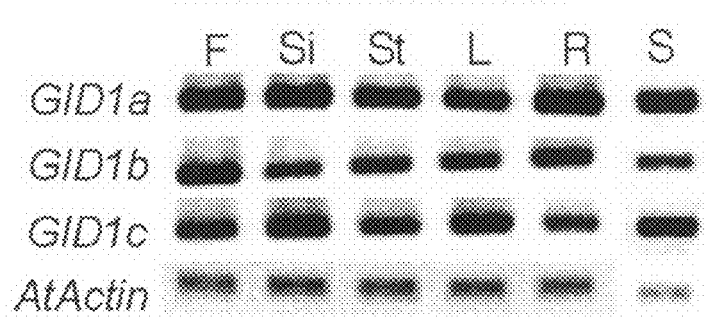

SEQUENCE LISTING

```
<160> NUMBER OF SEQ ID NOS: 26

<210> SEQ ID NO 1
<211> LENGTH: 1062
<212> TYPE: DNA
<213> ORGANISM: Oryza sativa
<220> FEATURE:
<221> NAME/KEY: CDS
<222> LOCATION: (1)..(1062)

<400> SEQUENCE: 1 atg gcc ggc agc gac gag gtc aac cgc aac gag tgc aag acg gtg gtg        48
Met Ala Gly Ser Asp Glu Val Asn Arg Asn Glu Cys Lys Thr Val Val
1               5                   10                  15 ccg ctc cac aca tgg gtg ctc atc tcc aac ttc aag ctg tcg tac aac        96
Pro Leu His Thr Trp Val Leu Ile Ser Asn Phe Lys Leu Ser Tyr Asn
                20                  25                  30 att ctg cgg cgg gcg gac ggg acg ttc gag cgg gac ctc ggg gag tac       144
Ile Leu Arg Arg Ala Asp Gly Thr Phe Glu Arg Asp Leu Gly Glu Tyr
            35                  40                  45 ctg gac agg agg gtg ccg gcg aac gcg cgg ccg ctg gag ggg gtg tcg       192
Leu Asp Arg Arg Val Pro Ala Asn Ala Arg Pro Leu Glu Gly Val Ser
        50                  55                  60 tcg ttc gac cac atc atc gac cag tcg gtg ggg ctg gag gtg cgc atc       240
Ser Phe Asp His Ile Ile Asp Gln Ser Val Gly Leu Glu Val Arg Ile
65                  70                  75                  80 tac cgg gcg gcg gcg gag ggt gac gcg gag gag ggg gcg gcg gcg gtg       288
Tyr Arg Ala Ala Ala Glu Gly Asp Ala Glu Glu Gly Ala Ala Ala Val
                85                  90                  95 acg cgg ccc atc ctt gag ttc ctg acg gac gcg cca gcg gcg gag ccg       336
Thr Arg Pro Ile Leu Glu Phe Leu Thr Asp Ala Pro Ala Ala Glu Pro
                100                 105                 110 ttc ccg gtg atc ata ttc ttc cac ggc ggc agc ttc gtg cac tcg tcg       384
Phe Pro Val Ile Ile Phe Phe His Gly Gly Ser Phe Val His Ser Ser
            115                 120                 125 gcc agc tcg acc atc tac gac agt ctg tgc cgc cgg ttc gtg aag ctg       432
Ala Ser Ser Thr Ile Tyr Asp Ser Leu Cys Arg Arg Phe Val Lys Leu
        130                 135                 140 agc aag ggc gtc gtg gtg tcc gtc aac tac cgg cgc gcg ccg gag cac       480
Ser Lys Gly Val Val Val Ser Val Asn Tyr Arg Arg Ala Pro Glu His
145                 150                 155                 160 cgc tac ccg tgc gcg tac gac gac ggg tgg acc gcg ctc aag tgg gtc       528
Arg Tyr Pro Cys Ala Tyr Asp Asp Gly Trp Thr Ala Leu Lys Trp Val
                165                 170                 175 atg tcg cag ccg ttc atg cgc agc ggc ggc gac gcg cag gcc cgc gtg       576
Met Ser Gln Pro Phe Met Arg Ser Gly Gly Asp Ala Gln Ala Arg Val
                180                 185                 190 ttc ctc tcc ggc gac agc tcc ggc ggc aac atc gcc cac cac gtc gcc       624
Phe Leu Ser Gly Asp Ser Ser Gly Gly Asn Ile Ala His His Val Ala
            195                 200                 205 gtc cgc gcc gcc gac gag ggc gtc aag gtc tgc ggc aac atc ctg ctc       672
Val Arg Ala Ala Asp Glu Gly Val Lys Val Cys Gly Asn Ile Leu Leu
        210                 215                 220 aac gcc atg ttc ggc ggc acc gag cgc acg gag tcg gag cgg cgg ctc       720
Asn Ala Met Phe Gly Gly Thr Glu Arg Thr Glu Ser Glu Arg Arg Leu
225                 230                 235                 240
```

| | | | | | | | | | | | | | | | |
|---|---|---|---|---|---|---|---|---|---|---|---|---|---|---|---|
| gac | ggc | aag | tac | ttc | gtg | acg | ctc | cag | gac | agg | gac | tgg | tac | tgg | aag | 768
| Asp | Gly | Lys | Tyr | Phe | Val | Thr | Leu | Gln | Asp | Arg | Asp | Trp | Tyr | Trp | Lys |
| | | | 245 | | | | | 250 | | | | | 255 | | | gcg tac ctg ccg gag gac gcc gac cgg gac cat ccg gcg tgc aac ccg 816
Ala Tyr Leu Pro Glu Asp Ala Asp Arg Asp His Pro Ala Cys Asn Pro
     260                 265                 270 ttc ggc ccg aac ggc cgg cgg ctc ggg ggc ctc ccc ttc gcc aag agc 864
Phe Gly Pro Asn Gly Arg Arg Leu Gly Gly Leu Pro Phe Ala Lys Ser
         275                 280                 285 ctc atc atc gtg tcg ggc ctg gac ctc acc tgc gac cgg cag ctc gcc 912
Leu Ile Ile Val Ser Gly Leu Asp Leu Thr Cys Asp Arg Gln Leu Ala
 290                 295                 300 tac gcc gac gcc ctc cgg gag gac ggc cac cac gtc aag gtt gtc caa 960
Tyr Ala Asp Ala Leu Arg Glu Asp Gly His His Val Lys Val Val Gln
305                 310                 315                 320 tgc gag aac gcc acg gtg ggg ttc tac ctg ttg ccc aac acc gtc cac 1008
Cys Glu Asn Ala Thr Val Gly Phe Tyr Leu Leu Pro Asn Thr Val His
             325                 330                 335 tac cac gag gtc atg gag gag atc tcc gac ttc ctc aac gct aac ctc 1056
Tyr His Glu Val Met Glu Glu Ile Ser Asp Phe Leu Asn Ala Asn Leu
             340                 345                 350 tac tac 1062
Tyr Tyr

<210> SEQ ID NO 2
<211> LENGTH: 354
<212> TYPE: PRT
<213> ORGANISM: Oryza sativa

<400> SEQUENCE: 2

Met Ala Gly Ser Asp Glu Val Asn Arg Asn Glu Cys Lys Thr Val Val
1               5                   10                  15

Pro Leu His Thr Trp Val Leu Ile Ser Asn Phe Lys Leu Ser Tyr Asn
            20                  25                  30

Ile Leu Arg Arg Ala Asp Gly Thr Phe Glu Arg Asp Leu Gly Glu Tyr
        35                  40                  45

Leu Asp Arg Arg Val Pro Ala Asn Ala Arg Pro Leu Glu Gly Val Ser
    50                  55                  60

Ser Phe Asp His Ile Ile Asp Gln Ser Val Gly Leu Glu Val Arg Ile
65                  70                  75                  80

Tyr Arg Ala Ala Ala Glu Gly Asp Ala Glu Glu Gly Ala Ala Ala Val
                85                  90                  95

Thr Arg Pro Ile Leu Glu Phe Leu Thr Asp Ala Pro Ala Ala Glu Pro
            100                 105                 110

Phe Pro Val Ile Ile Phe Phe His Gly Gly Ser Phe Val His Ser Ser
        115                 120                 125

Ala Ser Ser Thr Ile Tyr Asp Ser Leu Cys Arg Arg Phe Val Lys Leu
    130                 135                 140

Ser Lys Gly Val Val Ser Val Asn Tyr Arg Arg Ala Pro Glu His
145                 150                 155                 160

Arg Tyr Pro Cys Ala Tyr Asp Asp Gly Trp Thr Ala Leu Lys Trp Val
                165                 170                 175

Met Ser Gln Pro Phe Met Arg Ser Gly Gly Asp Ala Gln Ala Arg Val
            180                 185                 190

Phe Leu Ser Gly Asp Ser Ser Gly Gly Asn Ile Ala His His Val Ala
        195                 200                 205

Val Arg Ala Ala Asp Glu Gly Val Lys Val Cys Gly Asn Ile Leu Leu
    210                 215                 220

-continued

Asn Ala Met Phe Gly Gly Thr Glu Arg Thr Glu Ser Glu Arg Arg Leu
225                 230                 235                 240

Asp Gly Lys Tyr Phe Val Thr Leu Gln Asp Arg Asp Trp Tyr Trp Lys
            245                 250                 255

Ala Tyr Leu Pro Glu Asp Ala Asp Arg Asp His Pro Ala Cys Asn Pro
        260                 265                 270

Phe Gly Pro Asn Gly Arg Arg Leu Gly Gly Leu Pro Phe Ala Lys Ser
    275                 280                 285

Leu Ile Ile Val Ser Gly Leu Asp Leu Thr Cys Asp Arg Gln Leu Ala
290                 295                 300

Tyr Ala Asp Ala Leu Arg Glu Asp Gly His His Val Lys Val Val Gln
305                 310                 315                 320

Cys Glu Asn Ala Thr Val Gly Phe Tyr Leu Leu Pro Asn Thr Val His
                325                 330                 335

Tyr His Glu Val Met Glu Glu Ile Ser Asp Phe Leu Asn Ala Asn Leu
            340                 345                 350

Tyr Tyr

<210> SEQ ID NO 3
<211> LENGTH: 245
<212> TYPE: PRT
<213> ORGANISM: Artificial
<220> FEATURE:
<223> OTHER INFORMATION: Consensus sequence of hormone sensitive
      lipases (HSLs)

<400> SEQUENCE: 3

Pro Val Arg Val Tyr Arg Pro Asp Arg Lys Ala Ala Thr Ala Pro
1               5                   10                  15

Val Val Leu Tyr Leu His Gly Gly Tyr Val Leu Gly Ser Leu Arg
            20                  25                  30

Thr His Asp Ala Leu Val Ala Arg Leu Ala Ala Ala Gly Ala Val
        35                  40                  45

Val Val Ser Val Asp Tyr Arg Leu Ala Glu His Pro Phe Pro Ala Ala
50                  55                  60

Leu Glu Asp Ala Tyr Ala Ala Tyr Arg Trp Leu Arg Ala Asn Ala Ala
65                  70                  75                  80

Glu Leu Gly Ile Asp Pro Ser Arg Ile Ala Val Ala Gly Asp Ser Ala
                85                  90                  95

Gly Gly His Leu Ala Leu Ala Leu Ala Leu Ala Ala Arg Asp Arg Gly
            100                 105                 110

Leu Pro Leu Pro Ala Ala Gln Val Leu Ile Ser Pro Leu Leu Asp Leu
        115                 120                 125

Thr Ser Ser Ala Ala Ser Leu Pro Gly Tyr Gly Glu Ala Asp Leu Leu
130                 135                 140

Asp Ala Ala Ala Ile Leu Ala Trp Phe Ala Asp Leu Tyr Leu Gly Ala
145                 150                 155                 160

Ala Pro Asp Arg Glu Asp Pro Glu Ala Ser Pro Leu Ala Ser Asp Asp
                165                 170                 175

Leu Ser Gly Leu Pro Pro Thr Leu Ile Gln Thr Ala Glu Phe Asp Pro
            180                 185                 190

Leu Arg Asp Glu Gly Glu Ala Tyr Ala Glu Arg Leu Arg Ala Ala Gly
        195                 200                 205

Val Pro Val Glu Leu Arg Val Tyr Pro Gly Met Ile His Gly Phe Asp
210                 215                 220

Leu Leu Thr Phe Pro Glu Ala Arg Ser Ala Leu Arg Gln Ile Ala Ala
225                 230                 235                 240

Phe Leu Arg Ala Ala
            245

<210> SEQ ID NO 4
<211> LENGTH: 1035
<212> TYPE: DNA
<213> ORGANISM: Arabidopsis thaliana
<220> FEATURE:
<221> NAME/KEY: CDS
<222> LOCATION: (1)..(1035)

<400> SEQUENCE: 4

```
atg gct gcg agc gat gaa gtt aat ctt att gag agc aga aca gtg gtt      48
Met Ala Ala Ser Asp Glu Val Asn Leu Ile Glu Ser Arg Thr Val Val
1               5                   10                  15 cct ctc aat aca tgg gtt tta ata tcc aac ttc aaa gta gcc tac aat      96
Pro Leu Asn Thr Trp Val Leu Ile Ser Asn Phe Lys Val Ala Tyr Asn
            20                  25                  30 atc ctt cgt cgc cct gat gga acc ttt aac cga cac tta gct gag tat     144
Ile Leu Arg Arg Pro Asp Gly Thr Phe Asn Arg His Leu Ala Glu Tyr
        35                  40                  45 cta gac cgt aaa gtc act gca aac gcc aat ccg gtt gat ggg gtt ttc     192
Leu Asp Arg Lys Val Thr Ala Asn Ala Asn Pro Val Asp Gly Val Phe
    50                  55                  60 tcg ttc gat gtc ttg att gat cgc agg atc aat ctt cta agc aga gtc     240
Ser Phe Asp Val Leu Ile Asp Arg Arg Ile Asn Leu Leu Ser Arg Val
65                  70                  75                  80 tat aga cca gct tat gca gat caa gag caa cct cct agt att tta gat     288
Tyr Arg Pro Ala Tyr Ala Asp Gln Glu Gln Pro Pro Ser Ile Leu Asp
                85                  90                  95 ctc gag aag cct gtt gat ggc gac att gtc cct gtt ata ttg ttc ttc     336
Leu Glu Lys Pro Val Asp Gly Asp Ile Val Pro Val Ile Leu Phe Phe
            100                 105                 110 cat gga ggt agc ttt gct cat tct tct gca aac agt gcc atc tac gat     384
His Gly Gly Ser Phe Ala His Ser Ser Ala Asn Ser Ala Ile Tyr Asp
        115                 120                 125 act ctt tgt cgc agg ctt gtt ggt ttg tgc aag tgt gtt gtt gtc tct     432
Thr Leu Cys Arg Arg Leu Val Gly Leu Cys Lys Cys Val Val Val Ser
    130                 135                 140 gtg aat tat cgg cgt gca cca gag aat cca tac cct tgt gct tat gat     480
Val Asn Tyr Arg Arg Ala Pro Glu Asn Pro Tyr Pro Cys Ala Tyr Asp
145                 150                 155                 160 gat ggt tgg att gct ctt aat tgg gtt aac tcg aga tct tgg ctt aaa     528
Asp Gly Trp Ile Ala Leu Asn Trp Val Asn Ser Arg Ser Trp Leu Lys
                165                 170                 175 tcc aag aaa gac tca aag gtc cat att ttc ttg gct ggt gat agc tct     576
Ser Lys Lys Asp Ser Lys Val His Ile Phe Leu Ala Gly Asp Ser Ser
            180                 185                 190 gga ggt aac atc gcg cat aat gtg gct tta aga gcg ggt gaa tcg gga     624
Gly Gly Asn Ile Ala His Asn Val Ala Leu Arg Ala Gly Glu Ser Gly
        195                 200                 205 atc gat gtt ttg ggg aac att ctg ctg aat cct atg ttt ggt ggg aat     672
Ile Asp Val Leu Gly Asn Ile Leu Leu Asn Pro Met Phe Gly Gly Asn
    210                 215                 220 gag aga acg gag tct gag aaa agt ttg gat ggg aaa tac ttt gtg acg     720
Glu Arg Thr Glu Ser Glu Lys Ser Leu Asp Gly Lys Tyr Phe Val Thr
225                 230                 235                 240 gtt aga gac cgc gat tgg tac tgg aaa gcg ttt tta ccc gag gga gaa     768
Val Arg Asp Arg Asp Trp Tyr Trp Lys Ala Phe Leu Pro Glu Gly Glu
                245                 250                 255
```

-continued

```
gat aga gag cat cca gcg tgt aat ccg ttt agc ccg aga ggg aaa agc      816
Asp Arg Glu His Pro Ala Cys Asn Pro Phe Ser Pro Arg Gly Lys Ser
        260                 265                 270 tta gaa gga gtg agt ttc ccc aag agt ctt gtg gtt gtc gcg ggt ttg      864
Leu Glu Gly Val Ser Phe Pro Lys Ser Leu Val Val Val Ala Gly Leu
275                 280                 285 gat ttg att aga gat tgg cag ttg gca tac gcg gaa ggg ctc aag aaa      912
Asp Leu Ile Arg Asp Trp Gln Leu Ala Tyr Ala Glu Gly Leu Lys Lys
        290                 295                 300 gcg ggt caa gag gtt aag ctt atg cat tta gag aaa gca act gtt ggg      960
Ala Gly Gln Glu Val Lys Leu Met His Leu Glu Lys Ala Thr Val Gly
305                 310                 315                 320 ttt tac ctc ttg cct aat aac aat cat ttc cat aat gtt atg gat gag     1008
Phe Tyr Leu Leu Pro Asn Asn Asn His Phe His Asn Val Met Asp Glu
                325                 330                 335 att tcg gcg ttt gta aac gcg gaa tgt                                  1035
Ile Ser Ala Phe Val Asn Ala Glu Cys
        340                 345
```

<210> SEQ ID NO 5
<211> LENGTH: 345
<212> TYPE: PRT
<213> ORGANISM: Arabidopsis thaliana

<400> SEQUENCE: 5

```
Met Ala Ala Ser Asp Glu Val Asn Leu Ile Glu Ser Arg Thr Val Val
1               5                   10                  15

Pro Leu Asn Thr Trp Val Leu Ile Ser Asn Phe Lys Val Ala Tyr Asn
            20                  25                  30

Ile Leu Arg Arg Pro Asp Gly Thr Phe Asn Arg His Leu Ala Glu Tyr
        35                  40                  45

Leu Asp Arg Lys Val Thr Ala Asn Ala Asn Pro Val Asp Gly Val Phe
    50                  55                  60

Ser Phe Asp Val Leu Ile Asp Arg Arg Ile Asn Leu Leu Ser Arg Val
65                  70                  75                  80

Tyr Arg Pro Ala Tyr Ala Asp Gln Glu Gln Pro Pro Ser Ile Leu Asp
                85                  90                  95

Leu Glu Lys Pro Val Asp Gly Asp Ile Val Pro Val Ile Leu Phe Phe
            100                 105                 110

His Gly Gly Ser Phe Ala His Ser Ser Ala Asn Ser Ala Ile Tyr Asp
        115                 120                 125

Thr Leu Cys Arg Arg Leu Val Gly Leu Cys Lys Cys Val Val Val Ser
    130                 135                 140

Val Asn Tyr Arg Arg Ala Pro Glu Asn Pro Tyr Pro Cys Ala Tyr Asp
145                 150                 155                 160

Asp Gly Trp Ile Ala Leu Asn Trp Val Asn Ser Arg Ser Trp Leu Lys
                165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
        195                 200                 205

Ile Asp Val Leu Gly Asn Ile Leu Leu Asn Pro Met Phe Gly Gly Asn
    210                 215                 220

Glu Arg Thr Glu Ser Glu Lys Ser Leu Asp Gly Lys Tyr Phe Val Thr
225                 230                 235                 240

Val Arg Asp Arg Asp Trp Tyr Trp Lys Ala Phe Leu Pro Glu Gly Glu
                245                 250                 255
```

```
Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Ala Gly Leu
        275                 280                 285

Asp Leu Ile Arg Asp Trp Gln Leu Ala Tyr Ala Glu Gly Leu Lys Lys
290                 295                 300

Ala Gly Gln Glu Val Lys Leu Met His Leu Glu Lys Ala Thr Val Gly
305                 310                 315                 320

Phe Tyr Leu Leu Pro Asn Asn Asn His Phe His Asn Val Met Asp Glu
                325                 330                 335

Ile Ser Ala Phe Val Asn Ala Glu Cys
                340                 345

<210> SEQ ID NO 6
<211> LENGTH: 1074
<212> TYPE: DNA
<213> ORGANISM: Arabidopsis thaliana
<220> FEATURE:
<221> NAME/KEY: CDS
<222> LOCATION: (1)..(1074)

<400> SEQUENCE: 6
```

| | | | | | | | | | | | | | | | | |
|---|---|---|---|---|---|---|---|---|---|---|---|---|---|---|---|---|
| atg gct ggt ggt aac gaa gtc aac ctt aac gaa tgc aag aga att gtc | | | | | | | | | | | | | | | | 48 |
| Met Ala Gly Gly Asn Glu Val Asn Leu Asn Glu Cys Lys Arg Ile Val | | | | | | | | | | | | | | | | |
| 1               5                  10                 15 | | | | | | | | | | | | | | | | |

```
cca ctc aac aca tgg gtc ctc att tcc aat ttc aag ctt gct tac aaa     96
Pro Leu Asn Thr Trp Val Leu Ile Ser Asn Phe Lys Leu Ala Tyr Lys
            20                  25                  30 gtc ctc cgt cgc cct gac ggt tct ttc aac cgc gac ctc gcc gag ttc    144
Val Leu Arg Arg Pro Asp Gly Ser Phe Asn Arg Asp Leu Ala Glu Phe
        35                  40                  45 ctt gac cgt aaa gtt ccc gcc aac tct ttc ccc ctc gac ggc gtt ttc    192
Leu Asp Arg Lys Val Pro Ala Asn Ser Phe Pro Leu Asp Gly Val Phe
    50                  55                  60 tcc ttc gac cac gtc gac tca aca act aac ctt ctc acc aga atc tac    240
Ser Phe Asp His Val Asp Ser Thr Thr Asn Leu Leu Thr Arg Ile Tyr
65                  70                  75                  80 caa cct gcg tct ctc ctt cat cag acc cgt cac gga acc ctc gag cta    288
Gln Pro Ala Ser Leu Leu His Gln Thr Arg His Gly Thr Leu Glu Leu
                85                  90                  95 acc aaa cct ctc agt act aca gag atc gtc cct gtt ctc att ttc ttc    336
Thr Lys Pro Leu Ser Thr Thr Glu Ile Val Pro Val Leu Ile Phe Phe
            100                 105                 110 cat gga ggc agc ttc act cat tcc tcc gcc aat agt gct atc tac gac    384
His Gly Gly Ser Phe Thr His Ser Ser Ala Asn Ser Ala Ile Tyr Asp
        115                 120                 125 act ttc tgc cga cgc ctt gtc acc att tgc ggt gtt gtt gtt gtc tct    432
Thr Phe Cys Arg Arg Leu Val Thr Ile Cys Gly Val Val Val Val Ser
    130                 135                 140 gtt gat tac cgg aga tcc cct gag cat cgc tac cct tgt gct tac gac    480
Val Asp Tyr Arg Arg Ser Pro Glu His Arg Tyr Pro Cys Ala Tyr Asp
145                 150                 155                 160 gat gga tgg aac gct ctc aac tgg gtc aag tcc aga gtc tgg ctt cag    528
Asp Gly Trp Asn Ala Leu Asn Trp Val Lys Ser Arg Val Trp Leu Gln
                165                 170                 175 agt ggt aaa gac tcc aat gtt tat gtt tat ttg gct gga gat agc tct    576
Ser Gly Lys Asp Ser Asn Val Tyr Val Tyr Leu Ala Gly Asp Ser Ser
            180                 185                 190 gga ggc aac att gct cac aat gtc gct gtc aga gct acc aat gaa gga    624
Gly Gly Asn Ile Ala His Asn Val Ala Val Arg Ala Thr Asn Glu Gly
```

-continued

```
                195                 200                 205
gtc aaa gtg ttg ggg aac att ctt ctt cat cca atg ttt ggt gga cag        672
Val Lys Val Leu Gly Asn Ile Leu Leu His Pro Met Phe Gly Gly Gln
    210                 215                 220 gag agg act cag tct gag aag acc ctt gat ggc aaa tac ttt gtg act        720
Glu Arg Thr Gln Ser Glu Lys Thr Leu Asp Gly Lys Tyr Phe Val Thr
225                 230                 235                 240 ata caa gat cga gat tgg tat tgg agg gct tat cta ccg gaa ggt gaa        768
Ile Gln Asp Arg Asp Trp Tyr Trp Arg Ala Tyr Leu Pro Glu Gly Glu
            245                 250                 255 gat aga gat cat cca gca tgt aat ccc ttt ggc ccg aga ggt caa agc        816
Asp Arg Asp His Pro Ala Cys Asn Pro Phe Gly Pro Arg Gly Gln Ser
        260                 265                 270 ctt aaa gga gtc aac ttt cca aag agt ctt gtt gtt gtc gct ggt tta        864
Leu Lys Gly Val Asn Phe Pro Lys Ser Leu Val Val Val Ala Gly Leu
    275                 280                 285 gat ctt gtt caa gat tgg caa tta gcc tat gtg gat ggg ctt aag aag        912
Asp Leu Val Gln Asp Trp Gln Leu Ala Tyr Val Asp Gly Leu Lys Lys
290                 295                 300 act ggt ctt gaa gtc aat ctt ttg tat ttg aaa caa gct acc att ggc        960
Thr Gly Leu Glu Val Asn Leu Leu Tyr Leu Lys Gln Ala Thr Ile Gly
305                 310                 315                 320 ttt tac ttc ttg cct aac aat gat cac ttt cat tgt ctt atg gaa gag       1008
Phe Tyr Phe Leu Pro Asn Asn Asp His Phe His Cys Leu Met Glu Glu
            325                 330                 335 ttg aat aag ttt gtg cac tcc ata gag gat tct caa agc aag tca agt       1056
Leu Asn Lys Phe Val His Ser Ile Glu Asp Ser Gln Ser Lys Ser Ser
        340                 345                 350 cct gtg ctt ctt act cct                                               1074
Pro Val Leu Leu Thr Pro
        355
```

<210> SEQ ID NO 7
<211> LENGTH: 358
<212> TYPE: PRT
<213> ORGANISM: Arabidopsis thaliana

<400> SEQUENCE: 7

```
Met Ala Gly Gly Asn Glu Val Asn Leu Asn Glu Cys Lys Arg Ile Val
1               5                   10                  15

Pro Leu Asn Thr Trp Val Leu Ile Ser Asn Phe Lys Leu Ala Tyr Lys
                20                  25                  30

Val Leu Arg Arg Pro Asp Gly Ser Phe Asn Arg Asp Leu Ala Glu Phe
            35                  40                  45

Leu Asp Arg Lys Val Pro Ala Asn Ser Phe Pro Leu Asp Gly Val Phe
        50                  55                  60

Ser Phe Asp His Val Asp Ser Thr Thr Asn Leu Leu Thr Arg Ile Tyr
65                  70                  75                  80

Gln Pro Ala Ser Leu Leu His Gln Thr Arg His Gly Thr Leu Glu Leu
                85                  90                  95

Thr Lys Pro Leu Ser Thr Thr Glu Ile Val Pro Val Leu Ile Phe Phe
            100                 105                 110

His Gly Gly Ser Phe Thr His Ser Ser Ala Asn Ser Ala Ile Tyr Asp
        115                 120                 125

Thr Phe Cys Arg Arg Leu Val Thr Ile Cys Gly Val Val Val Val Ser
    130                 135                 140

Val Asp Tyr Arg Arg Ser Pro Glu His Arg Tyr Pro Cys Ala Tyr Asp
145                 150                 155                 160
```

```
Asp Gly Trp Asn Ala Leu Asn Trp Val Lys Ser Arg Val Trp Leu Gln
                165                 170                 175

Ser Gly Lys Asp Ser Asn Val Tyr Val Tyr Leu Ala Gly Asp Ser Ser
            180                 185                 190

Gly Gly Asn Ile Ala His Asn Val Ala Val Arg Ala Thr Asn Glu Gly
        195                 200                 205

Val Lys Val Leu Gly Asn Ile Leu Leu His Pro Met Phe Gly Gly Gln
    210                 215                 220

Glu Arg Thr Gln Ser Glu Lys Thr Leu Asp Gly Lys Tyr Phe Val Thr
225                 230                 235                 240

Ile Gln Asp Arg Asp Trp Tyr Trp Arg Ala Tyr Leu Pro Glu Gly Glu
                245                 250                 255

Asp Arg Asp His Pro Ala Cys Asn Pro Phe Gly Pro Arg Gly Gln Ser
            260                 265                 270

Leu Lys Gly Val Asn Phe Pro Lys Ser Leu Val Val Ala Gly Leu
        275                 280                 285

Asp Leu Val Gln Asp Trp Gln Leu Ala Tyr Val Asp Gly Leu Lys Lys
    290                 295                 300

Thr Gly Leu Glu Val Asn Leu Leu Tyr Leu Lys Gln Ala Thr Ile Gly
305                 310                 315                 320

Phe Tyr Phe Leu Pro Asn Asn Asp His Phe His Cys Leu Met Glu Glu
                325                 330                 335

Leu Asn Lys Phe Val His Ser Ile Glu Asp Ser Gln Ser Lys Ser Ser
            340                 345                 350

Pro Val Leu Leu Thr Pro
        355

<210> SEQ ID NO 8
<211> LENGTH: 1035
<212> TYPE: DNA
<213> ORGANISM: Arabidopsis thaliana
<220> FEATURE:
<221> NAME/KEY: CDS
<222> LOCATION: (1)..(1035)

<400> SEQUENCE: 8 atg gct gcg agc gat gaa gtt aat ctt att gag agc aga aca gtg gtt      48
Met Ala Ala Ser Asp Glu Val Asn Leu Ile Glu Ser Arg Thr Val Val
1               5                   10                  15 cct ctc aat aca tgg gtt tta ata tcc aac ttc aaa gta gcc tac aat      96
Pro Leu Asn Thr Trp Val Leu Ile Ser Asn Phe Lys Val Ala Tyr Asn
                20                  25                  30 atc ctt cgt cgc cct gat gga acc ttt aac cga cac tta gct gag tat     144
Ile Leu Arg Arg Pro Asp Gly Thr Phe Asn Arg His Leu Ala Glu Tyr
            35                  40                  45 cta gac cgt aaa gtc act gca aac gcc aat ccg gtt gat ggg gtt ttc     192
Leu Asp Arg Lys Val Thr Ala Asn Ala Asn Pro Val Asp Gly Val Phe
        50                  55                  60 tcg ttc gat gtc ttg att gat cgc agg atc aat ctt cta agc aga gtc     240
Ser Phe Asp Val Leu Ile Asp Arg Arg Ile Asn Leu Leu Ser Arg Val
65                  70                  75                  80 tat aga cca gct tat gca gat caa gag caa cct cct agt att tta gat     288
Tyr Arg Pro Ala Tyr Ala Asp Gln Glu Gln Pro Pro Ser Ile Leu Asp
                85                  90                  95 ctc gag aag cct gtt gat ggc gac att gtc cct gtt ata ttg ttc ttc     336
Leu Glu Lys Pro Val Asp Gly Asp Ile Val Pro Val Ile Leu Phe Phe
            100                 105                 110 cat gga ggt agc ttt gct cat tct tct gca aac agt gcc atc tac gat     384
His Gly Gly Ser Phe Ala His Ser Ser Ala Asn Ser Ala Ile Tyr Asp
```

```
                  115                 120                 125
act ctt tgt cgc agg ctt gtt ggt ttg tgc aag tgt gtt gtt gtc tct     432
Thr Leu Cys Arg Arg Leu Val Gly Leu Cys Lys Cys Val Val Val Ser
    130                 135                 140 gtg aat tat cgg cgt gca cca gag aat cca tac cct tgt gct tat gat     480
Val Asn Tyr Arg Arg Ala Pro Glu Asn Pro Tyr Pro Cys Ala Tyr Asp
145                 150                 155                 160 gat ggt tgg att gct ctt aat tgg gtt aac tcg aga tct tgg ctt aaa     528
Asp Gly Trp Ile Ala Leu Asn Trp Val Asn Ser Arg Ser Trp Leu Lys
                165                 170                 175 tcc aag aaa gac tca aag gtc cat att ttc ttg gct ggt gat agc tct     576
Ser Lys Lys Asp Ser Lys Val His Ile Phe Leu Ala Gly Asp Ser Ser
            180                 185                 190 gga ggt aac atc gcg cat aat gtg gct tta aga gcg ggt gaa tcg gga     624
Gly Gly Asn Ile Ala His Asn Val Ala Leu Arg Ala Gly Glu Ser Gly
        195                 200                 205 atc gat gtt ttg ggg aac att ctg ctg aat cct atg ttt ggt ggg aat     672
Ile Asp Val Leu Gly Asn Ile Leu Leu Asn Pro Met Phe Gly Gly Asn
    210                 215                 220 gag aga acg gag tct gag aaa agt ttg gat ggg aaa tac ttt gtg acg     720
Glu Arg Thr Glu Ser Glu Lys Ser Leu Asp Gly Lys Tyr Phe Val Thr
225                 230                 235                 240 gtt aga gac cgc gat tgg tac tgg aaa gcg ttt tta ccc gag gga gaa     768
Val Arg Asp Arg Asp Trp Tyr Trp Lys Ala Phe Leu Pro Glu Gly Glu
                245                 250                 255 gat aga gag cat cca gcg tgt aat ccg ttt agc ccg aga ggg aaa agc     816
Asp Arg Glu His Pro Ala Cys Asn Pro Phe Ser Pro Arg Gly Lys Ser
            260                 265                 270 tta gaa gga gtg agt ttc ccc aag agt ctt gtg gtt gtc gcg ggt ttg     864
Leu Glu Gly Val Ser Phe Pro Lys Ser Leu Val Val Val Ala Gly Leu
        275                 280                 285 gat ttg att aga gat tgg cag ttg gca tac gcg gaa ggg ctc aag aaa     912
Asp Leu Ile Arg Asp Trp Gln Leu Ala Tyr Ala Glu Gly Leu Lys Lys
    290                 295                 300 gcg ggt caa gag gtt aag ctt atg cat tta gag aaa gca act gtt ggg     960
Ala Gly Gln Glu Val Lys Leu Met His Leu Glu Lys Ala Thr Val Gly
305                 310                 315                 320 ttt tac ctc ttg cct aat aac aat cat ttc cat aat gtt atg gat gag    1008
Phe Tyr Leu Leu Pro Asn Asn Asn His Phe His Asn Val Met Asp Glu
                325                 330                 335 att tcg gcg ttt gta aac gcg gaa tgt                                1035
Ile Ser Ala Phe Val Asn Ala Glu Cys
            340                 345

<210> SEQ ID NO 9
<211> LENGTH: 345
<212> TYPE: PRT
<213> ORGANISM: Arabidopsis thaliana

<400> SEQUENCE: 9

Met Ala Ala Ser Asp Glu Val Asn Leu Ile Glu Ser Arg Thr Val Val
1               5                   10                  15

Pro Leu Asn Thr Trp Val Leu Ile Ser Asn Phe Lys Val Ala Tyr Asn
            20                  25                  30

Ile Leu Arg Arg Pro Asp Gly Thr Phe Asn Arg His Leu Ala Glu Tyr
        35                  40                  45

Leu Asp Arg Lys Val Thr Ala Asn Ala Asn Pro Val Asp Gly Val Phe
    50                  55                  60

Ser Phe Asp Val Leu Ile Asp Arg Ile Asn Leu Leu Ser Arg Val
65                  70                  75                  80
```

```
Tyr Arg Pro Ala Tyr Ala Asp Gln Glu Gln Pro Ser Ile Leu Asp
                85                  90                  95

Leu Glu Lys Pro Val Asp Gly Asp Ile Val Pro Val Ile Leu Phe Phe
            100                 105                 110

His Gly Gly Ser Phe Ala His Ser Ser Ala Asn Ser Ala Ile Tyr Asp
            115                 120                 125

Thr Leu Cys Arg Arg Leu Val Gly Leu Cys Lys Cys Val Val Ser
130                 135                 140

Val Asn Tyr Arg Arg Ala Pro Glu Asn Pro Tyr Pro Cys Ala Tyr Asp
145                 150                 155                 160

Asp Gly Trp Ile Ala Leu Asn Trp Val Asn Ser Arg Ser Trp Leu Lys
            165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
            195                 200                 205

Ile Asp Val Leu Gly Asn Ile Leu Leu Asn Pro Met Phe Gly Gly Asn
210                 215                 220

Glu Arg Thr Glu Ser Glu Lys Ser Leu Asp Gly Lys Tyr Phe Val Thr
225                 230                 235                 240

Val Arg Asp Arg Asp Trp Tyr Trp Lys Ala Phe Leu Pro Glu Gly Glu
            245                 250                 255

Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Ala Gly Leu
            275                 280                 285

Asp Leu Ile Arg Asp Trp Gln Leu Ala Tyr Ala Glu Gly Leu Lys Lys
290                 295                 300

Ala Gly Gln Glu Val Lys Leu Met His Leu Glu Lys Ala Thr Val Gly
305                 310                 315                 320

Phe Tyr Leu Leu Pro Asn Asn Asn His Phe His Asn Val Met Asp Glu
            325                 330                 335

Ile Ser Ala Phe Val Asn Ala Glu Cys
            340                 345

<210> SEQ ID NO 10
<211> LENGTH: 335
<212> TYPE: PRT
<213> ORGANISM: Arabidopsis thaliana

<400> SEQUENCE: 10

Met Ala Thr Asp Ser Gln Pro Asn Gln Lys Leu Thr Leu Pro Leu Lys
1               5                   10                  15

Thr Arg Ile Ala Leu Thr Val Ile Ser Thr Met Thr Asp Asn Ala Gln
            20                  25                  30

Arg Pro Asp Gly Thr Ile Asn Arg Arg Phe Leu Arg Leu Phe Asp Phe
        35                  40                  45

Arg Ala Pro Pro Asn Pro Lys Pro Val Asn Ile Val Ser Thr Ser Asp
    50                  55                  60

Phe Val Val Asp Gln Ser Arg Asp Leu Trp Phe Arg Leu Tyr Thr Pro
65                  70                  75                  80

His Val Ser Gly Asp Lys Ile Pro Val Val Phe His Gly Gly
            85                  90                  95

Gly Phe Ala Phe Leu Ser Pro Asn Ala Tyr Pro Tyr Asn Val Cys
            100                 105                 110
```

```
Arg Arg Phe Ala Arg Lys Leu Pro Ala Tyr Val Ile Ser Val Asn Tyr
            115                 120                 125

Arg Leu Ala Pro Glu His Arg Tyr Pro Ala Gln Tyr Asp Asp Gly Phe
        130                 135                 140

Asp Ala Leu Lys Tyr Ile Glu Glu Asn His Gly Ser Ile Leu Pro Ala
145                 150                 155                 160

Asn Ala Asp Leu Ser Arg Cys Phe Phe Ala Gly Asp Ser Ala Gly Gly
                165                 170                 175

Asn Ile Ala His Asn Val Ala Ile Arg Ile Cys Arg Glu Pro Arg Ser
                180                 185                 190

Ser Phe Thr Ala Val Lys Leu Ile Gly Leu Ile Ser Ile Gln Pro Phe
        195                 200                 205

Phe Gly Gly Glu Glu Arg Thr Glu Ala Glu Lys Gln Leu Val Gly Ala
        210                 215                 220

Pro Leu Val Ser Pro Asp Arg Thr Asp Trp Cys Trp Lys Ala Met Gly
225                 230                 235                 240

Leu Asn Arg Asp His Glu Ala Val Asn Val Gly Gly Pro Asn Ala Val
                245                 250                 255

Asp Ile Ser Gly Leu Asp Tyr Pro Glu Thr Met Val Val Val Ala Gly
                260                 265                 270

Phe Asp Pro Leu Lys Asp Trp Gln Arg Ser Tyr Tyr Glu Trp Leu Lys
        275                 280                 285

Leu Cys Gly Lys Lys Ala Thr Leu Ile Glu Tyr Pro Asn Met Phe His
        290                 295                 300

Ala Phe Tyr Ile Phe Pro Glu Leu Pro Glu Ala Gly Gln Leu Ile Met
305                 310                 315                 320

Arg Ile Lys Asp Phe Val Asp Glu Arg Val Ala Ser Leu Ser Ala
                325                 330                 335

<210> SEQ ID NO 11
<211> LENGTH: 329
<212> TYPE: PRT
<213> ORGANISM: Arabidopsis thaliana

<400> SEQUENCE: 11

Met Gly Ser Leu Gly Glu Glu Pro Gln Val Ala Glu Asp Cys Met Gly
1               5                   10                  15

Leu Leu Gln Leu Leu Ser Asn Gly Thr Val Leu Arg Ser Glu Ser Ile
            20                  25                  30

Asp Leu Ile Thr Gln Gln Ile Pro Phe Lys Asn Asn Gln Thr Val Leu
        35                  40                  45

Phe Lys Asp Ser Ile Tyr His Lys Pro Asn Asn Leu His Leu Arg Leu
    50                  55                  60

Tyr Lys Pro Ile Ser Ala Ser Asn Arg Thr Ala Leu Pro Val Val Val
65                  70                  75                  80

Phe Phe His Gly Gly Gly Phe Cys Phe Gly Ser Arg Ser Trp Pro His
                85                  90                  95

Phe His Asn Phe Cys Leu Thr Leu Ala Ser Ser Leu Asn Ala Leu Val
            100                 105                 110

Val Ser Pro Asp Tyr Arg Leu Ala Pro Glu His Arg Leu Pro Ala Ala
        115                 120                 125

Phe Glu Asp Ala Glu Ala Val Leu Thr Trp Leu Trp Asp Gln Ala Val
    130                 135                 140

Ser Asp Gly Val Asn His Trp Phe Glu Asp Gly Thr Asp Val Asp Phe
145                 150                 155                 160
```

Asp Arg Val Phe Val Gly Asp Ser Ser Gly Gly Asn Ile Ala His
                165                 170                 175

Gln Leu Ala Val Arg Phe Gly Ser Gly Ser Ile Glu Leu Thr Pro Val
                180                 185                 190

Arg Val Arg Gly Tyr Val Leu Met Gly Pro Phe Phe Gly Gly Glu Glu
            195                 200                 205

Arg Thr Asn Ser Glu Asn Gly Pro Ser Glu Ala Leu Leu Ser Leu Asp
            210                 215                 220

Leu Leu Asp Lys Phe Trp Arg Leu Ser Leu Pro Asn Gly Ala Thr Arg
225                 230                 235                 240

Asp His His Met Ala Asn Pro Phe Gly Pro Thr Ser Pro Thr Leu Glu
                245                 250                 255

Ser Ile Ser Leu Glu Pro Met Leu Val Ile Val Gly Ser Glu Leu
            260                 265                 270

Leu Arg Asp Arg Ala Lys Glu Tyr Ala Tyr Lys Leu Lys Lys Met Gly
            275                 280                 285

Gly Lys Arg Val Asp Tyr Ile Glu Phe Glu Asn Lys Glu His Gly Phe
            290                 295                 300

Tyr Ser Asn Tyr Pro Ser Ser Glu Ala Ala Glu Gln Val Leu Arg Ile
305                 310                 315                 320

Ile Gly Asp Phe Met Asn Asn Leu Ser
                325

<210> SEQ ID NO 12
<211> LENGTH: 327
<212> TYPE: PRT
<213> ORGANISM: Arabidopsis thaliana

<400> SEQUENCE: 12

Met Ser Glu Pro Ser Pro Ile Ala Asp Pro Tyr Ala Tyr Leu Asn Ile
1               5                   10                  15

Val Asn Asn Pro Asp Gly Ser Ile Thr Arg Asp Leu Ser Asn Phe Pro
                20                  25                  30

Cys Thr Ala Ala Thr Pro Asp Pro Ser Pro Leu Asn Pro Ala Val Ser
            35                  40                  45

Lys Asp Leu Pro Val Asn Gln Leu Lys Ser Thr Trp Leu Arg Leu Tyr
50                  55                  60

Leu Pro Ser Ser Ala Val Asn Glu Gly Asn Val Ser Ser Gln Lys Leu
65                  70                  75                  80

Pro Ile Val Val Tyr Tyr His Gly Gly Gly Phe Ile Leu Cys Ser Val
                85                  90                  95

Asp Met Gln Leu Phe His Asp Phe Cys Ser Glu Val Ala Arg Asp Leu
            100                 105                 110

Asn Ala Ile Val Val Ser Pro Ser Tyr Arg Leu Ala Pro Glu His Arg
            115                 120                 125

Leu Pro Ala Ala Tyr Asp Asp Gly Val Glu Ala Leu Asp Trp Ile Lys
            130                 135                 140

Thr Ser Asp Asp Glu Trp Ile Lys Ser His Ala Asp Phe Ser Asn Val
145                 150                 155                 160

Phe Leu Met Gly Thr Ser Ala Gly Gly Asn Leu Ala Tyr Asn Val Gly
                165                 170                 175

Leu Arg Ser Val Asp Ser Val Ser Asp Leu Ser Pro Leu Gln Ile Arg
            180                 185                 190

Gly Leu Ile Leu His His Pro Phe Phe Gly Gly Glu Glu Arg Ser Glu
            195                 200                 205

```
Ser Glu Ile Arg Leu Met Asn Asp Gln Val Cys Pro Pro Ile Val Thr
    210                 215                 220

Asp Val Met Trp Asp Leu Ser Leu Pro Val Gly Val Asp Arg Asp His
225                 230                 235                 240

Glu Tyr Ser Asn Pro Thr Val Gly Asp Gly Ser Glu Lys Leu Glu Lys
                245                 250                 255

Ile Gly Arg Leu Arg Trp Lys Val Met Met Ile Gly Gly Glu Asp Asp
            260                 265                 270

Pro Met Ile Asp Leu Gln Lys Asp Val Ala Lys Leu Met Lys Lys Lys
                275                 280                 285

Gly Val Glu Val Val Glu His Tyr Thr Gly Gly His Val His Gly Ala
    290                 295                 300

Glu Ile Arg Asp Pro Ser Lys Arg Lys Thr Leu Phe Leu Ser Ile Lys
305                 310                 315                 320

Asn Phe Ile Phe Ser Val Leu
                325

<210> SEQ ID NO 13
<211> LENGTH: 329
<212> TYPE: PRT
<213> ORGANISM: Arabidopsis thaliana

<400> SEQUENCE: 13

Met Asp Ser Glu Ile Ala Ala Asp Tyr Ser Pro Met Leu Ile Ile Tyr
1               5                   10                  15

Lys Ser Gly Arg Ile Glu Arg Leu Val Gly Thr Thr Val Pro Pro
            20                  25                  30

Ser Ser Asn Pro Gln Asn Gly Val Val Ser Lys Asp Val Val Tyr Ser
        35                  40                  45

Pro Asp Asn Asn Leu Ser Leu Arg Ile Tyr Leu Pro Glu Lys Ala Ala
50                  55                  60

Thr Ala Glu Thr Glu Ala Ser Val Lys Leu Pro Leu Leu Val Tyr Phe
65                  70                  75                  80

His Gly Gly Gly Phe Leu Val Glu Thr Ala Phe Ser Pro Thr Tyr His
                85                  90                  95

Thr Phe Leu Thr Ala Ala Val Ser Ala Ser Asp Cys Val Ala Val Ser
            100                 105                 110

Val Asp Tyr Arg Arg Ala Pro Glu His Pro Ile Pro Thr Ser Tyr Asp
        115                 120                 125

Asp Ser Trp Thr Ala Leu Lys Trp Val Phe Ser His Ile Ala Gly Ser
130                 135                 140

Gly Ser Glu Asp Trp Leu Asn Lys His Ala Asp Phe Ser Lys Val Phe
145                 150                 155                 160

Leu Ala Gly Asp Ser Ala Gly Ala Asn Ile Thr His His Met Thr Met
                165                 170                 175

Lys Ala Ala Lys Asp Lys Leu Ser Pro Glu Ser Leu Asn Glu Ser Gly
            180                 185                 190

Ile Ser Gly Ile Ile Leu Val His Pro Tyr Phe Trp Ser Lys Thr Pro
        195                 200                 205

Val Asp Asp Lys Glu Thr Thr Asp Val Ala Ile Arg Thr Trp Ile Glu
210                 215                 220

Ser Val Trp Thr Leu Ala Ser Pro Asn Ser Lys Asp Gly Ser Asp Asp
225                 230                 235                 240

Pro Phe Ile Asn Val Val Gln Ser Glu Ser Val Asp Leu Ser Gly Leu
                245                 250                 255
```

```
Gly Cys Gly Lys Val Leu Val Met Val Ala Glu Lys Asp Ala Leu Val
            260                 265                 270

Arg Gln Gly Trp Gly Tyr Trp Glu Lys Leu Gly Lys Ser Arg Trp Asn
        275                 280                 285

Gly Glu Val Leu Asp Val Val Glu Thr Lys Gly Glu Gly His Val Phe
    290                 295                 300

His Leu Arg Asp Pro Asn Ser Glu Lys Ala His Glu Leu Val His Arg
305                 310                 315                 320

Phe Ala Gly Phe Ile Lys Gly Asp Lys
                325

<210> SEQ ID NO 14
<211> LENGTH: 314
<212> TYPE: PRT
<213> ORGANISM: Arabidopsis thaliana

<400> SEQUENCE: 14

Met Glu Ser Thr Lys Lys Gln Val Ser Leu Glu Leu Pro Trp Leu
1               5                   10                  15

Val Val His Thr Asp Gly Thr Val Glu Arg Leu Ala Gly Thr Glu Val
            20                  25                  30

Cys Pro Pro Gly Leu Asp Pro Ile Thr Gly Val Phe Ser Lys Asp Ile
        35                  40                  45

Ile Glu Pro Lys Thr Gly Leu Ser Ala Arg Ile Tyr Arg Pro Phe
    50                  55                  60

Ser Ile Gln Pro Gly Gln Lys Ile Pro Leu Met Leu Tyr Phe His Gly
65                  70                  75                  80

Gly Ala Phe Leu Ile Ser Ser Thr Ser Phe Pro Ser Tyr His Thr Ser
                85                  90                  95

Leu Asn Lys Ile Val Asn Gln Ala Asn Val Ile Ala Val Ser Val Asn
            100                 105                 110

Tyr Arg Leu Ala Pro Glu His Pro Leu Pro Thr Ala Tyr Glu Asp Ser
        115                 120                 125

Trp Thr Ala Leu Lys Asn Ile Gln Ala Ile Asn Glu Pro Trp Ile Asn
    130                 135                 140

Asp Tyr Ala Asp Leu Asp Ser Leu Phe Leu Val Gly Asp Ser Ala Gly
145                 150                 155                 160

Ala Asn Ile Ser His His Leu Ala Phe Arg Ala Lys Gln Ser Asp Gln
                165                 170                 175

Thr Leu Lys Ile Lys Gly Ile Gly Met Ile His Pro Tyr Phe Trp Gly
            180                 185                 190

Thr Gln Pro Ile Gly Ala Glu Ile Lys Asp Glu Ala Arg Lys Gln Met
        195                 200                 205

Val Asp Gly Trp Trp Glu Phe Val Cys Pro Ser Glu Lys Gly Ser Asp
    210                 215                 220

Asp Pro Trp Ile Asn Pro Phe Ala Asp Gly Ser Pro Asp Leu Gly Gly
225                 230                 235                 240

Leu Gly Cys Glu Arg Val Met Ile Thr Val Ala Glu Lys Asp Ile Leu
                245                 250                 255

Asn Glu Arg Gly Lys Met Tyr Tyr Glu Arg Leu Val Lys Ser Glu Trp
            260                 265                 270

Lys Gly Lys Val Glu Ile Met Glu Thr Lys Glu Lys Asp His Val Phe
        275                 280                 285

His Ile Phe Glu Pro Asp Cys Asp Glu Ala Met Glu Met Val Arg Cys
    290                 295                 300
```

Leu Ala Leu Phe Ile Asn Gln Val Glu Ala
305                 310

<210> SEQ ID NO 15
<211> LENGTH: 344
<212> TYPE: PRT
<213> ORGANISM: Arabidopsis thaliana

<400> SEQUENCE: 15

Met Ala Thr Ile Ser Phe Ser His Asn His Gln Ser Ser Asp Asn Arg
1               5                   10                  15

Arg Gly Gly Ser His His His Arg His Gly Pro Val Val Glu Glu Ile
            20                  25                  30

Glu Gly Leu Ile Lys Val Phe Asn Asp Gly Cys Val Glu Arg Pro Pro
        35                  40                  45

Ile Val Pro Ile Val Ser Pro Thr Ile His Pro Ser Ser Lys Ala Thr
    50                  55                  60

Ala Phe Asp Ile Lys Leu Ser Asn Asp Thr Trp Thr Arg Val Tyr Ile
65                  70                  75                  80

Pro Asp Ala Ala Ala Ser Pro Ser Val Thr Leu Pro Leu Leu Val
                85                  90                  95

Tyr Phe His Gly Gly Gly Phe Cys Val Gly Ser Ala Ala Trp Ser Cys
                100                 105                 110

Tyr His Asp Phe Leu Thr Ser Leu Ala Val Lys Ala Arg Cys Val Ile
                115                 120                 125

Val Ser Val Asn Tyr Arg Leu Ala Pro Glu His Arg Leu Pro Ala Ala
    130                 135                 140

Tyr Asp Asp Gly Val Asn Val Val Ser Trp Leu Val Lys Gln Gln Ile
145                 150                 155                 160

Ser Thr Gly Gly Gly Tyr Pro Ser Trp Leu Ser Lys Cys Asn Leu Ser
                165                 170                 175

Asn Val Phe Leu Ala Gly Asp Ser Ala Gly Ala Asn Ile Ala Tyr Gln
                180                 185                 190

Val Ala Val Arg Ile Met Ala Ser Gly Lys Tyr Ala Asn Thr Leu His
    195                 200                 205

Leu Lys Gly Ile Ile Leu Ile His Pro Phe Phe Gly Gly Glu Ser Arg
210                 215                 220

Thr Ser Ser Glu Lys Gln Gln His His Thr Lys Ser Ser Ala Leu Thr
225                 230                 235                 240

Leu Ser Ala Ser Asp Ala Tyr Trp Arg Leu Ala Leu Pro Arg Gly Ala
                245                 250                 255

Ser Arg Asp His Pro Trp Cys Asn Pro Leu Met Ser Ser Ala Gly Ala
                260                 265                 270

Lys Leu Pro Thr Thr Met Val Phe Met Ala Glu Phe Asp Ile Leu Lys
                275                 280                 285

Glu Arg Asn Leu Glu Met Cys Lys Val Met Arg Ser His Gly Lys Arg
    290                 295                 300

Val Glu Gly Ile Val His Gly Gly Val Gly His Ala Phe His Ile Leu
305                 310                 315                 320

Asp Asn Ser Ser Val Ser Arg Asp Arg Ile His Asp Met Met Cys Arg
                325                 330                 335

Leu His Asn Phe Ile His Pro Ser
            340

<210> SEQ ID NO 16

<211> LENGTH: 336
<212> TYPE: PRT
<213> ORGANISM: Arabidopsis thaliana

<400> SEQUENCE: 16

Met Gly Gly Thr Lys Leu Thr His Val Thr Thr Asn Pro Asn Asn
1               5                   10                  15

Ser Asn Ile His Gly Pro Val Val Asp Glu Val Glu Gly Leu Ile Lys
            20                  25                  30

Val Tyr Lys Asp Gly His Val Glu Arg Ser Gln Leu Leu Pro Cys Val
            35                  40                  45

Asp Pro Ser Leu Pro Leu Glu Leu Gly Val Thr Cys Ser Asp Val Val
50                  55                  60

Ile Asp Lys Leu Thr Asn Val Trp Ala Arg Leu Tyr Val Pro Met Thr
65                  70                  75                  80

Thr Thr Lys Ser Ser Val Ser Lys Leu Pro Leu Ile Val Tyr Phe His
                85                  90                  95

Gly Gly Gly Phe Cys Val Gly Ser Ala Ser Trp Leu Cys Tyr His Glu
            100                 105                 110

Phe Leu Ala Arg Leu Ser Ala Arg Ser Arg Cys Leu Val Met Ser Val
            115                 120                 125

Asn Tyr Arg Leu Ala Pro Glu Asn Pro Leu Pro Ala Ala Tyr Glu Asp
130                 135                 140

Gly Val Asn Ala Ile Leu Trp Leu Asn Lys Ala Arg Asn Asp Asn Leu
145                 150                 155                 160

Trp Ala Lys Gln Cys Asp Phe Gly Arg Ile Phe Leu Ala Gly Asp Ser
                165                 170                 175

Ala Gly Gly Asn Ile Ala Gln Gln Val Ala Ala Arg Leu Ala Ser Pro
            180                 185                 190

Glu Asp Leu Ala Leu Lys Ile Glu Gly Thr Ile Leu Ile Gln Pro Phe
            195                 200                 205

Tyr Ser Gly Glu Glu Arg Thr Glu Ser Glu Arg Arg Val Gly Asn Asp
210                 215                 220

Lys Thr Ala Val Leu Thr Leu Ala Ser Ser Asp Ala Trp Trp Arg Met
225                 230                 235                 240

Ser Leu Pro Arg Gly Ala Asn Arg Glu His Pro Tyr Cys Lys Pro Val
                245                 250                 255

Lys Met Ile Ile Lys Ser Ser Thr Val Thr Arg Thr Leu Val Cys Val
            260                 265                 270

Ala Glu Met Asp Leu Leu Met Asp Ser Asn Met Glu Met Cys Asp Gly
            275                 280                 285

Asn Glu Asp Val Ile Lys Arg Val Leu His Lys Gly Val Gly His Ala
290                 295                 300

Phe His Ile Leu Gly Lys Ser Gln Leu Ala His Thr Thr Thr Leu Glu
305                 310                 315                 320

Met Leu Cys Gln Ile Asp Ala Phe Ile His His Tyr Asp Pro Leu Asn
                325                 330                 335

<210> SEQ ID NO 17
<211> LENGTH: 22
<212> TYPE: DNA
<213> ORGANISM: Artificial
<220> FEATURE:
<223> OTHER INFORMATION: an artificially synthesized sequence

<400> SEQUENCE: 17
cagatcaaga gcaacctcct ag                                              22

```
<210> SEQ ID NO 18
<211> LENGTH: 26
<212> TYPE: DNA
<213> ORGANISM: Artificial
<220> FEATURE:
<223> OTHER INFORMATION: an artificially synthesized sequence

<400> SEQUENCE: 18
ccacaggcaa tacattcacc tgtgtg                                           26

<210> SEQ ID NO 19
<211> LENGTH: 26
<212> TYPE: DNA
<213> ORGANISM: Artificial
<220> FEATURE:
<223> OTHER INFORMATION: an artificially synthesized sequence

<400> SEQUENCE: 19
gaaccctcga gctaaccaaa cctctc                                           26

<210> SEQ ID NO 20
<211> LENGTH: 28
<212> TYPE: DNA
<213> ORGANISM: Artificial
<220> FEATURE:
<223> OTHER INFORMATION: an artificially synthesized sequence

<400> SEQUENCE: 20
ggagtaagaa gcacaggact tgacttgc                                         28

<210> SEQ ID NO 21
<211> LENGTH: 24
<212> TYPE: DNA
<213> ORGANISM: Artificial
<220> FEATURE:
<223> OTHER INFORMATION: an artificially synthesized sequence

<400> SEQUENCE: 21
ctggcacttc accaagtatt actg                                             24

<210> SEQ ID NO 22
<211> LENGTH: 22
<212> TYPE: DNA
<213> ORGANISM: Artificial
<220> FEATURE:
<223> OTHER INFORMATION: an artificially synthesized sequence

<400> SEQUENCE: 22
gccaatagtg gcttgctcca ag                                               22

<210> SEQ ID NO 23
<211> LENGTH: 20
<212> TYPE: DNA
<213> ORGANISM: Artificial
<220> FEATURE:
<223> OTHER INFORMATION: an artificially synthesized sequence

<400> SEQUENCE: 23
tccatcttgg catctctcag                                                  20

<210> SEQ ID NO 24
<211> LENGTH: 20
<212> TYPE: DNA
<213> ORGANISM: Artificial
<220> FEATURE:
<223> OTHER INFORMATION: an artificially synthesized sequence
```

```
<400> SEQUENCE: 24
gtaccctcat caggcatctg                                              20

<210> SEQ ID NO 25
<211> LENGTH: 26
<212> TYPE: DNA
<213> ORGANISM: Artificial
<220> FEATURE:
<223> OTHER INFORMATION: an artificially synthesized sequence

<400> SEQUENCE: 25
cgtgtgtgac aatggtaccg gtatgg                                       26

<210> SEQ ID NO 26
<211> LENGTH: 26
<212> TYPE: DNA
<213> ORGANISM: Artificial
<220> FEATURE:
<223> OTHER INFORMATION: an artificially synthesized sequence

<400> SEQUENCE: 26
ctgtgaacga ttcctggacc tgcctc                                       26
```

REGULATORY GENES FOR PLANT DIFFERENTIATION AND GROWTH, AND USE OF THE SAME

TECHNICAL FIELD

The present invention relates to regulatory genes for plant differentiation and growth, and methods for regulating plant differentiation and growth using such genes. The regulation of plant differentiation and growth is useful in the field of plant breeding and the like.

BACKGROUND ART

Gibberellins (GA) are a plant hormone family of tetracyclic diterpenoids, compounds essential for diverse developmental processes in plants, including growth, flowering, and fructification (Non-patent Document 1). In particular, by regulating the activity of GA, one can control the growth and differentiation of various plants. For example, crop yield varies greatly depending on the type of plant, and therefore can be increased by improving the plant type via regulation of GA signaling. However, to date, it is unknown of how plants perceive GA, how the GA signal is transmitted, and how plant growth is induced by GA regulation. Recently, the present inventors have isolated two types of GA-signaling mutants in rice. One is a constitutive GA response mutant, slender rice1 (slr1) (Non-patent Documents 2 and 3); the other is a GA-insensitive dwarf mutant, GA-insensitive dwarf2 (gid2) (Non-patent Document 4). The SLR1 gene encodes a protein predicted to be a transcription factor orthologous to *Arabidopsis* GAI (Non-patent Document 5) and RGA (Non-patent Document 6), wheat Rht, maize d8, and barley SLN1 (Non-patent Document 7). All these proteins, including and mentioned after *Arabidopsis* GAI above, are grouped into the DELLA subfamily of the GRAS family (Non-patent Document 8). The GID2 gene encodes a protein that is predicted to be the F-box subunit of SCF E3 ubiquitin ligase, which is orthologous to *Arabidopsis* SLY (Non-patent Document 9). Analyses of these mutants have predicted that the rice SLR1 protein, a GA-signaling repressor, is degraded via the SCF$^{GID2}$-proteosome pathway that induces the actions downstream of GA (Non-patent Document 8). However, far less is known about the process of GA perception as compared to the process regulated by DELLA proteins. To date, there are several reports on GA-binding proteins studied by biochemical approaches (Non-patent Documents 10 and 11). However, as yet, no proteins have been identified that directly participate in GA perception.

Non-patent Document 1: Davies, P. J., Plant Hormones (Kluwer Academic, Dordrecht, Netherlands, 1995).
Non-patent Document 2: Ikeda, A. et al., Plant Cell. 13, 999-1010 (2001)
Non-patent Document 3: Itoh, H. et al., Plant Cell 14, 57-70 (2002)
Non-patent Document 4: Sasaki, A. et al., Science 299, 1896-1898 (2003)
Non-patent Document 5: Peng, J. et al., Genes Dev. 11, 3194-3205 (1997)
Non-patent Document 6: Silverstone, A. L. et al., Plant Cell 2, 155-169 (1998)
Non-patent Document 7: Gubler, F. et al., Plant Physiol. 129, 191-200 (2002)
Non-patent Document 8: Itoh, H. et al., Trends Plant Sci. 8, 492-497 (2003)
Non-patent Document 9: McGinnis, K. M. et al., Plant Cell. 15, 1120-1130 (2003)
Non-patent Document 10: Lovegrove, A. et al., Plant J. 15, 311-320 (1998)
Non-patent Document 11: Nakajima, M. et al., Biochem. Biophys. Res. Comm. 241, 782-786 (1997)

DISCLOSURE OF THE INVENTION

Problems to be Solved by the Invention

The present invention provides gibberellin-binding proteins involved in GA signaling and genes encoding same. The present invention also provides methods for regulating plant differentiation and growth using such genes.

Means for Solving the Problems

GA is hydrophobic and weakly acidic. Due to these biochemical properties, GA is present in the form of soluble acid salt in the plant cells and at the intercellular spaces. Alternatively, GA can also take the form of free acid, and thus permeate through biological membrane via passive diffusion (Hooley, R. et al., Biochem. Soc. Trans. 85-89 (1992)). It has been hypothesized that there are two types of GA receptors: membrane-bound and cytoplasmic types (Hooley, R. et al., Biochem. Soc. Trans. 85-89 (1992)). However, neither of these GA receptors have been identified. Meanwhile, the present inventors successfully isolated multiple GA-insensitive dwarf mutants (GA insensitive dwarf mutant) in rice. To identify the causative genes of the mutants, the inventors specified the position of mutation by positional cloning. As a result, the inventors successfully identified the causative gene of the GA insensitive dwarf mutation (GA insensitive dwarf mutant-1; GID1). Analysis of this gene revealed that the GID1 gene encodes an unknown protein similar to the hormone-sensitive lipase (HSL) family. The recombinant GID1 protein demonstrated a high affinity for biologically active GAs, such as $GA_4$, $GA_1$, and $GA_3$, but not for biologically inactive GAs, such as $GA_9$, $GA_{51}$, and 3-epi-$GA_4$. In addition, mutant GID1 proteins having a mutation corresponding to each of the three gid1 alleles demonstrated no affinity for GAs. Furthermore, the $K_d$ value of GID1 against $GA_4$ was on the order of $10^{-7}$ M, which was sufficient to explain the resulting shoot elongation. The association/dissociation rates of $GA_4$ for GID1 were also found to be very high. Furthermore, a GID1 overproducing line expressed a GA-hypersensitive phenotype. Based on these findings, GID1 protein was determined to be a cytoplasmic receptor that mediates GA signaling. The gibberellin-binding protein genes provided by the present invention are very useful in increasing the gibberellin sensitivity to enhance plant growth. Furthermore, when tall crop plants, such as grain crops, are modified into dwarf types by suppressing the expression of the proteins, the lodging of the plants can be reduced to improve the yield. Furthermore, the proteins of the present invention can be used to assess binding to biologically active gibberellins. Screening and testing for compounds that regulate the actions of gibberellins on plants can be achieved by using the proteins of the present invention.

Specifically, the present invention relates to gibberellin-binding proteins, genes thereof, and uses thereof. More specifically, the present invention relates to each of the inventions set forth in the claims. Inventions that include one or more combinations of the inventions set forth in claims that cite an identical claim are intended to be included in the inventions of the claims. Specifically, the present invention relates to:

[1] the protein of any one of:
(a) a protein comprising the amino acid sequence of SEQ ID NOs: 2, 5, 7, or 9;
(b) a protein comprising an amino acid sequence with a substitution, deletion, and/or insertion of one or more amino acids in the amino acid sequence of SEQ ID NOs: 2, 5, 7, or 9, which has the activity of binding to gibberellin;
(c) a protein encoded by a nucleic acid that hybridizes under a stringent condition to a probe prepared from a nucleic acid comprising the nucleotide sequence of SEQ ID NOs: 1, 4, 6, or 8 and/or a sequence complementary thereto, which has the activity of binding to gibberellin;
[2] the protein of [1], which is any one of:
(a) a protein comprising the amino acid sequence of SEQ ID NO: 2;
(b) a protein comprising an amino acid sequence with a substitution, deletion, and/or insertion of one or more amino acids in the amino acid sequence of SEQ ID NO: 2, which has the activity of binding to gibberellin;
(c) a protein encoded by a nucleic acid that hybridizes under a stringent condition to a probe prepared from a nucleic acid comprising the nucleotide sequence of SEQ ID NO: 1 and/or a sequence complementary thereto, which has the activity of binding to gibberellin;
[3] the protein of [1] or [2] comprising the amino acid sequence of SEQ ID NOs: 2, 5, 7, or 9;
[4] the protein of [2] comprising the amino acid sequence of SEQ ID NOs: 2;
[5] the protein of any one of [1] to [4], which is a protein of a monocotyledonous plant;
[6] a nucleic acid encoding the protein of any one of [1] to [5];
[7] a vector carrying the nucleic acid of [6];
[8] a transformed cell having the nucleic acid of [6] introduced therein;
[9] the transformed cell of [8], which is a plant cell with enhanced gibberellin sensitivity;
[10] a transformant plant introduced with the nucleic acid of [6], which is a plant with enhanced gibberellin sensitivity;
[11] the transformant plant of [10], which is a monocotyledonous plant;
[12] a breeding material of the transformant plant of [10] or [11];
[13] a polypeptide comprising an antibody that binds to the protein of any one of [1] to [5] or a polypeptide comprising an antigen-binding fragment thereof;
[14] an expression vector for a nucleic acid that suppresses the expression of any one of the protein of [1] to [5];
[15] a transformed cell introduced with the vector of [14];
[16] the transformed cell of [15], which is a plant cell with reduced gibberellin sensitivity;
[17] a transformant plant introduced with the vector of [14], which is a plant with reduced gibberellin sensitivity;
[18] the transformant plant of [17], which is a monocotyledonous plant;
[19] a breeding material of the transformant plant of [17] or [18];
[20] a method for enhancing or reducing gibberellin sensitivity, which comprises the step of either increasing or decreasing the expression of any one of the protein of [1] to [5];
[21] a method for producing a plant hyper- or hypo-sensitivity to gibberellin, which comprises the step of regenerating a plant from a plant cell in which the expression of any one of the protein of [1] to [5] is increased or decreased;
[22] a method for assaying a response to gibberellin, which comprises the steps of: contacting gibberellin with a plant cell or a plant in which the expression of the protein of any one of [1] to [5] is increased or decreased, and detecting a response of the cell or plant to gibberellin;
[23] a method for assaying a response to gibberellin, which comprises the steps of: contacting a test compound with a plant cell or a plant in which the expression of the protein of any one of [1] to [5] is increased or decreased, and detecting a response of the cell or plant to gibberellin;
[24] the method of [23], which further comprises the step of contacting gibberellin;
[25] a method for selecting a compound that regulates gibberellin response, which comprises the steps of:
(a) contacting a test compound with a plant cell or a plant in which the expression of the protein of any one of [1] to [5] is increased or decreased;
(b) detecting a response of the cell or plant to gibberellin; and
(c) selecting a compound that increases or decreases gibberellin response;
[26] the method of [25], wherein step (a) is conducted in the presence of gibberellin;
[27] a method for binding the protein of any one of [1] to [5] with gibberellin, which comprises the step of contacting the protein with gibberellin;
[28] a method for detecting gibberellin binding, which comprises the steps of: contacting the protein of any one of [1] to [5] with gibberellin and detecting the binding between the protein and gibberellin;
[29] a method for assaying a compound that regulates the interaction between gibberellin and the protein of any one of [1] to [5], which comprises the steps of:
(a) contacting a test compound, gibberellin, and the protein together; and
(b) detecting the binding between gibberellin and the protein;
[30] a method for selecting a compound that inhibits the interaction between gibberellin and the protein of any one of [1] to [5], which comprises the steps of:
(a) contacting a test compound, gibberellin, and the protein together;
(b) detecting the binding between gibberellin and the protein; and
(c) selecting a compound that inhibits the binding;
[31] a method for binding the protein of any one of [1] to [5] with a DELLA protein, which comprises the step of contacting the proteins;
[32] a complex comprising the protein of any one of [1] to [5] and gibberellin;
[33] a complex comprising the protein of any one of [1] to [5] and a DELLA protein; and
[34] the complex of [32], which further comprises a DELLA protein.

BRIEF DESCRIPTION OF THE DRAWINGS

FIG. 2 is a diagram showing the genomic organization of the GID1 gene. Panel a) demonstrates that gid1 is mapped in an interval of about 38 kb between the molecular markers c56-10 and c57 in an about 80-cM region of rice chromosome 5. Panel b) depicts mutation sites and mutations of four gid1 mutants.

FIG. 3 is a diagram showing the structure of GID1. Panel a) depicts the amino acid sequence of GID1. Positions of the mutations in gid1-1, gid1-2, and gid1-3 are shown. Panel b) is an amino acid sequence comparison between GID1 and the consensus sequence (SEQ ID NO: 3) of the HSL group in the database of NCBI Conserved Domain Search. Closed circle represents the region conserved in the HSL family. Numerical values represent the position from the first methionine in each sequence. Panel c) depicts the results of confocal micrographs of GFP fluorescence in pieces of young leaves of transgenic rice plant carrying Act1 promoter-GID1-GFP. The plants were treated with $10^{-6}$ M uniconazol (+uni) or $10^{-5}$ M $GA_3$ (+$GA_3$) for 1 week. Left panel, DAPI staining of the sample shown in the middle panel.

FIG. 5 presents the amino acid sequences of *Arabidopsis* GID1 (AtGID1) and rice GID1 (OsGID1). An alignment of three AtGID1s and related proteins. The sequences of AtGID1a (SEQ ID NO: 5), AtGID1b (SEQ ID NO: 7), and AtGID1c (SEQ ID NO: 9) were compared with that of OsGID (SEQ ID NO: 2). ClustalW program (Thompson J D et al. (1994) Nucleic Acids Res. 22:4673-80; Chenna R et al. (2003) Nucleic Acids Res. 31:3497-500; the webpage for ClustalW of DNA Data Bank of Japan (DDBJ); was used for the alignment. Seven clones that are orthologous to OsGID1, which were ranked from the 4$^{th}$ to the 10$^{th}$ in a BLAST search, were named "D" to "J" in this order. The clones are shown in the list using a letter combined with an ORF name from the AGI group annotation (AGI code). The dotted two amino acids correspond to Gly-196 and Arg-251 essential for the GA-binding activity of OsGID1; in rice gid1-1 and gid1-2 mutants, the amino acids have been substituted by other amino acid residues. Arrows indicate the three catalytic centers (Ser (S), Asp (D), and His (H)) of hormone-sensitive lipase.

FIG. 12 depicts the expression of AtGID1 in the rice gid1-1 transformant and organ specificity in *Arabidopsis*. Panel A) depicts the gross morphologies of transformants expressing pAct1-AtGID1a (a1 and a2), pAct1-AtGID1b (b1 and b2), or pAct1-AtGID1c (c1 and c2). The gid1-1 plant overexpressing the AtGID1 gene (pAct1-AtGID1) under the control of rice Actin1 promoter is shown along with the parental mutant (gid1-1) and wild-type plant (T65). The Bar indicates 5 cm. Panel B) depicts the detection of AtGID1 mRNA in transformants by RT-PCR. About 200 mg of total RNA was obtained from leaf blades of each transformants. The number of PCR cycles was 25 (AtGID1) or 22 (OsActin). Panel C) depicts the distribution of AtGID1 expressing organs in *Arabidopsis*. F, flower; Si, silique; St, stem; L, leaf; R, root; and S, imbibed seed. The number of PCR cycles was 31 (AtGID1) or 22 (AtActin).

BEST MODE FOR CARRYING OUT THE INVENTION

Figure 1:
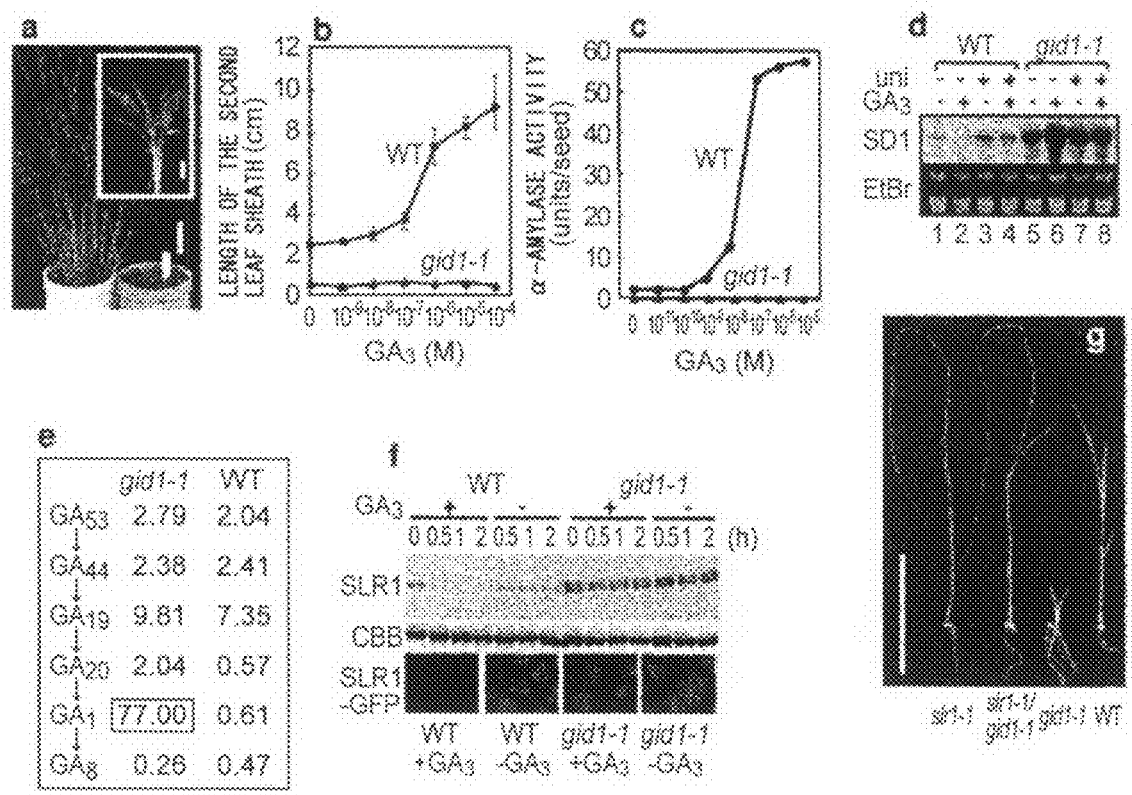
FIG. 1 is composed of graphs and photographs demonstrating the GA-insensitive phenotypes of gid1. Panel a) depicts gross morphologies of the wild-type plant (left) and gid1-1 plant (right) three months after seeding (bar=10 cm). The inset is a photograph of enlarged image of gid1-1 four weeks after seeding (bar=1 cm). Panel b) depicts the elongation of the second leaf sheath of the wild type (closed circle) and gid1-1 (closed triangle) in response to $GA_3$ treatment. Bar represents standard deviation (n=10). Panel c) depicts the induction of α-amylase activity in embryoless half seeds of the wild type (closed circle) and gid1-1 (closed triangle) in response to $GA_3$ treatment. Of the triplicated experiments, representative data was shown. Panel d) depicts the results of RNA gel blot analysis for SD1/OsGA20ox. Total RNAs were extracted from wild-type and gid1 seedlings grown in the presence (3, 4, 7, and 8) or absence (1, 2, 5, and 6) of $10^{-6}$ M uniconazol (uni), an inhibitor of GA biosynthesis, for two weeks and treated in the presence (2, 4, 6, and 8) or absence (1, 3, 5, and 7) of $10^{-5}$ M $GA_3$. The gel was stained with ethidium bromide (EtBr) as a loading control. Panel e) depicts the metabolic pathway of rice GA and the GA level (ng/g fresh weight) in gid1-1 and the wild type. Of the triplicated experiments, a representative set of data was shown. Panel f) depicts the loss of GA-induced degradation of SLR1 in gid1-1. Upper panel, protein gel blot analysis of SLR1 protein. gid1-1 and wild-type seedlings two weeks after seeding were grown in the presence of $10^{-6}$ M uniconazol, and treated with $10^{-4}$ M $GA_3$ for each period indicated in the figure. Ten µg of total protein was loaded onto each lane. Middle panel, Coomassie brilliant blue (CBB) stain for loading control. Bottom panel, confocal micrographs of GFP fluorescence in pieces of young leaves of transgenic wild-type plants and gid1-1 plants carrying SLR1 promoter-SLR1-GFP. The plants were grown in the presence of $10^{-6}$ M uniconazol and treated in the presence (+) or absence (−) of $10^{-4}$ M $GA_3$ for 12 hours. Panel g) depicts the results of epistatic analysis of gid1 and slr1 mutations. Gross morphologies of slr1-1 single mutant, slr1/gid1 double mutant, and gid1-1 single mutant plants, whose genotypes were identified based on the sequence of each gene, and the wild-type plant (bar=10 cm). The slr1-1/gid1-1 double mutant exhibited the slr1-1 phenotype. This was confirmed based on the segregation ratio of F2 plants (total=844) [segregation of each phenotypes was: 200 (slr1-1), 493 (WT), or 151 (gid1-1), which corresponds to 4:9:3 ($\chi^2$=0.124, p=0.940)].

The present invention provides gibberellin-binding proteins and nucleic acids encoding the proteins. The nucleic acids may be DNAs or RNAs, and their forms are not particularly limited. Specifically, the nucleic acids may be genomic DNAs, synthetic DNAs, mRNAs, or the like, and may be single-stranded or double-stranded. The nucleic acids may be circular or linear. In context of the present invention, the term "proteins" is not limited to full length protein chains but also includes short peptide chains referred to as "oligopeptides". The term "proteins" also encompasses polypeptides. Furthermore, the proteins and genes of the present invention include isolated and recombinant proteins and genes. The term "isolated proteins and genes" refers to proteins and genes isolated from the natural state, and encompasses purified and artificially produced proteins and genes. The term "recombinant" refers to proteins and genes produced or replicated via genetic recombination or synthesis. The term "recombinant nucleic acids" refers to nucleic acids in which nucleotides are not linked at one end or both ends as in the natural state. Recombinant nucleic acids include synthetic nucleic acids, and nucleic acids cloned in plasmids or other vectors. Recombinant nucleic acids can be produced by cleaving natural nucleic acids with nucleases, sonication, or such, and linking them again with ligase or such. Herein, synthetic nucleic acids and nucleic acids amplified with plasmids or phages or by PCR and such are also encompassed by the recombinant nucleic acids of the present invention. Alternatively, when the recombinant is a protein, the term "recombinant protein" encompasses both synthetic proteins and proteins expressed from recombinant nucleic acids.

Genomic DNAs and cDNAs can be prepared by methods known to those skilled in the art. For example, genomic DNAs can be obtained by screening constructed genomic libraries using genomic DNAs prepared from desired plants. Likewise, cDNAs can be obtained by preparing cDNA libraries using cDNAs that result from the reverse transcription of mRNAs which was prepared from the desired plants, and by screening the libraries. Screening probes may be appropriately prepared; for example, labeled probes may be prepared based on the nucleotide sequence of SEQ ID NOs: 1, 4, 6, or 8. Alternatively, DNAs of interest can be amplified by PCR using cDNAs or genomic DNAs as templates. Alternatively, the DNAs of interest can also be prepared using commercially available DNA synthesizers.

Proteins of the present invention include proteins having the amino acid sequence of SEQ ID NOs: 2, 5, 7, or 9, and proteins that are functionally equivalent thereto. The term "functionally equivalent" refers to the presence of gibberellin-binding activity. Specifically, the proteins of the present invention have a binding activity to at least one of the biologically active gibberellins. Biologically active gibberellins include $GA_4$, 16,17-dihydro$GA_4$, $GA_1$, $GA_3$, $GA_{35}$, and $GA_{37}$. The proteins of the present invention preferably have a binding activity against one (for example, $GA_4$) or more gibberellins, more preferably two or more gibberellins, even more preferably three or more gibberellins selected from $GA_4$, 16,17-dihydro$GA_4$, $GA_1$, and $GA_3$, and still more preferably to all four gibberellins. More preferably, the proteins of the present invention bind specifically to biologically active gibberellins. Specifically, it is preferable that the affinity of the proteins of the present invention for inactive gibberellins ($GA_4$ methyl ester, 3-epi-$GA_4$, $GA_9$, and $GA_{51}$) be significantly lower than that for at least one of the biologically active gibberellins (for example, $GA_4$, 16,17-dihydro$GA_4$, $GA_1$, and $GA_3$). The binding affinity is determined, for example, by determining the $K_d$ value. Herein, the term "gibberellins" refers to biologically active gibberellins unless otherwise specified.

The ability of a protein of the present invention to bind to gibberellin can be assayed, for example, by incubating a labeled gibberellin with a protein dissolved in a binding buffer [20 mM Tris-HCl (pH 7.6), 5 mM 2-mercaptoethanol, and 0.1 M NaCl]. The binding between the two can be measured by quantifying the gibberellin bound to the column (Nakajima, M. et al., Biochem. Biophys. Res. Comm. 241, 782-786 (1997)). Specifically, the binding to gibberellin of the proteins can be assessed according to the methods described in the Examples.

The origin of the proteins and nucleic acids of the present invention is not particularly limited. For example, the plant species from which the proteins and the nucleic acids of the present invention are derived may include monocotyledonous or dicotyledonous plants. In a preferred embodiment, the species is a monocotyledonous plant, more preferably a plant of the Gramineae family including barley, wheat, and rice, and most preferably rice. Examples of dicotyledonous plants include *Arabidopsis*. In the above description, the term "origin" means that the proteins and nucleic acids either: (i) have the same structure as those obtained from a particular plant; (ii) result from the modification of (i); or (iii) are produced based on the modified information from the structural (sequence) information of (i). For example, nucleic acids and proteins derived from natural genes and proteins have been routinely prepared by modifying natural genes to insert restriction enzyme recognition sequences or adding tag peptides to prepare fusion proteins, without losing their activities (Sambrook, J. and D W Russell, 2001, Molecular Cloning, A Laboratory Manual, Third Edition, Cold Spring Harbor Laboratory Press, Cold Spring Harbor, N.Y.). Such modified forms (and, analogs and derivatives) are included in the proteins and nucleic acids of the present invention. Specifically, the present invention also relates to proteins having gibberellin-binding activity as well as a sequence that is highly homologous to but excludes SEQ ID NOs: 2, 5, 7, or 9.

Furthermore, the proteins of the present invention also include other plant homologs (counterparts) of rice and *Arabidopsis* gibberellin-binding (GID1) proteins, in addition to the polymorphic forms and variants of rice and *Arabidopsis* GID1 protein described in the Examples. Hybridization techniques (Southern E M: J. Mol. Biol. 98: 503, 1975) and polymerase chain reaction (PCR) techniques (Saiki R K, et al: Science 230: 1350, 1985; Saiki R K, et al: Science 239: 487, 1988) can be used to isolate nucleic acids encoding homologous proteins from the same or different plant species. For example, nucleic acids encoding the proteins of the present invention can be isolated by hybridization using a nucleic acid having the nucleotide sequence of SEQ ID NOs: 1, 4, 6, or 8, a sequence complementary thereto, or a portion thereof. Specifically, when probes are prepared based on the nucleotide sequence of SEQ ID NOs: 1, 4, 6, or 8, or the complementary sequence thereof, or a portion thereof, nucleic acids that hybridize to the probes under stringent conditions can be isolated from rice and other plants. Alternatively, when primers are prepared based on the nucleotide sequence of SEQ ID NOs: 1, 4, 6, or 8, or the complementary sequence thereof, nucleic acids encoding a protein of interest can be amplified by PCR from rice and other plants. Such proteins include, for example, proteins identified by the AGI codes (The *Arabidopsis* Genome Initiative gene code): At3g05120 (AtGID1a; SEQ ID NOs: 4 and 5), At3g63010 (AtGID1b; SEQ ID NOs: 6 and 7), and At5g27320 (AtGID1c; SEQ ID NOs: 8 and 9). The structures of these proteins and genes can also be found at the public database MATDB of MIPS (Munich information center for Protein Sequences) or by searching the webpage of the National Center for Biotechnology Information (NCBI).

Whether nucleic acids hybridize with each other can be assayed, for example, by preparing a probe either from a nucleic acid having the nucleotide sequence of SEQ ID NOs: 1, 4, 6, or 8, or the complementary sequence thereof, or a nucleic acid targeted in the hybridization, and then detecting whether this probe hybridizes to the other DNA. The probe may be labeled by random priming (Sambrook, J. and D W Russell, 2001, Molecular Cloning, A Laboratory Manual, Third Edition, Cold Spring Harbor Laboratory Press, Cold Spring Harbor, N.Y.; Random Primer DNA Labeling Kit Ver. 2.0 (Takara, Otsu, Japan)). Those skilled in the art can select the appropriate stringent conditions. Examples of stringent conditions include, for example, hybridization at 48° C., preferably at 52° C., and more preferably at 60° C. in a solution containing 5×SSC (1×SSC containing 150 mM NaCl and 15 mM sodium citrate), 7% (W/V) SDS, 100 μg/ml denatured salmon sperm DNA, 5×Denhardt's solution (1×Denhardt's solution containing 0.2% polyvinylpyrrolidone, 0.2% bovine serum albumin, and 0.2% Ficoll), and washed for 2 hours while shaking in 2×SSC at the same temperature as the hybridization, more preferably at 60° C., and even more preferably at 65° C. The washing is more preferably carried out using 1×SSC, even more preferably 0.5×SSC, and still more preferably using 0.1×SSC (Sambrook, J. and D W Russell, 2001, Molecular Cloning, A Laboratory Manual, Third Edition, Cold Spring Harbor Laboratory Press, Cold Spring Harbor, N.Y.).

The proteins of the present invention and nucleic acids encoding the same possess sequences that are highly homologous to the amino acid sequences of SEQ ID NOs: 2, 5, 7, or 9 and the nucleotide sequences of CDS of SEQ ID NOs: 1, 4, 6, or 8, respectively. A high homology refers to a sequence having an identity of 60% or higher, preferably 65% or higher, more preferably 70% or higher, even more preferably 75% or higher, 80% or higher, 85% or higher, 90% or higher, and yet more preferably 95% or higher. The sequence identity can be determined, for example, using the BLAST program (Altschul, S. F. et al., 1990, J. Mol. Biol. 215: 403-410). Specifically, the blastn program may be used to determine nucleotide sequence identity, while the blastp program may be used to determine amino acid sequence identity. For example, at the BLAST web page of NCBI (National Center for Biotechnology Information), computation may be carried out by setting all filters, such as "Low complexity", to "OFF" and then using the default parameters (Altschul, S. F. et al. (1993) Nature Genet. 3:266-272; Madden, T. L. et al. (1996) Meth. Enzymol. 266:131-141; Altschul, S. F. et al. (1997) Nucleic Acids Res. 25: 3389-3402; Zhang, J. & Madden, T. L. (1997) Genome Res. 7:649-656). The parameters may be set, for example, as follows: open gap cost is set as 5 for nucleotides and 11 for proteins; extend gap cost is set as 2 for nucleotides and 1 for proteins; nucleotide mismatch penalty is set as −3; reward for a nucleotide match is set as 1; expect value is set as 10; the wordsize is set as 11 for nucleotides and 2 for proteins; Dropoff (X) for blast extensions in bits is set as 20 in blastn and 7 in other programs; X dropoff value for gapped alignment (in bits) is set as 15 in programs other than blastn; and final X dropoff value for gapped alignment (in bits) is set as 50 in blastn and 25 in other programs. In amino acid sequence comparison, BLOSUM62 can be used as a scoring matrix (Henikoff, S, and Henikoff, J. G. (1992) Proc. Natl. Acad. Sci. USA 89: 10915-10919). The blast2sequences program (Tatiana A et al. (1999) FEMS Microbiol Lett. 174:247-250), which compares two sequences, can be used to prepare an alignment of two sequences and to determine their sequence identity. The identity for the coding sequence (CDS) of SEQ ID NOs: 1, 4, 6, or 8, or SEQ ID NOs: 2, 5, 7, or 9 was calculated by treating gaps as mismatches and neglecting gaps outside the CDS.

The proteins of the present invention also include proteins having an amino acid sequence that includes the substitution, deletion, and/or insertion of one or more amino acids in the amino acid sequence of SEQ ID NOs: 2, 5, 7, or 9. Methods for preparing nucleic acids encoding a protein having a modified amino acid sequence, which are well known to those skilled in the art, include site-directed mutagenesis (Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766). Mutations in protein amino acid sequences may also occur in nature, arising from mutations in the nucleotide sequences that encode the proteins. Accordingly, the present invention includes proteins having a gibberellin-binding activity as well as an amino acid sequence with a substitution, deletion, addition, and/or insertion of one or more amino acids in the amino acid sequence encoding a naturally occurring gibberellin-binding protein (for example, SEQ ID NOs: 2, 5, 7, or 9). Modification of few amino acids is unlikely to affect the protein activity (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413; Bowie et al., Science (1990) 247, 1306-1310). The number of amino acids to be modified is typically 50 amino acids or less, preferably 30 amino acids or less, more preferably 25 amino acids or less, 20 amino acids or less, 15 amino acids or less, or 10 amino acids or less (for example, 5 amino acids or less, or 3 amino acids or less).

The amino acid residue to be mutated is preferably substituted with another amino acid that allows for conservation of the amino acid side-chain properties. Such substitutions are referred to as conserved amino acid substitutions. Amino acid groups that may be substituted within the same group for conserved substitution include: hydrophobic amino acids (A, I, L, M, F, P, W, Y, and V), hydrophilic amino acids (R, D, N, C, E, Q, C; H, K, S, and T), and amino acids having the following side chains: aliphatic side chains (C; A, V, L, I, and P); hydroxyl group-containing side chains (S, T, and Y); sulfur atom-containing side chains (C and M); carboxylic acid- and amide-containing side chains (D, N, E, and Q); basic side chains (R, K, and H); and aromatic ring-containing side chains (H, F, Y, and W) (the letters in the parenthesis indicate the one-letter amino acid codes). The hydropathic index (Kyte and Doolittle, J Mol. Biol. May 5, 1982; 157(1): 105-32) and hydrophilicity value (U.S. Pat. No. 4,554,101) for each amino acid before and after modification are preferably within ±2, more preferably within ±1, and even more preferably within ±0.5.

When the amino acid sequence of SEQ ID NOs: 2, 5, 7, or 9 is modified, the HGG motif (from position 120 to 122 in SEQ ID NO: 2) and the GXSXG motif (from position 196 to 200 in SEQ ID NO: 2), both which are consensus sequences of the hormone-sensitive lipase (HSL) family, should be preserved (Osterlund, T. et al., Biochem. J. 319, 411-420 (1996); Manco, G. et al., Arch. Biochem. Biophys. 373, 182-192 (2000)). In addition, the modified sequence preferably includes the amino acid sequence of the region from position 70 to 119 in SEQ ID NO: 2 or the regions corresponding thereto in SEQ ID NOs: 5, 7, or 9 (see FIG. 5). More preferably, the modified sequence includes the amino acid sequence of the region from position 148 to 160, and from 258 to 331 in SEQ ID NO: 2, or the regions corresponding thereto in SEQ ID NOs: 5, 7, or 9. Such preferred proteins include, for example, proteins including the amino acid sequence of the region from position 70 to 350 of SEQ ID NO: 2, or the regions corresponding thereto in SEQ ID NOs: 5, 7, or 9. When proteins other than the proteins of SEQ ID NOs: 2, 5, 7, and 9 are modified, it is preferable that the amino acid sequences first be aligned with these sequences and then be modified, so as to ensure that the regions corresponding to the regions described above are preserved. Such alignments may be prepared, for example, using BLAST 2 SEQUENCES (Tatiana A. et al., 1999, FEMS Microbiol Lett. 174:247-250), ClustalW program (Thompson J D et al. (1994) Nucleic Acids Res. 22:4673-80; Chema R et al. (2003) Nucleic Acids Res. 31:3497-500), and the like.

The screening of a plant cDNA library for nucleic acids encoding the proteins of the present invention may be performed, for example, by screening known expression libraries. The sequences of about 70 amino acids at the N terminus of *Arabidopsis* and rice GID1 are highly conserved and specific to gibberellin-binding proteins. Accordingly, an antibody that binds to any of the positions in this region can be used. Therefore, the proteins of the present invention can be isolated by screening genes encoding proteins to which this antibody binds. Preferred antibodies are those that bind to any of the amino acid regions from position 1 to 70, preferably from position 1 to 60, more preferably from position 1 to 50, and even more preferably from position 1 to 40 of *Arabidopsis* or rice GID1 (SEQ ID NOs: 2, 5, 7, or 9). Alternatively, the amino acids from position 250 to 289 of rice GID1 are also both highly conserved and gibberellin specific. Thus, antibodies that bind to any of the positions in this region may also be preferably used. For example, screening can be performed using an antibody that binds to any of the amino acid regions from position 250 to 289 of rice GID1 (SEQ ID NO: 2), preferably from position 250 to 280, more preferably from position 280 to 270, even more preferably from position 280 to 265, and still more preferably from position 280 to 260, or to any of the positions corresponding to these amino acid regions of *Arabidopsis* GID1 (see FIG. 5). The present invention includes proteins to which any of the antibodies described above bind to and which, in turn, bind to gibberellin.

Furthermore, such proteins may be made into fusion proteins by appropriately fusing with other proteins. Fusion proteins can be prepared by linking DNAs encoding target proteins in frame, inserting the linked sequence into an expression vector, and expressing it in hosts. The proteins to be fused are not particularly limited and include, for example, marker proteins and tag peptides. The proteins having the amino acid sequence of SEQ ID NOs: 2, 5, 7, or 9 of the present invention include proteins having a sequence that includes an additional amino acid sequence constituting desired proteins, such as tags and other proteins, at one or both ends of the amino acid sequence of SEQ ID NOs: 2, 5, 7, or 9.

Proteins to be fused with the proteins of the present invention include, for example, known tag peptides, such as FLAG (Hopp, T. P. et al., BioTechnology (1988) 6, 1204-1210), 6×His, which includes six histidine (His) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, and Protein C fragment. The length of polypeptide to be added may be, for example, 50 amino acids or less, preferably 30 amino acids or less, 25 amino acids or less, 20 amino acids or less, 15 amino acids or less, or 10 amino acids or less. Other proteins to be fused also include, for example, glutathione S-transferase (GST), influenza hemagglutinin (HA), immunoglobulin constant region, β-galactosidase, and maltose-binding protein (MBP). Fusion proteins with GST or MBP are often used to collect in vitro expressed proteins (Guan, C. et al. (1987) Gene, 67, 21-30; Maina, C. V. et al. (1988) Gene, 74, 365-373; Riggs, P. D. (1990) In Expression and Purification of Maltose-Binding Protein Fusions. F. M. Ausebel, R. Brent, R. E. Kingston, D. D. Moore, J. G. Seidman, J. A. Smith and K. Struhl (Eds.), Current Protocols in Molecular Biology, pp. 16.6.1-16.6.10; Bar-Peled and Raikhel (1996) Anal. Biochem. 241:140-142; Brew K, et al. (1975) JBC 250(4):1434-44; H. Youssoufian, (1998) BioTechniques 24(2):198-202). When fusion proteins are designed to have a peptidase cleavage sequence at the boundary, the proteins of interest alone can be collected by cleaving off the GST or MBP moiety after purification.

The present invention also relates to a vector carrying an inserted nucleic acid which encodes a gibberellin-binding protein of the present invention. Such vectors are not particularly limited and include, for example, plasmids, viral vectors, phages, cosmids, YAC (yeast artificial chromosome), BAC (bacterial artificial chromosome), PAC (P1-derived artificial chromosome), and TAC (transformation-competent artificial chromosome). The vectors of the present invention include the coding sequence of a protein described above, and/or a sequence complementary thereto. For example, when the vector is a double-stranded DNA vector, such as a plasmid vector, it may carry the coding sequence of a protein of the present invention and a sequence complementary thereto. When the vector is a viral vector including a single-stranded genome or such, for example, a virus having the plus-strand genome, it may contain the coding sequence of a protein of the present invention, and, in case of a virus having the minus-strand genome, it can contain a complementary sequence therefor. Preferred vectors of the present invention include expression vectors expressing a protein of the present invention. Such expression vectors are useful in recombinant protein production and transformation.

Recombinant proteins can be produced by introducing an above-described expression vector into cells and collecting the expressed proteins. Host cells are not particularly limited, so long as they are suitable to express recombinant proteins; bacteria, such as Escherichia coli, yeast, various animal and plant cells (including insect cells), and the like can be used. Vectors can be introduced into host cells by various methods known to those skilled in the art. For example, the introduction into E. coli can be achieved by the calcium method or electroporation (Mandel, M. & Higa, A., Journal of Molecular Biology, 1970, 53, 158-162; Hanahan, D., Journal of Molecular Biology, 1983, 166, 557-580); when the host is yeast, the lithium acetate method (BD Yeastmaker Yeast Transformation System 2, BD Bioscience/Clontech) may be used; when the host is higher eukaryotic cells, various types of transfection reagents (TransIT® Transfection Reagents, Mirus Bio Corporation) and the like may be used. Recombinant proteins expressed in host cells can be collected and purified from the host cells or culture supernatants thereof using methods known to those skilled in the art. As described above, recombinant proteins may be expressed as proteins fused with other proteins. Such proteins can be produced, for example, as fusion proteins with maltose-binding protein (pMAL series; New England BioLabs), fusion proteins with glutathione S-transferase (GST) (pGEX series; Amersham Pharmacia Biotech), or proteins with an addition of histidine tag (pET series; Novagen), when E. coli is used as the host. When recombinant proteins are expressed as fusion proteins with maltose-binding protein, affinity purification can be readily carried out using an amylose column or the like. When recombinant proteins are expressed as a fusion protein with GST, the proteins can be collected and purified using a glutathione column. Proteins having an additional His tag can be collected and purified using a nickel column.

The present invention also relates to antibodies that bind to the gibberellin-binding proteins of the present invention. Antibodies that bind specifically to the proteins of the present invention can be prepared using as antigens the proteins of the present invention or partial peptides thereof. Polyclonal antibodies can be prepared, for example, from sera after removal of blood clots, collected from the blood of animals, such as rabbits, after a certain period of time subsequent to immunization with a purified protein of the present invention or a partial peptide thereof. Alternatively, monoclonal antibodies can be prepared by fusing myeloma cells with antibody-producing cells of animals immunized with a protein or peptide described above, isolating the monoclonal cells (hybridomas) that produce the antibody of interest, and preparing the antibody from the cells (Antibodies: A Laboratory Manual, E. Harlow and D. Lane, ed., Cold Spring Harbor Laboratory (Cold Spring Harbor, N.Y., 1988)). The resulting antibodies can be used to purify or detect the protein of the present invention, or for other purposes. The antibodies of the present invention include polyclonal and monoclonal antibodies, and polypeptides including the antigen-binding sites of these antibodies (including Fab, Fab', F(ab')2, Fv, and single-chain Fv (scFv)). The present invention also relates to compositions containing the antibodies described above, such as antisera.

The first 70 N terminus amino acids of Arabidopsis and rice GID1 are highly conserved and specific to gibberellin-binding proteins. Thus, antibodies that bind to any position within this region are expected to have particularly outstanding characteristics. Alternatively, the amino acids extending from position 250 to 289 of rice GID1 are also both highly conserved and gibberellin specific, and thus, antibodies that bind to any position within this region corresponding to that of rice or Arabidopsis also are expected to have particularly outstanding characteristics. Specifically, for example, the antibodies of the present invention are preferably antibodies that bind to any position within the amino acid region from position 1 to 70, preferably from position 1 to 60, more preferably from position 1 to 50, even more preferably from position 1 to 40 of Arabidopsis or rice GID1 (SEQ ID NOs: 2, 5, 7, or 9);

and antibodies that bind to any position in the amino acid regions from position 250 to 289, preferably from position 250 to 280, more preferably from position 280 to 270, even more preferably from position 280 to 265, still more preferably from position 280 to 260 of rice GID1 (SEQ ID NO: 2). Antibodies that bind to any position of the corresponding amino acid regions of *Arabidopsis* GID1 (see FIG. 5) are preferred.

The present invention also relates to transformed plant cells and transformant plants having a nucleic acid encoding a gibberellin-binding protein of the present invention introduced therein. Such transformant plants can be produced by introducing a vector carrying a nucleic acid encoding a gibberellin-binding protein of the present invention into plant cells and regenerating plants from the obtained transformed plant cells. Transformant plants include first-generation plants regenerated from transformed plant cells and plant progenies and clones thereof that contain the introduced nucleic acid. The progenies include plants generated through sexual or asexual reproduction (for example, vegetative reproduction and the like). The progenies also include progenies obtained through self pollination or cross pollination. For example, F1 and F2 plants produced through crossing with other plants, and their progenies which contain the introduced nucleic acid are also included in the transformant plants of the present invention.

The type of vector to be used in plant cell transformation is not particularly limited, so long as it can express inserted genes in the cells. For example, vectors in which a sequence encoding a protein of interest is linked downstream of a desired promoter may be used. It is preferred that a terminator be linked downstream of the coding sequence. Such promoters include, for example, constitutive promoters, such as the Opine promoter (U.S. Pat. No. 5,955,646), the 35S promoter of cauliflower mosaic virus (Odell et al. (1985) Nature 313: 810-812; U.S. Pat. No. 5,352,605; U.S. Pat. No. 5,530,196; U.S. Pat. No. 5,858,742; U.S. Pat. No. 6,255,560; EP 131623B2), the actin promoter (McElroy et al. (1990) Plant Cell 2:163-171; U.S. Pat. No. 5,684,239; EP 1042491; AU 18809/99; U.S. Pat. No. 5,859,331; EP 651812B1; EP 1179081A1; U.S. Pat. No. 5,641,876), the ubiquitin promoter (Christensen et al. (1989) Plant Mol. Biol. 12:619-632; Christensen et al. (1992) Plant Mol. Biol. 18:675-689; U.S. Pat. No. 5,510,474; U.S. Pat. No. 5,614,399; U.S. Pat. No. 6,020,190; U.S. Pat. No. 6,054,574), the alcohol dehydrogenase promoter (CA 1338858; EP 278658B1; U.S. Pat. No. 5,001,060; EP 459643B1; U.S. Pat. No. 5,290,924), and other promoters described in U.S. Pat. No. 5,608,149; U.S. Pat. No. 5,608,144; U.S. Pat. No. 5,604,121; U.S. Pat. No. 5,569,597; U.S. Pat. No. 5,466,785; U.S. Pat. No. 5,399,680; U.S. Pat. No. 5,268,463; and U.S. Pat. No. 5,608,142. Known inducible promoters include, for example, promoter systems that are regulated by alcohol, tetracycline, steroids, metal ions, or other compounds, or environmental stimulus. Such inducible promoters include, for example, the heat shock promoter (Ainley W M, Key J L (1990) Plant Mol Biol 14:949-967; Holtorf S, et al. (1995) Plant Mol Biol 29:637-646), the pathogen-responsive promoter (PR1-a; Williams S, et al. (1992) Biotechnology 10:540-543; Gatz C (1997) Annu Rev Plant Physiol Plant Mol Biol 48:89-108), the herbicide safener-responsive promoter (In2-2, GST-27; De Veylder L, et al. (1997) Plant Cell Physiol 38:568-577), the light-responsive promoter (Kuhlemeier C, et al. (1989) Plant Cell 1:471-478), the wounding-inducible promoter (Firek S, et al. (1993) Plant Mol Biol 22:129-142), the alcohol-responsive promoter (Salter M G, et al. (1998) Plant J 16:127-132), the phytohormone-responsive promoter (Li Y, et al. (1991) Plant Cell 3:1167-1175), the steroid-responsive promoter (Aoyama T, et al. (1997) Plant J 11: 605-612), the tetracycline-responsive promoter (Gatz C, et al. (1992) Plant J 2:397-404; Weinmann P, et al. (1994) Plant J 5:559-569; Sommer S, et al. (1998) Plant Cell Rep 17:891-896), and other promoters described in EP 637339B1; U.S. Pat. No. 5,851,796; U.S. Pat. No. 5,464,758; U.S. Pat. No. 5,589,362; U.S. Pat. No. 5,654,168; U.S. Pat. No. 5,789,156; U.S. Pat. No. 5,512,483; U.S. Pat. No. 6,379,945; EP 828829A1; EP 1112360A1; WO 01/62780; U.S. Pat. No. 4,940,661; U.S. Pat. No. 4,579,821; U.S. Pat. No. 4,601,978; U.S. Pat. No. 5,654,414; U.S. Pat. No. 5,689,044; U.S. Pat. No. 5,789,214; AU 708850B2; U.S. Pat. No. 6,429,362; U.S. Pat. No. 5,447,858; EP 159884 B1; CA 1338010A1; EP 922110A2; U.S. Pat. No. 6,084,089; EP 812917A1; U.S. Pat. No. 6,184,443; U.S. Pat. No. 5,847,102; U.S. Pat. No. 5,750,385; U.S. Pat. No. 5,639,952; and U.S. Pat. No. 5,656,496.

Tissue specific promoters include promoters described in Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 12(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6): 1129-1138; Matsuoka et al. (1993) Proc Natl. Acad. Sci. USA 90(20):9586-9590; Guevara-Garcia et al. (1993) Plant J 4(3):495-505, and others.

Terminators include, for example, terminators derived from cauliflower mosaic virus and terminators derived from the octopine synthase gene, nopaline synthase gene and such, but are not limited thereto (Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; Joshi et al. (1987) Nucleic Acid Res. 15:9627-9639). For example, codons to be use can be optimized for improved gene expression. For the optimization, for example, see the following documents: U.S. Pat. No. 5,380,831; U.S. Pat. No. 5,436,391; Murray et al. (1989) Nucleic Acids Res. 17:477-498).

Vectors can be introduced into plant cells using methods known to those skilled in the art. Plant cells to be used in gene transfer include, for example, suspension culture cells, protoplasts, plant cells such as in the scutellum of seeds, leaf discs, calluses and such. Specifically, the methods include, for example, *Agrobacterium*-mediated gene transfer using Ti plasmid vector (EP 270355, EP 0116718, Nucl. Acids Res. 12(22):8711-8721 (1984), Townsend et al., U.S. Pat. No. 5,563,055), particle gun (U.S. Pat. No. 5,100,792; EP 444882 B1; EP 434616 B1; Sanford et al., U.S. Pat. No. 4,945,050; Tomes et al. (1995) "Direct DNA Transfer into Intact Plant Cells via Microprojectile Bombardment" in Plant Cell, Tissue, and Organ Culture: Fundamental Methods, ed. Gamborg and Phillips (Springer-Verlag, Berlin); McCabe et al. (1988) Biotechnology 6:923-926), microinjection (WO 92/09696; WO 94/00583; EP 331083; EP 175966; Green et al. (1987) Plant Tissue and Cell Culture, Academic Press; Crossway et al. (1986) Biotechniques 4:320-334), electroporation (EP 290395; WO 8706614; Riggs et al. (1986) Proc. Natl. Acad. Sci. USA 83:5602-5606; D'Halluin et al. (1992) Plant Cell 4:1495-1505), as well as direct incorporation of DNA (DE 4005152; WO 9012096; U.S. Pat. No. 4,684,611; Paszkowski et al. (1984) EMBO J. 3:2717-2722), the liposome method (Freeman et al. (1984) Plant Cell Physiol. 29:1353), the voltex method (Kindle (1990) Proc. Nat. Acad. Sci. U.S.A. 87:1228), and the polyethylene glycol method. For gene transfer into plant cells, also see the following documents: Oard (1991) Biotech. Adv. 9:1-11; Weissinger et al. (1988) Ann. Rev. Genet. 22:421-477; Sanford et al. (1987) Particulate Science and Technology 5:27-37; Christou et al. (1988) Plant Physiol. 87:671-674; McCabe et al. (1988) Bio/Technology 6:923-926; Finer and McMullen (1991) In Vitro Cell Dev. Biol. 27P:175-182; Singh et al. (1998) Theor. Appl. Genet. 96:319-324; Datta et al. (1990) Biotechnology 8:736-740; Klein et al. (1988) Proc. Natl. Acad. Sci. USA 85:4305-4309; Klein et al. (1988) Biotechnology 6:559-563; Tomes, U.S. Pat. No. 5,240,855; Buising et al., U.S. Pat. No. 5,322,783, U.S. Pat. No. 5,324,646; Klein et al. (1988) Plant Physiol. 91:440-444; Fromm et al. (1990) Biotechnology 8:833-839; Hooykaas-Van Slogteren et al. (1984) Nature 311:763-764; Bytebier et al. (1987) Proc. Natl. Acad. Sci. USA 84:5345-5349; De Wet et al. (1985) in The Experimental Manipulation of Ovule Tissues, ed. Chapman et al. (Longman, N.Y.), pp. 197-209; Kaeppler et al. (1990) Plant Cell Reports 9:415-418; Kaeppler et al. (1992) Theor. Appl. Genet. 84:560-566; Li et al. (1993) Plant Cell Reports 12:250-255; Christou and Ford (1995) Annals of Botany 75:407-413; Osjoda et al. (1996) Nature Biotechnology 14:745-750.

For plant cell transformation, also see the following documents: Toriyama et al. (1988) Bio/Technology 6:1072-1074; Zhang, et al. (1988) Plant Cell Rep. 7:379-384; Zhang et al. (1988) Theor. Appl. Genet. 76:835-840; Shimamoto et al. (1989) Nature 338:274-276; Datta et al. (1990) Bio/Technology 8: 736-740; Christou et al. (1991) Bio/Technology 9:957-962; Peng et al. (1991) International Rice Research Institute, Manila, Philippines, pp. 563-574; Cao et al. (1992) Plant Cell Rep. 11:585-591; Li et al. (1993) Plant Cell Rep. 12:250-255; Rathore et al. (1993) Plant Mol. Biol. 21:871-884; Fromm et al. (1990) Bio/Technology 8:833-839; Tomes et al. (1995) "Direct DNA Transfer into Intact Plant Cells via Microprojectile Bombardment" in Plant Cell, Tissue, and Organ Culture: Fundamental Methods, ed. Gamborg and Phillips (Springer-Verlag, Berlin); D'Halluin et al. (1992) Plant Cell 4:1495-1505; Walters et al. (1992) Plant Mol. Biol. 18:189-200; Koziel et al. (1993) Biotechnology 11: 194-200; Vasil, I. K. (1994) Plant Mol. Biol. 25:925-937; Weeks et al. (1993) Plant Physiol. 102:1077-1084; Somers et al. (1992) Bio/Technology 10: 1589-1594; WO 92/14828; Hiei, et al. (1994) The Plant Journal 6:271-282); Shimamoto, K. (1994) Current Opinion in Biotechnology 5:158-162; Vasil, et al. (1992) Bio/Technology 10:667-674; Vain, et al. (1995) Biotechnology Advances 13(4):653-671; Vasil, et al. (1996) Nature Biotechnology 14:702.

The efficiency of gene transfer can be improved by using in combination two or more of the above-described gene transfer methods. For example, known methods include those in which microparticles coated with *Agrobacterium* projected to the plant tissues or co-cultured with *Agrobacterium* subsequent to impairment of the plant tissues with a particle gun (EP 486234; EP 486233).

More specific examples of known methods for preparing rice transformant plants include the following: the polyethylene glycol method (Datta, S. K. (1995) In Gene Transfer To Plants (Potrykus I and Spangenberg Eds.) pp 66-74), electroporation (Toki et al (1992) Plant Physiol. 100, 1503-1507), particle gun method (Christou et al. (1991) Bio/technology, 9: 957-962), *Agrobacterium* method using calluses (Hiei, Y. et al., Plant J. 6, 270-282 (1994)), and the *Agrobacterium* method using seeds (JP 2001-029075). These methods can be preferably used in the present invention.

Furthermore, the vector may carry an appropriate selection marker gene or, alternatively a plasmid vector containing a selection marker gene may be co-introduced into plant cells for efficient selection of transformed cells. Selection marker genes to be used for such purposes include, for example, the hygromycin phosphotransferase gene, the neomycin phosphotransferase gene, and the acetyl transferase gene which is responsible for resistance to phosphinothricin, a herbicide.

Regeneration of plants from transformed plant cells can be achieved by methods known to those skilled in the art depending on the type of plant cells (R. Abdullah et al., Bio/Technology, 4: 1087-1090 (1986); K. Toriyama et al., Theor. Appl. Genet., 73: 16-19 (1986); Y. Yamada et al., Plant Cell Reports, 5: 85-88 (1986)). For plant regeneration, also see the following documents: Vasil et al. (1984) in Cell Culture and Somatic Cell Genetics of Plants, Vols. I, II, III, Laboratory Procedures and Their Applications (Academic Press); Weissbach et al. (1989) Methods For Plant Mol. Biol. Progenies can be obtained from transformant plants through self pollination or cross pollination using the same transformant lines or other lines. Hybrids in which desired phenotypes have been introduced can also be prepared through cross pollination.

Progenies can be obtained from transformant plants through sexual or asexual reproduction. When breeding materials are prepared from the plants, progenies, or clones thereof, the plants can be produced on a large scale from these materials. The term "breeding material" refers to plant organs and tissues having the ability to grow into an whole plant body, and include seeds, cuttings, and vegetative organs and tissues. Specifically, vegetative organs include stumps, cuttings, rhizomes, tubers, bulbs, subterranean stems such as corms, creeping-roots alike rhizomes spreading in the soil, stolons that grow horizontally at the soil surface, and bulbils formed above the ground.

The present invention is applicable to desired plants which include, for example, plants selected from plants of the Gramineae family, Leguminosae family, Solanaceae family, Brassicaceae family, Cucurbitaceae family, Chenopodiaceae family, Apiaceae family, Asteraceae family, Rosaceae family, and Liliaceae family. Specifically, the plants include, for example, maize (*Zea mays*), canola (*Brassica napus* and *Brassica rapa* ssp.), alfalfa (*Medicago sativa*), rice (*Oryza sativa*), rye (*Secale cereale*), sorghum (*Sorghum bicolor* and *Sorghum vulgare*), sunflower (*Helianthus annuus*), barley (*Hordeum vulgare*), wheat (*Triticum aestivum*), soybean (*Glycine max*), tobacco (*Nicotiana tabacum* and *Nicotiana benthamiana*), potato (*Solanum tuberosum*), peanut (*Arachis hypogaea*), cotton (*Gossypium hirsutum*), sweet potato (*Ipomoea batatus*), coffee (*Coffea* spp.), coconut (*Cocos nucifera*), pineapple (*Ananas comosus*), citrus (*Citrus* spp.), cacao (*Theobroma cacao*), tea plant (*Camellia sinensis*), banana (*Musa* spp.), avocado (*Persea americana*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beet (*Beta vulgaris*), wild oat (oat), *Arabidopsis* spp., and other crops, vegetables, and ornamental plants. The present invention is preferably applicable to monocotyledonous plants and crop plants. Specifically, such plants include plants of the Gramineae family, Leguminosae family, and Polygonaceae family. More preferably, plants to which the present invention is applicable include plants of the Gramineae family, such as rice, barley, wheat, ray, millet, Japanese millet, foxtail millet, sugar cane, sorghum, adlay, maize, Japanese lawn grass, and oat, and even more preferably include rice (the genus *Oryza*).

The resulting plants preferably have enhanced sensitivity to gibberellin. The enhancement of gibberellin sensitivity means that at least one of the gibberellin activities is enhanced as compared to that of the parental line before introduction of a nucleic acid of the present invention. The sensitivity to gibberellin can be assayed, for example, by measuring plant height, leaf blade length, tillering number, mortality rate, leaf sheath elongation rate, α-amylase induction in seeds, and the like. In a preferred embodiment, two or more, more preferably three or more, or four or more of gibberellin activities are enhanced in transformants of the present invention as compared to the parental line before introduction of the nucleic acid of the present invention. Gibberellin activities include, for example, those of increasing plant height, leaf blade length, and leaf sheath elongation rate, reducing tillering number and mortality rate, enhancing germination and flowering, suppressing defoliation, enhancing cell division, inducing amylase in aleuron cells and synthesis of hydrolyrase, and activating intracellular signaling including induction of expression of GA-responsive genes. When plants have one or more, preferably two or more, three or more, or four or more of these characteristics, gibberellin sensitivity is judged to be enhanced in the plants. The specificity of such gibberellin activities can be confirmed by testing whether the effect differs between a transformant and non-transformant or whether the effect varies depending on the dose of gibberellin. For detection of intracellular GA signaling, see also the following documents: Yazaki J, et al., DNA Res., 2003, 10(6): 249-61; Yazaki J, et al., Physiol Genomics., 2004, 17(2):87-100; Margis-Pinheiro M, et al., Plant Cell Rep., 2005, 23(12): 819-33; Thomas S G, Sun T P., Plant Physiol., 2004, 135(2): 668-76; Ogawa M, et al., Plant Cell., 2003, 15(7):1591-604; Gomez-Maldonado J, et al., Planta., 2004, 218(6):1036-45; Skadsen R W., Plant Physiol., 1993, 102(1):195-203; Dill A, et al., Proc Natl Acad Sci USA., 2001, 98(24):14162-7; Bouquin T, et al., Plant Physiol., 2001, 127(2):450-8; Washio K., Biochim Biophys Acta., 2001, 1520(1):54-62; Ogawa M, et al., Plant Mol Biol., 1999, 40(4):645-57; Chono M, et al., Plant Cell Physiol., 1998, 39(9):958-67; Vishnevetsky M, et al., J Biol Chem., 1997, 272(40):24747-50; Toyomasu T, et al., Biosci Biotechnol Biochem., 1995, 59(10):1846-9; Cejudo F J, et al., Plant Mol Biol., 1992, 20(5):849-56; Gubler F, Jacobsen N., Plant Cell., 1992, 4(11):1435-41; Baulcombe D C, et al., J Biol Chem., 1987, 262(28):13726-35; Gale M D, Spencer D., Biochem Genet., 1977, 15(1-2): 47-57; Gopalakrishnan B et al., Plant Mol Biol., 1991, 16(3): 463-7; Cho, H. T., and H. Kende., 1997, Plant Cell 9: 1661-1671).

Gibberellin sensitivity is preferably determined based on the elongation of the second leaf sheath and/or induction of α-amylase in embryoless half seeds (Ueguchi-Tanaka, M. et al., Proc. Natl. Acad. Sci. USA, 97, 11638-11643 (2000); Yamaguchi, J. (1998) Breeding Sci. 48, 365-370; Chrispeels, M. J. and Varner, J. E. (1967) Plant Physiol. 42:398-406; Kashem M A et al. (1998) Planta, 205(3):319-26). For more details, refer to the Examples. The present invention relates to methods for enhancing gibberellin sensitivity, which include the step of increasing the expressions of gibberellin-binding proteins of the present invention. The methods also include methods for altering phenotypes, such as enhancing the growth or increasing the plant height as a result of enhancing gibberellin sensitivity. For example, the expression level of a gibberellin-binding protein of the present invention may be increased to acquire at least one of the gibberellin-hypersensitive phenotypes, such as increased growth rate. Further, the present invention relates to methods for enhancing gibberellin sensitivity, which include the step of introducing nucleic acids encoding gibberellin-binding proteins of the present invention into plant cells, and using such nucleic acids to enhance gibberellin sensitivity. These also include methods and uses for altering phenotypes, such as enhancement of growth increase in plant height as a result of enhancing gibberellin sensitivity. The present invention also relates to methods for producing plants having enhanced gibberellin sensitivity, which include the step of producing plants introduced with a nucleic acid encoding a gibberellin-binding protein of the present invention, and using such nucleic acid to produce such plants. These methods and uses also include methods for producing plants whose phenotypes have been altered, specifically, whose growth has been enhanced, or whose height has been increased as a result of the enhancement of gibberellin sensitivity, and the use of such plants. The present invention also relates to nucleic acids encoding the gibberellin-binding proteins of the present invention, which are solely used to enhance gibberellin sensitivity. The nucleic acids that are used to enhance gibberellin sensitivity refer to nucleic acids that are used exclusively to enhance gibberellin sensitivity. The present invention also relates to nucleic acids that are used exclusively to alter phenotypes as a result of enhancing gibberellin sensitivity, specifically by enhancing the growth or to increasing the plant height. Growth enhancement is expected to take place when gibberellin sensitivity is enhanced in plants. For example, the application of such nucleic acids to crops, such as food plants, can increase the yield. Furthermore, the plant height can be freely controlled.

The present invention also relates to plants in which the expression of gibberellin-binding proteins of the present invention is suppressed. The expression amounts of the proteins which such plants contain endogenously are decreased. The suppression of protein expression means that the expression amount of a protein of interest or an mRNA encoding the same is either reduced or eliminated. The suppression may result from transcription suppression, translation suppression, and/or reduce mRNA or protein stability, and the like. The suppression of expression can be confirmed based on phenotype alteration due to a decrease in the level of the protein or the mRNA, or activity of the protein in plant cells.

Nucleic acids that suppress the gibberellin-binding proteins of the present invention may be expressed in plants to suppress the expression of the proteins. Such nucleic acids include nucleic acids that, when expressed, suppress the transcription and/or translation of the genes encoding the proteins. Specifically, the antisense effects and RNAi can be used. The antisense effect in plant cells was demonstrated by Ecker et al. using the transient gene expression method (J. R. Ecker and R. W. Davis, (1986) Proc. Natl. Acad. USA. 83:5372). Subsequently, the expression of antisense RNA results in reduction of expressions of the target genes in many plants, including tobacco and petunia (A. R. van der Krol et al., (1988) Nature 333:866) has been reported. Currently, antisense RNA is an established means for suppressing gene expression in plants.

As shown below, the action of antisense nucleic acids in suppressing the expression of target genes involves multiple factors as follows: transcription inhibition by triplex formation, transcription suppression by the formation of hybrid with a portion of locally opened loop structure produced by RNA polymerase, transcription inhibition by the formation of a hybrid with an RNA in the process of synthesis, suppression of splicing by the formation of a hybrid at an intron-exon junction, suppression of splicing by the formation of a hybrid with the spliceosome formation portion, suppression of cytoplasmic translocation from the nucleus by the formation of a hybrid with an mRNA, suppression of splicing by the formation of a hybrid with a capping site or poly(A) site, suppression of translation initiation by the formation of a hybrid with a binding site for a translation initiation factor, suppression of translation by the formation of a hybrid with a ribosome-binding site adjacent to the start codon, inhibition of extension of peptide chain by the formation of a hybrid with a translational region or polysome-binding site of mRNA, suppression of gene expression by the formation of a hybrid with a nucleic acid-protein interaction site, RNA silencing-mediated mRNA degradation, and the like. These inhibit the process of transcription, splicing, or translation or degrade mRNA, and thus suppress target gene expression (Hirashima and Inoue, Shin Seikagaku Jikken Koza (New Courses in Experimental Biochemistry) 2, Kakusan (Nucleic Acid) IV: "Idenshi no Fukusei to Hatsugen (Replication and expression of genes)", Ed. The Japanese Biochemical Society, Tokyo Kagakudojin, pp. 319-347, 1993; Serio et al., (2001) Proc. Natl. Acad. Sci. USA 98:6506-6510).

An antisense sequence for use in the present invention may suppress its target gene expression by any of the actions described above. In one embodiment, antisense sequences designed to be complementary to the untranslated region adjacent of the 5' end of an mRNA of a gene are effective in inhibiting translation of the gene. Alternatively, sequences complementary to the coding region or 3' untranslated region can also be used. Thus, the antisense nucleic acids used in the present invention include not only those nucleic acids that include sequences antisense to the translational regions of genes, but also nucleic acids that include sequences antisense to the untranslated regions. The antisense nucleic acids to be used are linked downstream of an appropriate promoter, and preferably a transcription termination signal containing sequence is linked to the 3' end. Desired plants can be transformed with such DNAs prepared as described above using known methods. The sequences of antisense nucleic acids are preferably complementary to an endogenous gene of a plant or a portion thereof; however, the sequences do not have to be totally complementary, so long as they can effectively inhibit the expression of the genes. The transcribed RNA has a sequence of at least 18 nucleotides or more, preferably 20 nucleotides or more, and even more preferably 22, 25, 30, 35, 40, 50, 100, 200, or 500 nucleotides or more, which exhibits an identity of preferably 90% or higher, and most preferably 95% to the complementary sequences of the target gene transcripts. In general, the length of an antisense nucleic acid to be used is shorter than 5 kb, and preferably shorter than 2.5 kb.

The expression of an endogenous gene can also be suppressed using DNAs encoding ribozymes. Ribozymes are RNA molecules that have catalytic activity. There are various ribozymes with different activities. From amongst them, based on the studies of ribozymes that serve as RNA-cleaving enzymes, it has become possible to design a ribozyme for site-specific RNA cleavage. Ribozymes of the present invention include those large ribozymes composed of 400 nucleotides or more, such as group-I intron-type ribozymes and the M1RNA contained in RNAseP ribozyme, as well as ribozymes with an active domain of about 40 nucleotides, called as hammerhead- or hairpin-type ribozymes (Makoto Koizumi and Eiko Otsuka, (1990) Tanpakushitu, Kakusan, Koso (Protein, Nucleic acid and Enzyme), 35:2191).

For example, the autocleavage domain of hammerhead-type ribozymes cleaves $G^{13}U^{14}C^{15}$ at the 3' end of $C^{15}$. The base pairing of $U^{14}$ with A at position 9 is important for this activity, and cleavage has been shown to occur even when the nucleotide at position 15 is A or U instead of C (M. Koizumi et al., (1988) FEBS Lett. 228:225). When the substrate-binding site of a ribozyme is designed to be complementary to an RNA sequence adjacent to the target site, a restriction enzyme-like RNA-cleaving ribozyme that recognizes the sequence UC, U, or UA in the target RNA can be created (M. Koizumi et al., (1988) FEBS Lett. 239:285; Makoto Koizumi and Eiko Otsuka, (1990) Tanpakushitu, Kakusan, Koso (Protein, Nucleic acid and Enzyme), 35:2191; M. Koizumi et al., (1989) Nucleic Acids Res. 17:7059). For example, there are many potential target sites in the coding sequences of SEQ ID NOs: 1, 4, 6, and 8.

The hairpin ribozyme is also useful in suppressing gene expression. Hairpin ribozymes are found in, for example, the minus strand of satellite RNAs of tobacco ringspot viruses (J. M. Buzayan Nature 323:349, 1986). It has been shown that target-specific RNA-cleaving ribozymes can also be designed based on this type of ribozymes (Y. Kikuchi and N. Sasaki (1992) Nucleic Acids Res. 19:6751; Kikuchi Y. Kagaku to Seibutsu (Chemistry and Biology) 1992, 30, 112).

A ribozyme designed to be capable of cleaving its target is linked with promoter and transcription terminator, such that it can be transcribed in plant cells. However, the ribozyme may lose its activity when extra sequences are added to the 5' or 3' end of the transcribed RNA. In such cases, a trimming ribozyme that acts in cis for the trimming may be arranged at the 5' or 3' end of the ribozyme moiety to precisely excise only the ribozyme moiety from the transcribed RNA of the ribozyme (K. Taira et al., (1990) Protein Eng. 3:733; A. M. Dzianott and J. J. Bujarski (1989) Proc. Natl. Acad. Sci. USA. 86:4823; C. A. Grosshans and R. T. Cech (1991) Nucleic Acids Res. 19:3875; K. Taira et al., (1991) Nucleic Acids Res. 19:5125). Furthermore, the effect can be further enhanced by arranging such constitutional units in tandem to allow cleavage at multiple sites in the target gene (N. Yuyama et al., Biochem. Biophys. Res. Commun. 186:1271, 1992). Target gene expression can be suppressed by specifically cleaving transcripts of the target genes using such ribozymes.

Alternatively, suppression of the expression of an endogenous gene can be achieved through co-suppression, resulting from the transformation with a DNA having a sequence identical or similar to the target gene sequence. There are two known types of co-suppression: transcriptional gene silencing (TGS) and post-transcriptional gene silencing (PTGS). Both refer to the phenomenon that the expression of a target endogenous gene is suppressed when a gene having a sequence identical or similar to the target endogenous gene is introduced into plants through transformation, which are often found in plants (Curr. Biol. 7:R793, 1997, Curr. Biol. 6:810, 1996). The phenomenon is also known as homologous gene silencing (HGS). The plants in which the expression of nucleic acids of the present invention has been co-suppressed can be obtained, for example, by transforming the target plants with a vector prepared, such that a DNA of the present invention or a DNA having a sequence similar thereto can be expressed, and then plants in which the expression of the target gene is suppressed as compared to wild-type plants are selected from the resulting plants. Such genes to be used in cosuppression is not necessarily completely identical to the target genes (for example, SEQ ID NOs: 1, 4, 6, or 8), however the genes preferably have a sequence identity of at least 70% or higher, preferably 80% or higher, more preferably 90% or higher (for example, 95%, 96%, 97%, 98%, or 99% or higher). It is preferable that such nucleic acids to be transcribed do not encode any protein having gibberellin-binding activity. For example, to prevent the expression of functional proteins, nucleic acids having a deletion, insertion, or substitution of a nucleotide in the protein-coding sequence are preferably used.

Parts of the mechanism of RNA interference (RNAi)- or micro RNA (miRNA)-mediated suppression of the expression is understood to be involved in PTGS and HGS in cosuppression (van der Krol A R, et al., Plant Cell, 1990, 2(4):291-9; Jorgensen R A, et al., Plant Mol Biol, 1996, 31(5):957-73; Vance and Vaucheret (2001) Science 292:2277-2280; Kerschen, A. et al., 2004, FEBS Letters 566:223-228; Jorgensen, R. A., 2003, Sense cosuppression in plants: past, present and future. In: RNAi: a Guide to Gene Silencing (ed. G. J. Hannon), Cold Spring Harbor Laboratory Press, pp. 5-21). RNAi is a phenomenon whereby the expression of a target gene is suppressed when a double-stranded RNA (hereinafter, abbreviated as dsRNA) having a sequence identical or similar to the target gene sequence is introduced into cells. When dsRNA of about 40 to several hundreds of base pairs is introduced into the cells, the Dicer, an RNaseIII-like nuclease, excises the dsRNA from the 3' end, about 21 to 23 base pairs at a time, which results in an siRNA (short interference RNA or small interfering RNA). Binding of a specific protein to this siRNA forms a nuclease complex (RNA-induced silencing complex (RISC)). This complex recognizes and binds to a sequence that is the same as that of siRNA, and cleaves the mRNA of the target gene at a position corresponding to the center of siRNA by RNaseIII-like enzyme activity. Besides this pathway, the antisense strand of siRNA binds to mRNA and acts as a primer for RNA-dependent RNA polymerase (RdRP) to synthesize dsRNA. This dsRNA becomes the substrate of Dicer again, which results in the production of a new siRNA, and the amplification of its action.

RNAi has been observed in a wide variety of eukaryotic cells. Currently, RNAi is widely used as a method for effectively suppressing target gene expression (Fire, A. RNA-triggered gene silencing. Trends Genet. 15, 358-363 (1999); Sharp, P. A. RNA interference 2001. Genes Dev. 15, 485-490 (2001); Hammond, S. M., Caudy, A. A. & Hannon, G. J. Post-transcriptional gene silencing by double-stranded RNA. Nature Rev. Genet. 2, 110-1119 (2001); Zamore, P. D. RNA interference: listening to the sound of silence. Nat Struct Biol. 8, 746-750 (2001)). As described above, in particular, RNAi in plants has long been known to be cosuppressive. The suppression of gene expression using RNAi is frequently used as a method for preparing knockdown plants for desired genes (Chuang C F & Meyerowitz E M: Proc. Natl. Acad. Sci. USA 97: 4985, 2000; Tomita, R. et al., FEBS Lett. 573: 117-120). Vectors for transcribing RNA that induces RNAi against genes encoding the proteins (referred to as RNAi-RNA) can also be preferably used in the present invention to produce plants in which the expression of gibberellin-binding proteins of the present invention is suppressed.

For example, double-stranded RNA (dsRNA) that includes a sense strand composed of a portion of the coding sequence of a target gene and the complementary strand thereof can be used as the RNAi-RNA. For example, siRNA composed of a short double-stranded region is preferably expressed. siRNAs of about 21 to 23 base pairs are preferred, however the length is not particularly limited, as long as it is within a range where the siRNAs exert no toxicity to the cells. For example, siRNAs can be 15 to 49 base pairs, preferably 15 to 35 base pairs, and more preferably 21 to 30 base pairs in length. siRNAs can be appropriately generated by transcription from the expression vectors. Promoters to be used include, for example, RNA polymerase III promoter (McManus et al. (2002) RNA 8:842-850). The expression vectors for siRNA may transcribe the siRNA as follows. For example, RNA composed of the coding sequence of the target protein and another RNA having the complementary sequence thereof may be transcribed as individual RNA molecules; alternatively, they may be transcribed as an RNA molecule in which the two are linked together via a spacer. RNA transcribed as a single strand is converted into double-stranded RNA with a hairpin structure (self-complementary hairpin RNA (hpRNA)), and the expression of the target gene is suppressed by RNAi (Smith, N. A. et al. Nature, 407:319, 2000; Wesley, S. V. et al. Plant J. 27:581, 2001; Piccin, A. et al. Nucleic Acids Res. 29:E55, 2001).

The sequence of a double-stranded region of an RNAi-RNA does not need to be completely identical to the target gene, however, the sequence identity is preferably 90% or higher (for example, 95%, 96%, 97%, 98%, 99% or higher). The double-stranded RNA portion formed by RNA-RNA pairing in dsRNA is not limited to the matched duplexes, but may include unpaired portions due to mismatches (the corresponding nucleotide is not complementary) and/or bulges (lack of the corresponding nucleotides of one strand). The numbers of mismatches and bulges are typically 1 to 6, preferably 1 to 3.

Much like those described above, miRNA (micro RNA) can also be used to inhibit target gene expression. miRNA may be expressed as a portion of precursor RNA (Reinhart et al. (2002) Genes & Development 16:1616-1626; Llave et al. (2002) Plant Cell 14:1605-1619). In general, the size of miRNA is about 15 to 30 nucleotides, and the miRNA having a sequence complementary to its target mRNA. For construction of miRNA precursor and suppression of target gene expression using miRNA, see previously published documents: McManus et al. (2002) RNA 8:842-850; Reinhart et al. supra; Llave et al. (2002) supra). When miRNA is transcribed from the expression vectors, for example, RNA polymerase III promoters may be used (McManus et al. (2002) RNA 8:842-850).

Plants in which the expression of a gibberellin-binding protein of the present invention is suppressed can be produced by introducing into plant cells an expression vector containing a nucleic acid, such as antisense, ribozyme, cosuppression nucleic acid, siRNA, or miRNA as described above, that suppresses the expression of a protein of the present invention, and regenerating plants from the cells. The present invention provides vectors carrying nucleic acids that suppress the expression of gibberellin-binding proteins of the present invention, specifically, antisense RNAs against RNAs encoding gibberellin-binding proteins of the present invention, ribozymes that cleave RNAs encoding the proteins, cosuppression-inducing RNAs that suppress the expression of the proteins through cosuppression, nucleic acids encoding siRNAs or miRNAs that suppress proteins expression, and vectors carrying the nucleic acids. The present invention also relates to plant cells which were introduced with the nucleic acids and plants containing the cells. Vector introduction and plant regeneration can be achieved by the methods described above. The present invention relates to methods for reducing gibberellin sensitivity, which include the step of suppressing the expression of gibberellin-binding proteins of the present invention. The suppression of the expression of a protein of the present invention includes reduction or disappearance of the activity of the protein by introducing mutations into the protein. Specifically, the expression of a protein of the present invention can be suppressed by inhibiting the expression of the functional protein through disruption of a gene encoding a protein of the present invention by introducing mutations, deletions, or insertions into the gene. The methods also include methods for altering phenotypes through reduction of gibberellin sensitivity, specifically methods for suppressing growth, shortening plant height, or inducing dwarfness. For example, the expression levels of gibberellin-binding proteins of the present invention may be reduced to allow acquisition of at least one of the phenotypes for low sensitivity to gibberellin, such as dwarfism. The present invention also relates to methods for reducing gibberellin sensitivity, which include the step of introducing nucleic acids that suppress the expression of gibberellin-binding proteins of the present invention into plant cells, and uses of the nucleic acids to reduce gibberellin sensitivity. These include methods and uses for altering phenotypes through reducing gibberellin sensitivity, such as methods for suppressing the growth, shortening the plant height, and inducing dwarfness. The present invention also relates to nucleic acids suppressing the expression of gibberellin-binding proteins of the present invention, which are used to reduce gibberellin sensitivity. The nucleic acids that are used to reduce gibberellin sensitivity refer to nucleic acids that are exclusively used to reduce gibberellin sensitivity. The present invention also relates to nucleic acids that are exclusively used to alter phenotypes by reducing gibberellin sensitivity, specifically to suppress growth, to shorten plant height, or to induce dwarfness. The present invention also relates to methods for producing plants with reduced gibberellin sensitivity, which include the step of producing plants which were introduced with nucleic acids suppressing the expression of gibberellin-binding proteins, and uses of the nucleic acids in producing plants with reduced gibberellin sensitivity. These methods and uses also include methods and uses for producing plants whose phenotypes have been altered, i.e., whose growth has been suppressed, whose height has been shortened, or in which dwarfness has been induced, by the reduction of gibberellin sensitivity. When a plant has multiple (two, three, or more) genes which encode the proteins of the present invention, the sensitivity to gibberellin can be effectively reduced by suppressing the expression of two or more, preferably three or more, or more preferably all of the genes. Transformant plants which were introduced with nucleic acids that suppress the expression of gibberellin-binding proteins include the first-generation plants regenerated from transformed plant cells, and plants carrying the nucleic acids, which are the progenies or clones thereof. Progenies can be obtained from the transformant plant by sexual or asexual reproduction. Furthermore, breeding materials (for example, seeds, fruits, cuttings, tubers, tuberous roots, and stumps) can be obtained from the plants, progenies, or clones thereof. When progenies are produced by sexual reproduction, self pollination as well as crossing with other plants may be used.

As compared to the parental line or wild type, the sensitivity to gibberellin is reduced in plants produced by the methods described above. The reduction of gibberellin sensitivity can be confirmed, for example, based on the presence of one or more, preferably two or more, three or more, or four or more features of gibberellin action, such as shortening of plant height and leaf blade length, increase in tillering number and mortality rate, decrease in leaf sheath elongation rate, and decrease in degree of amylase induction. For example, the level of SD1 mRNA (Sasaki, A. et al., Nature 416, 701-702 (2002)) may be increased (for example, to 1.5 times or more, preferably 2 times or more, 3 times of more, or 5 times or more) in plants in which the expression of proteins of the present invention is suppressed as compared to a control plant (parental line before suppression). Alternatively, $GA_1$ level may be increased (for example, 2 times or more, preferably 5 times or more, 10 times or more, 20 times or more, 50 times or more, or 100 times or more) in plants in which the expression of proteins of the present invention is suppressed as compared to that of the control plant. Furthermore, degradation of SLR1 protein caused by gibberellin may be significantly inhibited in plants in which the expression of proteins of the present invention is suppressed as compared to that of the control plant. Details of Gibberellin activities are described herein above. Gibberellin sensitivity is preferably determined based on the elongation of the second leaf sheath and/or induction of α-amylase in embryoless half seeds (Ueguchi-Tanaka, M. et al., Proc. Natl. Acad. Sci. USA, 97, 11638-11643 (2000)). Specifically, the degree of elongation of the second leaf sheath is reduced and/or the degree of induction of α-amylase is reduced in plants with reduced gibberellin sensitivity as compared to that of the parental line or wild type. According to the present invention, plants can be modified to result in a dwarf type by reducing gibberellin sensitivity of plants, as described above. In particular, when tall plants are modified into a short-culmed dwarf type, their tolerance to lodging can be improved. The yields of short-culmed crop plants are expected to be increased. Indeed, a short-culmed high-yielding rice variety (IR8) has been developed by introducing mutations in the gene encoding GA20-oxidase, which is one of the enzymes involved in gibberellin biosynthesis (Sasaki, A. et al., Nature, 2002, 416, 701-702). Improvement in yield of the agriculturally important crops is a important objective worldwide. In particular, there is a strong need to develop high-yielding varieties of crop plants, such as rice, wheat, barley, wild oat, rye, corn, and chestnut-tree. Crops that are expected to have higher yields can be created by making crop plants into short-culmed types according to the present invention. Alternatively, non-crop plants, for example, ornamental plants can be made into dwarf types to confer new aesthetic values. The present invention provides, for example, ornamental dwarfed bonsai rice plants in which the expression of gibberellin-binding proteins of the present invention is suppressed.

The present invention also relates to methods for binding gibberellin to the proteins of the present invention, which include the step of contacting gibberellin with the proteins. The gibberellin may be any biologically active gibberellin. In addition, the present invention also relates to methods for binding the proteins of the present invention to DELLA proteins, which include the step of contacting the proteins of the present invention with DELLA proteins. Furthermore, the present invention also relates to methods for binding gibberellin, DELLA proteins, and the proteins of the present invention together, which include the step of allowing them to coexist. As described below, these methods are useful in assaying compounds that regulate the binding, or in screening for the compounds that regulate the binding. Compounds obtained by such screening are useful in regulating gibberellin signaling. The binding reaction can be appropriately conducted using physiological solutions. Such solutions include, for example, binding buffer [20 mM Tris-HCl (pH7.6), 5 mM 2-mercaptoethanol, and 0.1 M NaCl], but are not limited thereto. The present invention also relates to isolated complexes composed of gibberellin and the proteins of the present invention, and isolated complexes composed of DELLA proteins and the proteins of the present invention. Furthermore, the present invention also relates to isolated complexes composed of gibberellin, DELLA proteins, and the proteins of the present invention.

DELLA proteins refer to GA signaling regulatory proteins grouped in the DELLA subfamily of the plant GRAS family (Peng J et al. (1999) Nature 400: 256-261; Itoh, H. et al., Trends Plant Sci. 8, 492-497 (2003)). DELLA proteins have been known to have the function of suppressing gibberellin signaling. There are many known DELLA proteins, including, for example, Arabidopsis RGA, GAI, RGL1, RGL2, and RGL3, rice SLR1, barley SLN1, maize D8, and wheat RHT (Fleet, C. M., and Sun, T.-P. (2005) Curr. Opin. Plant Biol., 8, 77-85; Dill, A., and Sun, T. (2001) Genetics, 159, 777-785; Ueguchi-Tanaka, M. et al. (2005) Nature, 437, 693-698; Chandler P M et al. (2002) Plant Physiol 129: 181-190; Gubler F et al. (2002) Plant Physiol 129: 191-200; Peng J et al. (1999) Nature 400: 256-261). More specifically, DELLA proteins include, for example, RGA (Location: At2g01570, Accession number; NM_126218, CDS: 207 . . . 1967, Protein ID: NP_178266), GAI (Location: At1g14920, Accession number; NM_101361, CDS: 189 . . . 1787, Protein ID: NP_172945), RGL1 (Location: At1g66350, Accession number; NM_105306, CDS: 133.1665, Protein ID: NP_176809), RGL2 (Location: At3g03450, Accession number; NM_111216, CDS: 128 . . . 1768, Protein ID: NP_186995), RGL3 (Location: At5g17490, Accession number; AK117226, CDS: 191 . . . 1759, Protein ID: BAC41902), rice SLR1 (Accession number; AB030956, CDS: 216 . . . 2090, Protein ID: BAA90749), barley SLN1 (Accession number; AF460219, CDS: 1765 . . . 3618, Protein ID: AAL66734, Q8W127), maize D8 (Accession number; AJ242530, CDS: 1 . . . 1890, Protein ID: CAB51557), and wheat RHT (Accession number; AJ242531, CDS: 1 . . . 1869, Protein ID: CABB51555, Q9ST59).

DELLA proteins of other plants can be isolated, for example, by methods such as hybridization using probes prepared from the coding sequences (CDS) of the above-listed DELLA genes or the complementary sequences thereof. Those skilled in the art can appropriately select the conditions for hybridization. Such conditions are for example, hybridization in a solution containing 5×SSC (1×SSC contains 150 mM NaCl and 15 mM sodium citrate), 7% (W/V) SDS, 100 μg/ml denatured salmon sperm DNA, 5×Denhardt's solution (1×Denhardt's solution contains 0.2% polyvinylpyrrolidone, 0.2% bovine serum albumin, and 0.2% Ficoll) at 48° C., preferably at 52° C., and more preferably at 60° C., followed by washing in 2×SSC at the same temperature as used in the hybridization, preferably at 60° C., and more preferably at 65° C., for 2 hours while shaking. More preferably washing is carried out in 1×SSC, even more preferably in 0.5×SSC, and still more preferably in 0.1×SSC (Sambrook, J. and D W Russell, 2001, Molecular Cloning, A Laboratory Manual, Third Edition, Cold Spring Harbor Laboratory Press, Cold Spring Harbor, N.Y.).

The amino acid sequences of DELLA proteins or the coding sequences (CDS) therefore preferably possess a sequence that is highly homologous to any one of the above-described Arabidopsis or rice DELLA proteins or nucleotides, respectively. High homology refers to a sequence identity of 60% or higher, preferably 65% or higher, more preferably 70% or higher, even more preferably 75% or higher, 80% or higher, 85% or higher, 90% or higher, and still more preferably 95% or higher. Sequence identity is determined by the methods described herein.

The present invention provides methods for assaying (assessing) gibberellin response, which include the steps of contacting gibberellin with plants or plant cells in which the expression of a protein of the present invention has been increased or reduced, and detecting gibberellin response in the plants or plant cells. The term "gibberellin responsive assay" refers to quantitative and/or qualitative assays for gibberellin response, and may be the detection of the presence of gibberellin response, determination of the degree of gibberellin response, and the like. Such gibberellin responses also include phenotype alterations caused by gibberellin, such as alterations in plant height and growth rate. Such plants and plant cells in which the expressions of proteins of the present invention is increased or reduced also include desired plants and plant cells in which amounts of the proteins or mRNAs are known to be increased or reduced (or eliminated). Such plants and plant cells may be, for example, plants and plant cells in which amounts of the proteins or mRNAs have already been described or known to be increased or reduced. The assay can be carried out, for example, using plants or plant cells introduced with vectors encoding a gibberellin-binding protein of the present invention or vectors encoding a nucleic acid (antisense, siRNA, or such) that suppresses the expression of the protein. For example, a biologically active gibberellin may be contacted with plants or plant cells introduced with a nucleic acid encoding a protein of the present invention, and then gibberellin response may be detected. Such assays enable one to determine the enhanced gibberellin response caused by the introduction of a nucleic acid encoding a protein of the present invention and the degree of the enhancement. Alternatively, the decrease d and the degree of the decrease of gibberellin response can be determined by contacting gibberellin with plants or plant cells introduced with a nucleic acid, such as antisense or siRNA, which suppresses the expression of a nucleic acid encoding a protein of the present invention and then detecting gibberellin response. Gibberellin responses may be detected by known methods.

The present invention also provides methods for assaying the gibberellin response, which include the steps of contacting a test compound with plants or plant cells in which the expression of a protein of the present invention has been increased or decreased and detecting gibberellin response in the plants or cells. The gibberellin response assay refers to quantitative and/or qualitative measurements for gibberellin response, including detection of the presence of gibberellin response or determination of the degree of gibberellin response. For example, since the sensitivity to gibberellin has been enhanced in plants in which the expressions of the proteins of the present invention have been increased, the effect of a test compound on gibberellin response can be clearly detected. Furthermore, the specificity of the effect can be tested by comparing the result to that obtained by treating the wild type plant with the test compound. Alternatively, the effect of inducing gibberellin response in a manner independent of the proteins of the present invention can be detected through assays of test compounds using plants in which the expressions of proteins of the present invention have decreased. Such assays can assess proteins or other compounds that regulate gibberellin signaling without involving the proteins of the present invention.

The above-described assays using test compounds may further include the step of contacting gibberellin. Specifically, the present invention provides assay methods for gibberellin response, which include the steps of: (a) contacting a test compound with plants or plant cells in which the expression of a protein of the present invention has been increased, in the presence of gibberellin; and (b) detecting gibberellin response in the plants or cells in the presence or absence of the test compounds. Such gibberellins include desired biologically active gibberellins. These methods enable assays for compounds that regulate gibberellin response. Such assays are useful in assessing whether the test compounds regulate gibberellin response or in assessing the degree of regulation.

In one embodiment of such assay methods, the present invention provides methods for selecting compounds that regulate gibberellin response. Specifically, the above-described assay methods may be conducted in the presence of a test compound and gibberellin response may be detected. Then, test compounds that enhance or reduce gibberellin response are selected. This method enables to screen for novel gibberellin derivatives or compounds that inhibit the effect of gibberellin. As a control for comparison, the assay is conducted in the absence (or at a low dose) of a test compound or in the presence of other compounds. Test compounds that enhance or reduce gibberellin response as compared to the gibberellin response of the control may be selected.

In addition, the present invention also provides methods for detecting the binding of gibberellin, which include the steps of contacting gibberellin with a protein of the present invention and detecting the binding of gibberellin to the protein. The present invention also relates to proteins of the present invention that are used as gibberellin-binding proteins. The proteins used as gibberellin-binding proteins refer to proteins that are exclusively used in gibberellin binding. Such gibberellins include desired biologically active gibberellins. The gibberellin binding can be detected by the methods described herein. Furthermore, in one embodiment of the detection method, the present invention provides assay methods for compounds that regulate the interaction between gibberellin and the proteins of the present invention. Specifically, whether test compounds enhance or inhibit the binding between gibberellin and a protein of the present invention or the degree of enhancement or inhibition can be assessed by contacting test compounds, gibberellin, and the proteins of the present invention together and by detecting the binding of gibberellin to the proteins. As a control, the binding between gibberellin and a protein of the present invention is detected in the absence (or at a low dose) of test compounds or in the presence of other compounds and the results may be compared. Furthermore, in one embodiment of this assay method, the present invention provides methods for selecting compounds that enhance or inhibit the binding between gibberellin and a protein of the present invention. Specifically, the binding between gibberellin and the protein is detected after contacting test compounds, gibberellin, and a protein of the present invention together. Through selection of compounds that enhance or inhibit the binding, compounds that either enhance or inhibit the binding between gibberellin and a protein of the present invention are obtained. As a control, the binding between gibberellin and a protein of the present invention may be detected in the absence (or at a low dose) of the test compounds or in the presence of other compounds and the results may be compared. These methods enable screening for novel compounds that regulate gibberellin responses.

EXAMPLES

Hereinbelow, the present invention will be specifically described with reference to Examples, but it should not be construed as being limited thereto. All prior art references cited herein are incorporated by reference into this description.

Plant Materials and Growth Conditions

In the Examples below, the rice variety *Oryza sativa* L. cv. Taichung 65, japonica (the original line from which mutants derive), four gid1 mutant alleles (gid1-1 to gid1-4), and slender rice1 (slr1-1) (Ikeda, A. et al., Plant Cell. 13, 999-1010 (2001)) are used as examples. The gid1 mutant alleles are caused by the following mutagens: N-methyl-N-nitrosourea (gid1-1), cell culture (gid1-2 and gid1-4), and γ rays (gid1-3). All rice plants were grown at 30° C. (day) and 24° C. (night) in a greenhouse.

GA Responsiveness Assay

GA responsiveness assays for the elongation of the second leaf sheath and induction of α-amylase in embryoless half seeds of rice were carried out using the methods described in Ueguchi-Tanaka, M. et al., Proc. Natl. Acad. Sci. USA, 97, 11638-11643 (2000)).

Plasmid Construction

DNAs sequence corresponding to full-length cDNAs for the wild-type and mutant GID1 were amplified by PCR to produce recombinant rice GID1 protein. GID1 cDNA sequences with and without mutation were inserted into pGEX-4T (Pharmacia). For the complementation assay, rice genomic DNAs from BAC clones were digested with PstI, and a 6.7-kb DNA fragment covering the entire GID1 sequence was isolated and cloned into pBluescript® vector. This fragment was blunted and inserted into a SmaI site of the hygromycin-resistant binary vector pGI-Hm12 (Hm-2 was modified; Sato, Y. et al., Plant Mol. Biol., 1998, 38:983-998). The construction of SLR1 promoter-SLR1-GFP has been described previously (Itoh, H. et al., Plant Cell 14, 57-70 (2002)). These constructs were introduced into rice cells by *Agrobacterium tumefaciens*-mediated transformation as described in Hiei, Y. et al., Plant J. 6, 270-282 (1994).

Measurement of Endogenous GA and Other Analyses

Quantitative analyses of endogenous GAs of rice were carried out by gas chromatography-selected ion monitoring as described previously (Kobayashi, M. et al., Biosci. Biotechnol. Biochem. 59, 1969-1970 (1995)). RNA gel blot analyses and Western blot analyses were performed as described previously (Itoh, H. et al., Plant Cell 14, 57-70 (2002)).

Gibberellin-Binding Assay

In the gibberellin-binding assay, $[1,2,16,17-^3H_4]16,17$-dihydro-$GA_4$ was used as a labeled $GA_4$. In vitro GA-binding assays were carried out using previous methods with some modifications (Nakajima, M. et al., Biochem. Biophys. Res. Comm. 241, 782-786 (1997)). The purified recombinant GID1 protein (400 pmol) was dissolved in 300 μl of binding buffer [20 mM Tris-HCl (pH 7.6), 5 mM 2-mercaptoethanol, and 0.1 M NaCl], and incubated with 100 μl of $^3H_4$-16,17-dihydro$GA_4$ (6 pmol) for two hours at 25° C., either in the absence of non-labeled $GA_4$ (total binding) or in the presence of 833-fold excess non-labeled $GA_4$ (total non-specific binding). Then, 0.1 ml of the reaction mixture was loaded onto a NAP-5 column (Amersham Biosciences, Piscataway, N.J.). The eluate of the binding buffer (0.6 ml) was discarded, the subsequent eluate (0.2 ml) was collected, and the radioactivity was measured. The specific binding activity, reflecting the number of displaceable GA binding sites, was calculated by subtracting the amount of nonspecific binding from the amount of total binding. The same as above can also be carried out for other GAs.

Example 1

Identification of Gibberellin-Insensitive Dwarf Mutants

To isolate genes involved in gibberellin perception, GA-insensitive dwarf mutants (gid) of rice were screened, and a few gid mutations were identified on different loci. gid1-, which is one of the mutants, exhibited severe dwarfism and enlarged leaf blades with dark green coloring, which are phenotypes typical of known GA-related mutants in rice (Sasaki, A. et al., Science 299, 1896-1898 (2003); Itoh, H et al., Proc. Natl. Acad. Sci. USA 98, 8909-8914 (2001); Sakamoto, T. et al., Plant Physiol. 134, 1642-1653 (2004)) (FIG.

1a). This mutation was recessively inherited, and since no fertile flowers developed, the mutant was maintained as a heterozygous plant. In the range of the tests carried out, this gid1 plant did not show any type of GA responsiveness. The elongation of the second leaf sheath was promoted with $GA_3$ at $10^{-8}$ M or higher in the wild-type plant (WT), but not promoted at all in gid1-1 (FIG. 1b). Furthermore, α-amylase activity was induced with $GA_3$ at $10^{-9}$ M or higher in wild-type seeds, but not in gid1-1 seeds (FIG. 1c). A negative feedback by $GA_3$ on the expression of SD1OsGA20ox2 (Sasaki, A. et al., Nature 416, 701-702 (2002)), a GA biosynthesis gene (Thornton, T. M. et al., Trends Plant Sci. 4, 424-428 (1999)), was observed in the wild-types; however, this was not observed in gid1-1, and SD1 mRNAs accumulated to a high level (FIG. 1d). Furthermore, the levels of endogenous GAs were measured, and as a result, it was revealed that about 120 times more $GA_1$ had accumulated in gid1-1 as compared to the wild-types (FIG. 1e). These results all prove that gid1-1 is a GA-insensitive mutant.

Next, an epistatic analysis was carried out for gid1 and slr1. Double mutants exhibited the slr1 phenotype (FIG. 1g). This showed that GID1 and SLR1 function on the same GA signaling pathway, and that SLR1 functions epistatically to GID1. GA-dependent SLR1 degradation is essential for GAs' effects, and plants are known to exhibit the gid phenotype when the degradation is inhibited (Sasaki, A. et al., Science 299, 1896-1898 (2003)). Immunoblot analysis for SLR1 was carried out to test whether SLR1 degradation was inhibited in gid1-1. Complete degradation of SLR1 was induced within 30 minutes after $GA_3$ treatment in the wild-types; however, SLR1 proteins were maintained at a same level in gid1-1 with or without $GA_3$ treatment even after two hours (upper panel in FIG. 1f). The increase in gid1 of the stability of SLR1 in response to $GA_3$ was also observed in transgenic plants into which SLR1 promoter-SLR1-GFP had been introduced: GFP signals were observed in nuclei even after $GA_3$ treatment in gid1-1, whereas no signal was observed in nuclei of the wild-types (lower panel in FIG. 1f). These results prove that GID1 is essential for SLR1 degradation.

Example 2

Cloning of Gibberellin Receptor Genes

The GID1 gene was isolated by positional cloning and the mutation sites in the four types of mutant alleles were determined to elucidate the molecular functions of GID1 (FIG. 2). The predicted GID gene is composed of one intron and two exons and encoded a polypeptide of 354 amino acid residues (FIGS. 2b and 3a). The analysis of the full-length cDNA sequence for this gene confirmed that the predicted exon regions were correct and that this gene is actually transcribed. When a 6.7-kb PstI fragment covering the entire region of the GID gene was introduced into gid1-1, it was revealed that the phenotype returns to the normal phenotype.

The amino acid sequence of GID1 protein was analyzed, and it was revealed that GID1 includes consensus sequences of the hormone sensitive lipase (HSL) family (FIG. 3b). Indeed, GID has both the GXSXG and HGG motifs (dots in FIG. 3b) which are the most conserved motifs in the HSL family (Osterlund, T. et al., Biochem. J. 319, 411-420 (1996); Manco, G. et al., Arch. Biochem. Biophys. 373, 182-192 (2000)). The single amino acid substitution from G to D at the first position in the GXSXG motif in the gid1-1 allele results in a severe phenotype (FIG. 3a). Thus, the GXSXG motif was demonstrated to be important for GID1 functions. The structural similarity between GID1 and the HSL protein family suggests that GID1 has HSL-like functions in rice. The cellular localization of GID1 was investigated by observing GFP signals in transgenic plants expressing Act1 promoter-GID1-GFP. GID1-GFP proteins were mainly localized in the nucleus, while weak signals were detected in the cytoplasm. This cellular localization was not altered before and after $GA_3$ treatment (FIG. 3c).

Example 3

Molecular Analyses of Gibberellin Receptors

SLR1 degradation by GA does not occur in gid1 (FIG. 1f). Thus, it was postulated that, like GID2, GID1 is involved in the degradation of SLR1, or that GID1 functions upstream of SLR1 in GA signaling. A precise comparison of phenotypes between gid1 and other GA-related mutants revealed that the gid1 phenotype was more similar to those of severe alleles of GA-deficient mutants, such as cps (Sakamoto, T. et al., Plant Physiol. 134, 1642-1653 (2004)) and kao (Sakamoto, T. et al., Plant Physiol. 134, 1642-1653 (2004)), than to GA-insensitive mutants, such as gid2 (Sasaki, A. et al., Science 299, 1896-1898 (2003)) and ΔDELLA-type dominant GA-insensitive dwarf mutants (Itoh, H. et al., Plant Cell 14, 57-70 (2002)). Based on this phenotypic characteristic of gid1, it was predicted that GID1 was involved in GA perception. To verify this possibility, the interactions between GID1 and radioisotope-labeled GA was directly examined using non-equilibrium gel filtration (Nakajima, M. et al., Biochem. Biophys. Res. Comm. 241, 782-786 (1997)). As expected, GD1 exhibited binding activity to a tritiated $GA_4$ derivative ($3H_4$-16,17-dihydro-$GA_4$) and most of the binding was replaceable using an excess amount of non-labeled $GA_4$. The fact that binding was replaceable indicates that the binding is GA specific. In contrast, heat-denatured GID1, recombinant GID2, other members of the rice GA-signaling molecules did not exhibit any specific binding activity. Next, ligand specificity of GID1 was tested by using competition between the tritiated $GA_4$ derivative and various GAs. The concentration of each GA that is required for a 50% inhibition ($IC_{50}$) of the binding of the tritiated $GA_4$ derivative to GID1 is shown in Table 1. GD1 exhibited high affinity for biologically active GAs, such as $GA_4$, 16,17-dihydro-$GA_4$, $GA_1$, and $GA_3$, but showed no or almost no affinity for biologically inactive GAs. The $IC_{50}$ value for each of these GAs was well consistent with their physiological activity.

TABLE 1

Competition of various GAs in the binding of the $^3H$-$GA_4$ derivative to GID1 protein

|  | $IC_{50}$** | (Rel %) |
|---|---|---|
| $GA_4$ | $2 \times 10^{-7}$ M | (100) |
| $H_2$-$GA_4$ | $1 \times 10^{-6}$ M | (20) |
| $GA_1$ | $4 \times 10^{-6}$ M | (5) |
| $GA_3$ | $4 \times 10^{-6}$ M | (5) |
| $GA_{35}$ | $1 \times 10^{-5}$ M | (2) |
| $GA_{37}$ | $2 \times 10^{-5}$ M | (1) |
| $GA_4$-Me | $3 \times 10^{-5}$ M | (0.6) |
| $GA_9$ | $2 \times 10^{-4}$ M | (0.1) |
| $GA_{51}$ | $>2 \times 10^{-4}$ M | (<0.1) |
| 3-epi-$GA_4$ | $>2 \times 10^{-4}$ M | (<0.1) |

TABLE 1-continued

Competition of various GAs in the binding of the $^3$H-GA$_4$ derivative to GID1 protein IC$_{50}$** (Rel %)

[Structure: GA4]

[Structure: H$_2$-GA4]

[Structure: GA1]

[Structure: GA3]

[Structure: GA35]

[Structure: GA37]

TABLE 1-continued

Competition of various GAs in the binding of the $^3$H-GA$_4$ derivative to GID1 protein IC$_{50}$** (Rel %)

[Structure: GA4-Me]

[Structure: GA9]

[Structure: GA51]

[Structure: 3-epiGA4]

[Biologically active GAs (GA$_4$, 16,17-dihydro-GA$_4$, GA$_1$, and GA$_3$), GAs with weak activity (GA$_{35}$ and GA$_{37}$), and inactive GAs (GA$_4$ methyl ester, 3-epi-GA$_4$, GA$_9$, and GA$_{51}$) were tested.
**: IC$_{50}$ represents a concentration required for 50% inhibition.
Rel % represents a relative value (%)]

Figure 4:
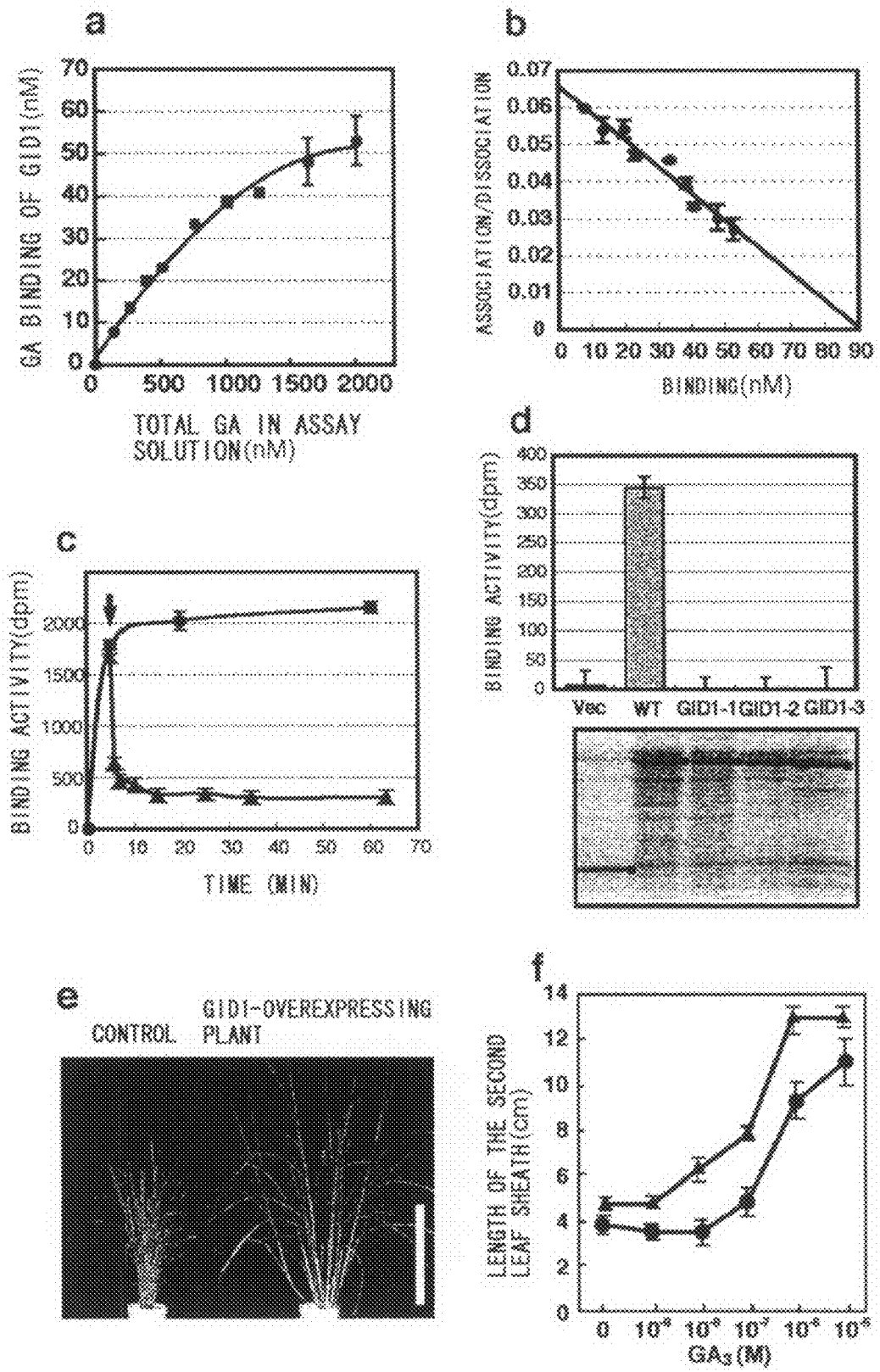
FIG. 4 demonstrates the GA-binding properties of GID1 and phenotypes of GID1-overproducing plants. Panel a) depicts the saturability for the GA binding of GID1. The recombinant GID1 was incubated with the tritiated $GA_4$ derivative $^3H_4$-16,17-dihydro$GA_4$ and with sequentially increased concentrations of non-labeled 16,17-dihydro$GA_4$. Bar represents the standard deviation (n=3). Panel b) depicts the results of a Scatchard plot for the data of binding shown in a. The $K_d$ value was calculated (correlation coefficient $R^2$=0.96) from t three independent experimental results. Panel c) depicts the $^3$H-GA association/dissociation rate to GID1. Total binding of $^3H_4$-16,17-dihydro$GA_4$ reached to half of the maximal value within several minutes (closed circle). When non-labeled $GA_4$ (0.125 mM) was added to the assay mixture (arrow), the $^3$H-GA binding was decreased to less than 10% within several minutes (closed triangle). Bar represents the standard deviation (n=3). Panel d) demonstrates that the mutant GID protein has lost the GA-binding activity. Upper panel, none of three recombinant proteins of mutant GID1s (GID1-1, 1-2, and 1-3) corresponding to the three gid1 alleles interacted with $GA_4$. The vector-derived tag protein (Vec) also did not interact. Bar represents the standard deviation (n=3). Bottom panel, Coomassie brilliant blue stain of the recombinant proteins used in this experiment. Dot represents GID or tag proteins in the SDS-PAGE profile. In this experiment, almost equal amounts of proteins were used for each (80 pmol). Panel e) depicts the gross morphologies of a GID1-overexpressing plant (Actin1 promoter-GID1, right) and wild type plant (control, left) three months after seeding. Bar=50 cm. f) dose-dependent GA response in the elongation of the second leaf sheath of GID1overexpressing plant (closed triangle) and wild type (closed circle). Bar represents the standard deviation (n=5).

Next, the kinetics of the binding of GID1 to GA was analyzed. To calculate the K$_d$ value of GID1 to GA, the saturability of GA binding was measured using various concentrations of GA$_4$ derivative (FIG. 4a). Scatchard plot analysis revealed that the K$_d$ values of 16,17-dihydro-GA$_4$ and GA$_4$ were $1.4 \times 10^{-6}$ M and $2.8 \times 10^{-7}$ M, respectively, based on the competition efficiencies of the two GAs (FIG. 4b and Table 1). These K$_d$ values can reasonably explain the cause for rice shoot elongation in response to an administered biologically active GA (FIG. 1c). Moreover, the association and dissociation rates for the binding were also examined. The half-time required for association/dissociation between GID1 and the GA$_4$ derivative was several minutes or less (FIG. 4c), indicating that these reactions occur very rapidly. This rapid kinetics of the GA binding is thought to be favorable for the functions as a cytoplasmic receptor. The GA binding activities of the mutant proteins derived from the three gid1 alleles, gid1-1, -2, and -3, which show a severe dwarf phenotype were then investigated. The mutant GID1 proteins had completely lost the binding activity to GA (FIG. 4d). This demonstrates that the single amino acid substitutions in GID1-1 and GID1-2 led to loss of the GA binding activity, and consequently, caused a complete GA insensitivity in rice plants. When these results are combined, it is concluded that GID1 meets the conventional criteria required for GA receptors (Kende, H. & Gardner, Annu. Rev. Plant, Physiol. 27, 267-290 (1976)), which are: (i) reversibility, (ii) high ligand specificity, (iii) reasonable affinity for biologically active ligands, and (iv) saturability of the GA binding characteristic.

Example 4

Transgenic Plants for Gibberellin Receptor Genes

If GID1 functions as a GA receptor, GID1-overexpressing plants are predicted to exhibit GA-hypersensitive phenotype. Thus, a transgenic rice plant that overexpresses GID1 under the control of the strong promoter of the rice actin gene was generated. The GID1-overexpressing plant exhibited tall plant height, long light-green leaf blades, reduced tillering number, and reduced mortality rate as compared to the wild-type. All these match the phenotypes obtained after excess GA administration (FIG. 4e). The GA responsiveness in the elongation of the second leaf sheath of the GID1-overexpressing plant was about 100 times higher as compared to the wild-type (FIG. 4f).

As described above, the $K_d$ value of GID1 to $GA_4$ is appropriate regarding the elongation of rice shoot. However, the value is about 10 times higher than those in GA-mediated responses in aleurone cells, such as α-amylase induction (FIG. 1c). It was postulated that the α-subunit of the trimeric G protein was involved in hypersensitive GA responses in aleurone cells (Ueguchi-Tanaka, M. et al., Proc. Natl. Acad. Sci. USA, 97, 11638-11643 (2000)). Specifically, there is the possibility that GA perception by GID1 is promoted in cooperation with a trimeric G protein-mediated membrane receptor system, and this may be functioning as another element of the GA receptor system in aleurone cells (Hooley, R. et al., Planta 183, 274-280 (1991); Jones, H. D. et al., Plant Cell 10, 245-254 (1998)).

GID1 encodes a previously unknown protein, and shares conserved sequences of the HSL family. HSL is a major enzyme in the hormonal regulation of lipolysis in adipocytes in mammals (Yeaman, S. J., Biochem J. 379, 11-22 (2004)). HSL hydrolyzes triglycerol upon receipt of signals from hormones such as noradrenalin and insulin. Although there is no genetic evidence in plants for receptor activity in vivo, Kumar and Klessig have reported that salicylic acid (SA)-binding protein 2 (SABP2) is a member of the HSL family having lipase activity and can interact with SA (Kumar, D. & Klessig, D. F., Proc. Natl. Acad. Sci. USA 100, 16101-16106 (2003)). The present invention has demonstrated that GID1 is a member of the HSL family involved in signal perception systems in plants and regulates GA signals by functioning as a cytoplasmic GA receptor.

Example 5

Identification of *Arabidopsis* Gibberellin Receptors

Multiple *Arabidopsis* genes encoding proteins similar to the amino acid sequence of rice GID1 (OsGID1) protein identified as described above were found through searches of gene sequence databases. FIG. 5 shows an alignment of the amino acid sequence of OsGID1 and deduced amino acid sequences encoded by ten *Arabidopsis* genes with high similarity to OsGID1. From two rice gid1 mutants (FIGS. 2b and 3a), two amino acid residues, Gly-196 and Arg-251, can be considered as being essential for GA interaction. Of the two, the Gly residue is present for all the genes listed in FIG. 5, while the Arg residue is present for only the top three genes. This suggested that these three candidates have GA binding activity similarly to OsGID1, but the rest do not.

Recombinant proteins were produced from the top seven genes exhibiting high similarity to OsGID1 using *E. coli*, and their GA binding activities were examined by nonequilibrium gel filtration using a tritiated $GA_4$ derivative, 16,17-dihydro-$GA_4$. Specifically, the coding region of the AtGID1 gene was amplified by PCR using specific primers designed based on the full-length cDNA sequence of the AtGID1 gene and having appropriate restriction sites at each end. After confirmation by sequence analysis, each cDNA fragment was ligated into pET32a vector (Novagen/Merck Biosciences, Madison, Wis., USA) or pGEX-4T-2 vector (Amersham Biosciences, Piscataway, N.J., USA; currently, a part of GE Healthcare). The production of recombinant proteins was confirmed by SDS-PAGE; vector cassettes were used as negative controls. GA binding assays were carried out similarly as described above using $[1,2,16,17-^3H_4]$-16,17-dihydro-$GA_4$ (4.55 TBq/mmol), which was custom-made by DuPont/NEN (Boston, Mass., USA). Non-labeled $GA_4$ (1.25 mM) was used to measure non-specific binding. Saturation experiments for the kinetic analysis were carried out using ten concentrations of 16,17-dihydro-$GA_4$ within the range of 25 to 1,500 nM. Competition assays were performed using $[1,2,16,17-^3H_4]$-16,17-dihydro-$GA_4$ at 15 nM and five concentrations of the non-labeled competitor. Recombinant RGA and GAI proteins were prepared using pET32a by a previously described method.

Figure 6:
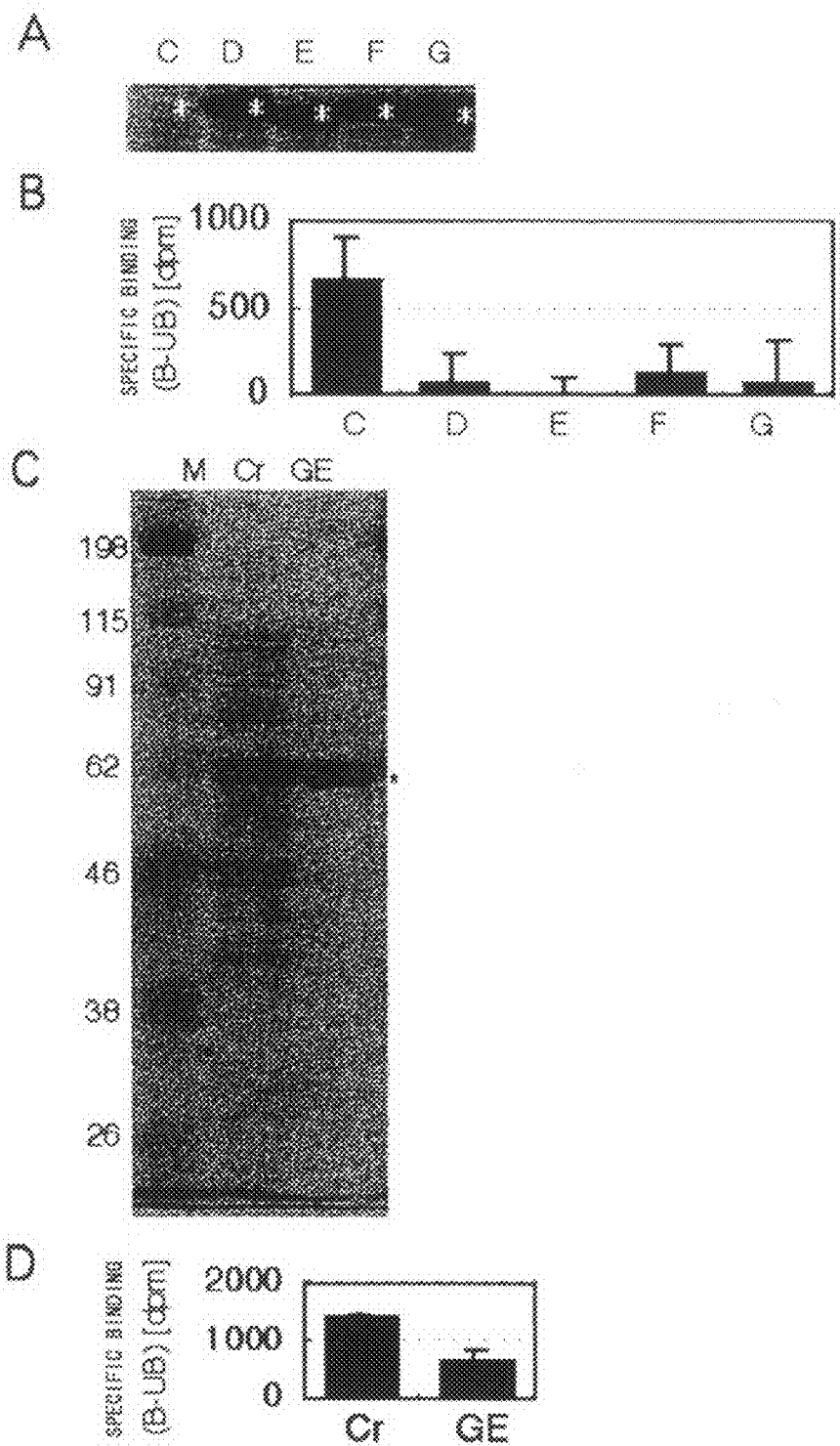
FIG. 6 relates to AtGID1-like proteins without GA-binding activity. Panel A) depicts recombinant proteins for each of the four AtGID1-like proteins (D, At5g23530; E, At5g06570; F, At5g62180; and G, At3g48700; each is shown using AGI code (The *Arabidopsis* Genome Initiative gene code)) was prepared using an *Escherichia coli* (*E. coli*) expression system. As compared to the amount of recombinant AtGID1c as a positive control (C), 10-fold amount of each crude protein was used in the subsequent GA-binding assay. Asterisks indicate recombinant proteins in SDS-PAGE. Panel B) depicts the GA-binding activities of AtGID1-like proteins (D to G) were assessed using standard protocols. The specific GA binding activity (B-UB) was calculated by subtracting the non-specific binding activity (UB: the activity indisplaceable by an excess amount of non-labeled GA) from the total binding activity (B). SD was determined from three independent measurements. Panel C) depicts the results of an SDS-PAGE profile of the crude fraction (Cr) of the recombinant AtGID1c protein and its purified fraction (GE) obtained by Ni column chromatography and gel filtration chromatography. Asterisk indicates the purified recombinant AtGID1c protein. Panel D) depicts the GA-binding activities of the crude fraction (Cr) and purified fraction (GE) of the recombinant AtGID1c protein. SD was determined from three independent measurements.

As predicted from the primary structure, products of the top three genes exhibited a reversible GA binding activity, however, the other four did not (FIG. 6). These three genes were named AtGID1a (At3g05120), AtGID1b (At3g63010), and AtGID1c (At5g27320). The amino acid sequences of these three AtGID1s revealed that these genes encode polypeptides with 345 amino acids (39 kDa, pI=6.6, AtGID1a), 358 amino acids (40 kDa, pI=7.4, AtGID1b), and 344 amino acids (38 kDa, pI=7.2, AtGID1c), respectively. The amino acid sequences of AtGID1s exhibit 67% to 85% identity to each other, and 60% to 63% identity to OsGID1.

Figure 7:
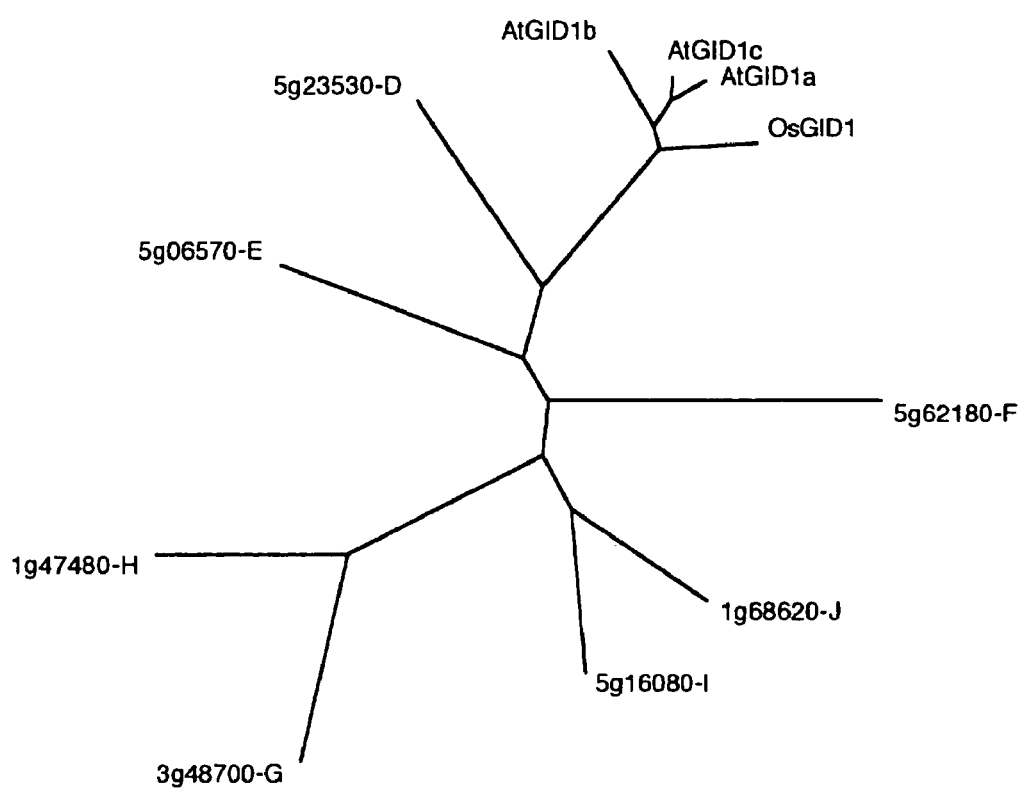
FIG. 7 depicts the results of the phylogenetic analysis of OsGID1 and 10 types of *Arabidopsis* proteins aligned by ClustalW program.

Phylogenetic analyses confirmed that the three AtGID1s are classified into the same group as OsGID1, and are classified in an independent group from the others (FIG. 7). Since AtGID1a and AtGID1c could be classified into a same subgroup while AtGID1b belonged to an independent subgroup, the phylogenetic tree suggested that the biological functions of AtGID1b were different from those of the other AtGID1s.

Example 6

GA Binding Properties of *Arabidopsis* GID1

Figure 8:
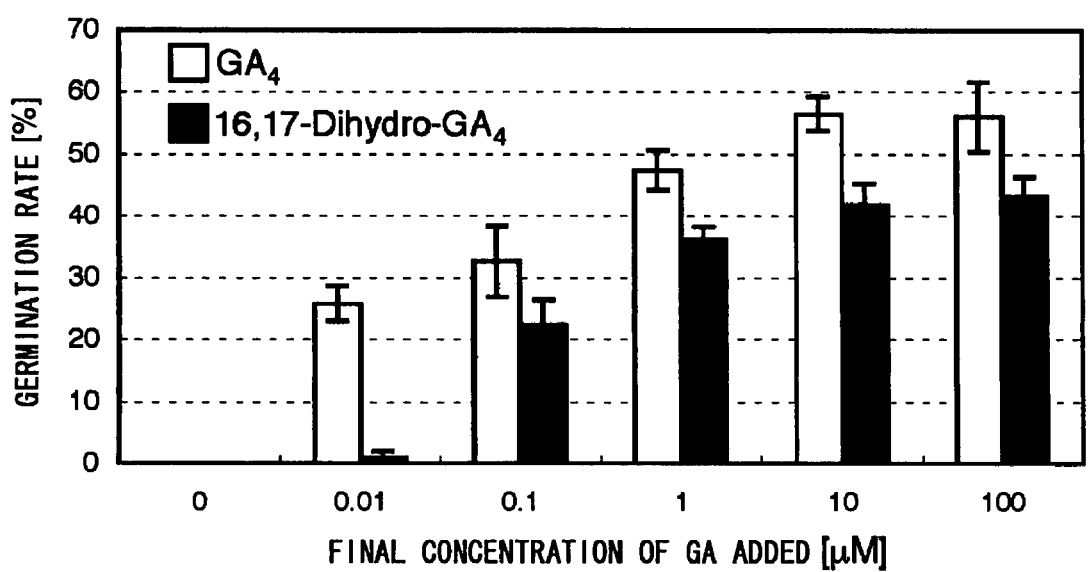
FIG. 8 demonstrates the physiological activity of 16,17-dihydro-$GA_4$ in *Arabidopsis* seeds. The germination of GA-deficient ga1-3 seeds in a medium containing 16,17-dihydro- GA$_4$ was tested, according to the method of Yamaguchi et al. (Plant Cell, 10, 2115-2126, 1988). Approximately 70 to 80 seeds were used per each dish. Three independent measurements were carried, and the standard deviation (SD) was determined from these measurements. The seeds were assessed for germination at 23° C. on day 4, after cold treatment at 4° C. for 3 days. GA$_4$ was used as a reference.
Figure 9:
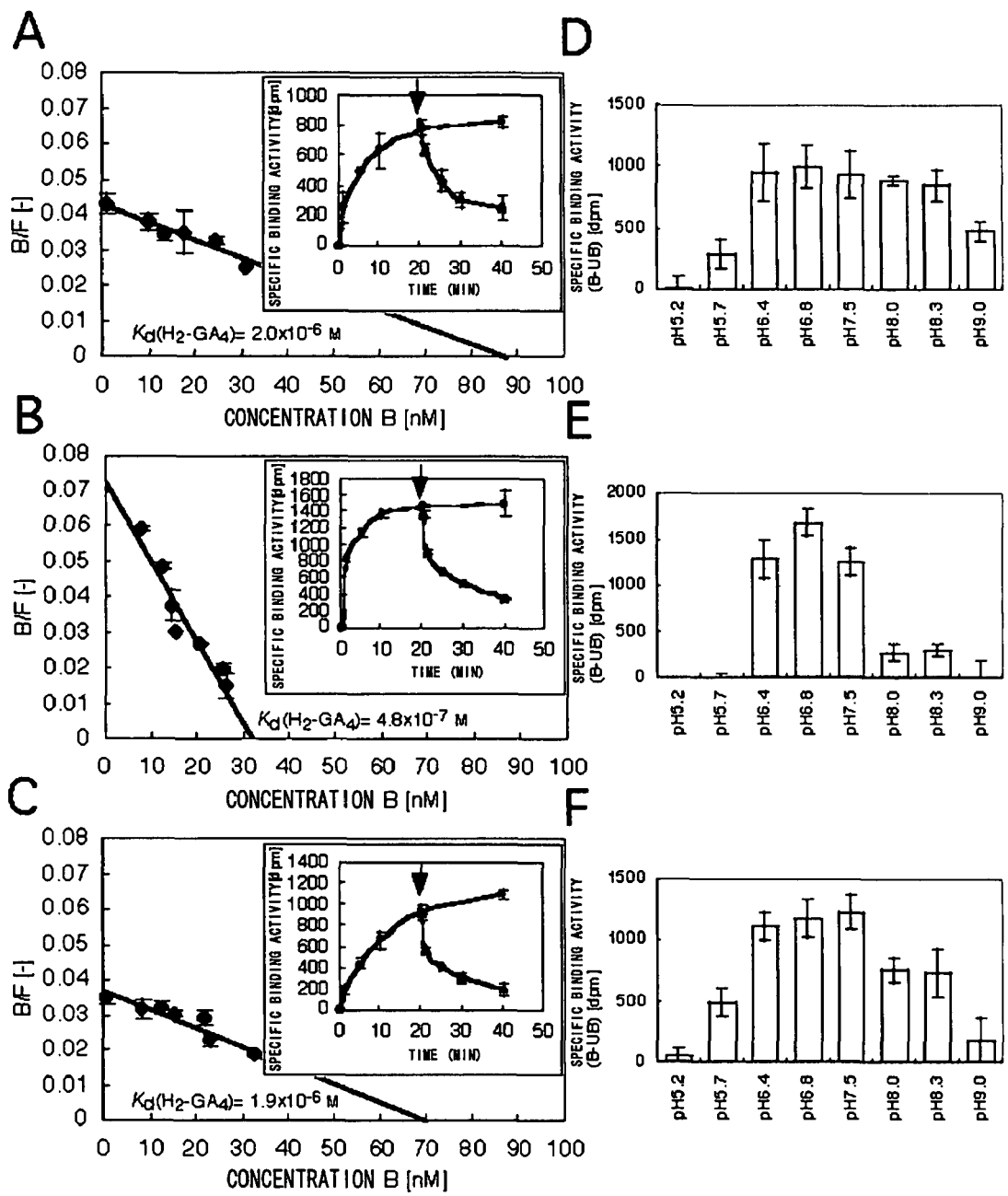
FIG. 9 demonstrates the GA-binding property of AtGID1. Panels A) to C) depict the results of Scatchard plot analyses for the GA binding of AtGID1. Results for AtGID1a (A), AtGID1b (B), and AtGID1c (C) are shown. The K$_d$ values for 16,17-dihydro-GA$_4$ was determined by adding various concentrations of GA to the assay mixture. Standard deviation (SD) was determined from these three independent measurements. The insets show time-course characteristics for the GA binding of AtGID1 and replacement (arrow) using an excess amount of non-labeled GA$_4$ (0.125 mM). Panels D) to F) depict the GA binding activities of AtGID1 under different pH conditions. Results for AtGID1a (D), AtGID1b (E), and AtGID1c (F) are shown. The non-specific binding activity (UB) was determined by adding 0.125 mM GA$_4$ to the assay solution, and this was subtracted from the total binding activity (B) to determine the specific binding activity (B-UB).

The kinetics, ligand selectivity, and pH dependence of GA binding for the three AtGID1s identified as described above were examined using the tritiated $GA_4$ derivative 16,17-dihydro-$GA_4$. There are two chemical isoforms of 16,17-dihydro-$GA_4$, depending on the position of C-16; however, both isoforms could equally bind to AtGID1s. 16,17-dihydro-$GA_4$ had a physiological effect of about ¹⁄₁₀ of that of $GA_4$ on the germination of the GA-deficient *Arabidopsis* mutant ga1-3 (FIG. 8). First, the characteristics over time of the association of tritiated 16,17-dihydro-$GA_4$ and each AtGID1 after addition of an excess amount of non-labeled $GA_4$ were investigated by variously changing the incubation time and dissociation time. As shown in the insets of FIG. 9A to C, the dissociation of GA from the AtGID1a complex was slower than that from AtGID1b complex, while the association of AtGID1b with GA was more rapid than that of AtGID1a. In contrast, the association of AtGID1c with GA was slower than that of AtGID1b; however, there was no clear difference between the dissociation of GA from the AtGID1c complex and from the AtGID1b complexes. Furthermore, the kinetics of GA binding of each AtGID1 was analyzed under equilibrium conditions of GA at various concentrations. As a result, the affinity of AtGID1b to 16,17-dihydro-$GA_4$ ($K=4.8\times10^{-7}$ M) was revealed to be four times higher than those of AtGID1a ($K_d=2.0\times10^{-6}$ M) and AtGID1c ($K_d=0.9\times10^{-6}$ M) (FIGS. 9A to 9c).

The ligand selectivity of each AtGID1 was examined by observing the competitive inhibition, by the addition of GA to the assay mixtures, of the binding between the recombinant proteins and tritiated 16,17-dihydro-$GA_4$ (Table 2). The structure of each GA examined in this assay is shown in Table 1. The ligand selectivity was evaluated using the concentration of GA that inhibits 50% of the tracer (15 nM) binding ($IC_{50}$ value). All AtGID1s showed very similar ligand selectivity. Among the GAs tested, $GA_4$ had the strongest inhibitory effect, and $GA_3$ and $GA_1$, which are also classified into active GAs, had a intermediate effect. Meanwhile, physiologically inactive GAs had no effect, suggesting that they do not interact with AtGID1s.

TABLE 2

Competitive ability of GA in AtGID1-GA binding

|  | AtGID1a | AtGID1b | AtGID1c |
| --- | --- | --- | --- |
| $GA_4$ | $3\times10^{-7}$ (100) | $3\times10^{-8}$ (100) | $3\times10^{-7}$ (100) |
| $H_2$-$GA_4$ | $4\times10^{-6}$ (8) | $4\times10^{-7}$ (8) | $5\times10^{-6}$ (6) |
| $GA_3$ | $3\times10^{-5}$ (1) | $2\times10^{-6}$ (2) | $3\times10^{-5}$ (1) |
| $GA_1$ | $3\times10^{-5}$ (1) | $4\times10^{-6}$ (1) | $3\times10^{-5}$ (1) |
| $GA_{35}$ | $3\times10^{-5}$ (1) | $4\times10^{-6}$ (1) | $5\times10^{-5}$ (0.6) |
| $GA_{37}$ | $7\times10^{-5}$ (0.4) | $9\times10^{-6}$ (0.3) | $8\times10^{-5}$ (0.4) |
| $GA_4$-Me | $3\times10^{-4}$ (0.1) | $9\times10^{-6}$ (0.3) | $9\times10^{-5}$ (0.3) |
| $GA_9$ | $>3\times10^{-4}$ (<0.1) | $9\times10^{-5}$ (<0.1) | $>3\times10^{-4}$ (<0.1) |
| $GA_{51}$ | $>3\times10^{-4}$ (<0.1) | $4\times10^{-5}$ (<0.1) | $>3\times10^{-4}$ (<0.1) |
| 3-epi-$GA_4$ | $>3\times10^{-4}$ (<0.1) | $1\times10^{-4}$ (<0.1) | $>3\times10^{-4}$ (<0.1) |

[$IC_{50}$ value (M) was used to evaluate the effect of each GA. Each value indicates a mean of at least two measurements. The relative values for each GA, taking the value for $GA_4$ as 100 (%), are shown in parenthesis. $H_2$-$GA_4$: 16,17-dihydro-$GA_4$; $GA_4$-Me: methyl ester of $GA_4$]

The pI value of AtGID1a predicted from the amino acid sequence is clearly lower than the values of the other two. Thus, the effect of the pH on GA binding was investigated for each AtGID1. While all AtGID1s exhibited the strongest GA binding activity under a neutral pH environment, their behaviors for GA binding were different under other pH conditions. While AtGID1b exhibited the strongest pH dependence, AtGID1a and AtGID1c were more permissive to pH conditions other than neutral pH (the optimal pH range for GA binding for AtGID1b was 6.4 to 7.5; that for AtGID1a was 6.4 to 9.0; and that for AtGID1c was 5.7 to 8.3; FIGS. 9D to 9F). These biochemical experiments demonstrated that all three AtGID1s have reasonable GA-binding activity, and that the property of AtGID1b is different from those of the other two in terms of GA binding affinity and pH dependence.

Example 7

In Vivo and In Vitro AtGID1-AtDELLA Interaction

Arabidopsis has five DELLA proteins (RGA, GAI, RGL1, RGL2, and RGL3; collectively designated AtDELLA; Fleet, C. M., and Sun, T.-P. (2005) Curr. Opin. Plant Biol., 8, 77-85; Dill, A., and Sun, T. (2001) Genetics, 159, 777-785); therefore, there are 15 possible combinations of GID1/DELLA proteins. To verify the positive interactions between AtGID1-AtDELLA, two experiments were conducted using the yeast two hybrid (Y2H) system. In the first experiment (Assay A), a viable colony assay using a defined medium in which only positive clones would survive was carried out. In the second experiment (Assay B), β-galactosidase activity was measured, as reporter gene product of AtGID1-AtDELLA interactions.

BD Matchmaker Two-hybrid System 3 (Clontech, Palo Alto, Calif., USA; now part of Takara Bio) was used in the Y2H experiments. After confirming the PCR products of the AtGID1 genes by sequencing, PCR products were cloned into pGBKT7 DNA-BD shuttle vector to construct bait plasmids. Likewise, the entire coding region of each AtDELLA gene (GAI including EcoRI and XhoI sites; RGA including BamHI and XhoI sites; RGL1 including SmaI and SacI sites; RGL2 including SmaI and ClaI sites; RGL3 including SmaI and XhoI sites on the ends) was cloned into pGADT7 AD vector. The S. cerevisiae AH109 (MATa) strain or Y187 (MATα) strain was used, and DNA-BD and AD vector cassettes were used as negative controls. The details of the method used for the yeast assay are as described in the manufacturer's instructions (Yeast Protocols Handbook #PT3024-1). Experiments were carried out four times independently. Similar results were obtained each time.

Figure 10:
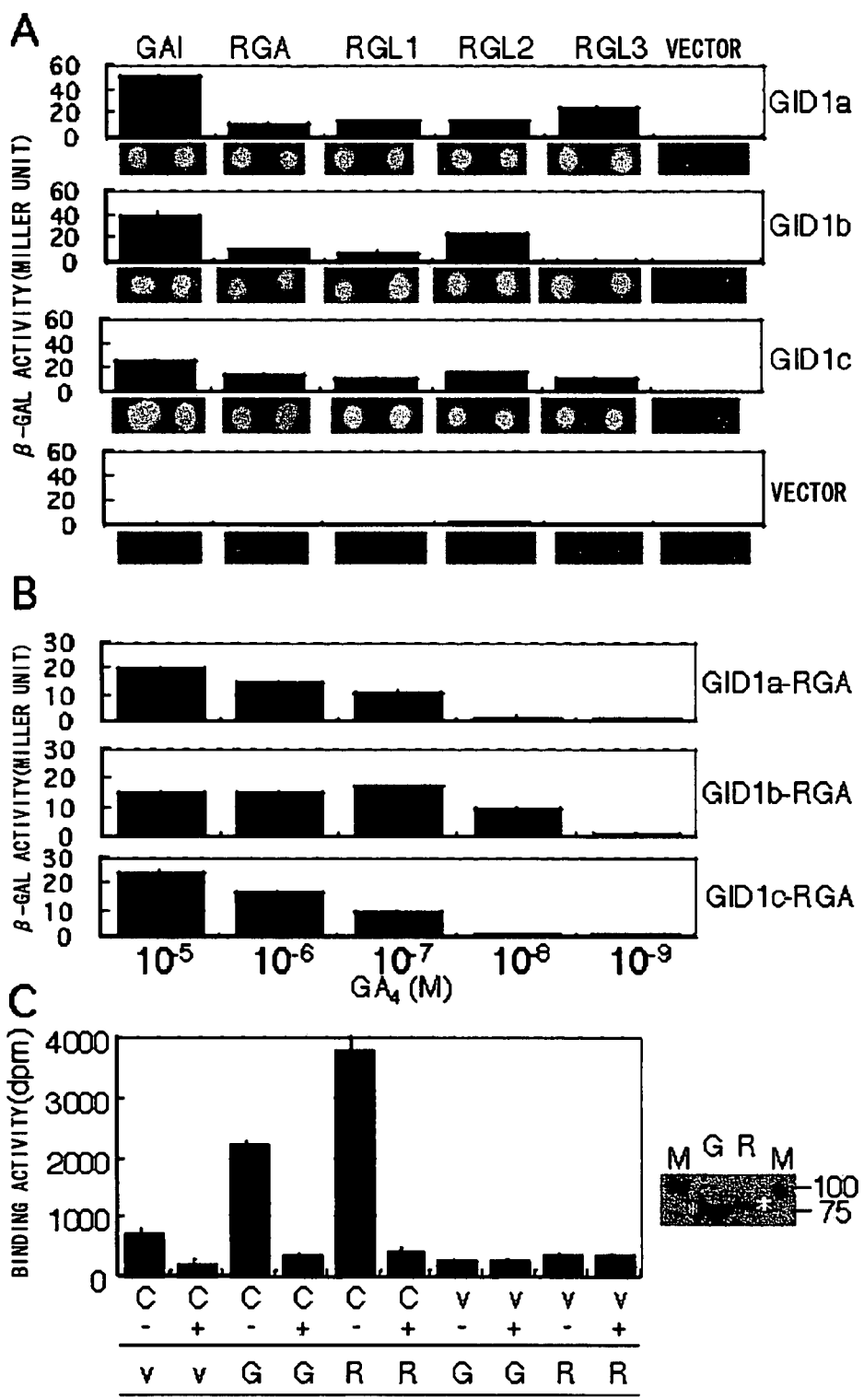
FIG. 10 demonstrates the in vivo and in vitro AtGID1-AtDELLA interaction. Panel A) depicts AtGID1-AtDELLA interaction in the presence of GA in two types of yeast hybrid (Y2H) assays. Each AtGID1 was used as a bait while AtDELLA was a prey. GA$_4$ ($10^{-5}$ M) was added to the medium. The bars indicates β-galactosidase activity when o-nitrophenol-β-D-galactopyranoside was used as a substrate (Assay B). The growth of each transformant in the defined medium for 2 days (Assay A) is shown beneath of each bar graph. The experiment was carried out in quadruplicate. The SD value shown in the figure was determined from three measurements. Panel B) depicts the dose response in AtGID1-RGA interaction in Assay B of Y2H. GA$_4$ ($10^{-5}$ to $10^{-9}$ M) was added to the medium. The experiment was conducted in duplicates. The SD value shown in the figure was determined from three measurements. Panel C) depicts the results of an evaluation of the in vitro GA-binding potency of AtGID1 using AtDELLA. Left panel, 15 minutes after mixing AtGID1c (C), tritiated GA, with an excess amount of non-labeled GA (+) or without non-labeled GA (-). GAI (G) or RGA (R) was added, and then the GA-binding activity in each reaction mixture was measured according to the standard method. Recombinant protein originating from the vector (v) was used as a negative control. The experiment was carried out in duplicates. The SD value was determined from three measurements. Right panel, a profile of Western blotting for recombinant AtDELLA using an antibody to His tag. G, GAI; R, RGA; v, vector; M, molecular weight marker.
Figure 11:
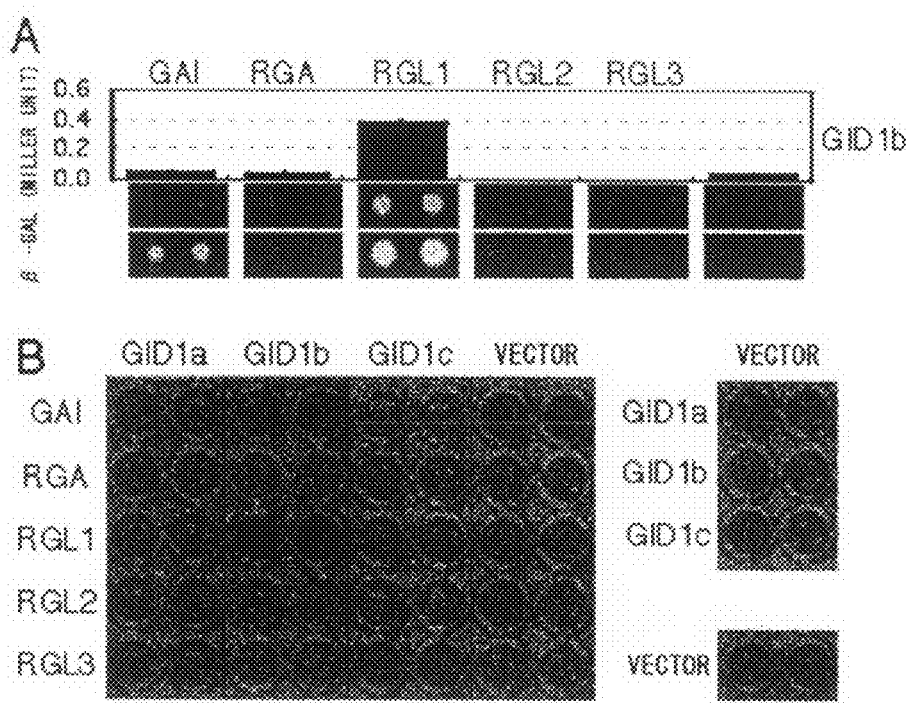
FIG. 11 demonstrates GA-independent AtGID1b-AtDELLA interaction. Panel A) depicts the detection of positive signals for AtGID1b-RGL1 in both assays in the absence of GA. Bottom panel, growth of each transformant in Assay A. The transformant for AtGID1b-GAI also formed colonies after 4 days of prolonged incubation. Upper panel, β-galactosidase activity of each transformant in Assay B. When o-nitrophenol-β-D-galactopyranoside was used, the signals were not detected. The positive signals were detected only when chlorophenol red-β-D-galactopyranoside, a highly sensitive substrate, was used. Panel B) depicts the profile of Assay B when a highly sensitive substrate, chlorophenol red-β-D-galactopyranoside, was used, and then o-nitrophenol-β-D-galactopyranoside was used. Absorbance in each well was measured at 570 nm.

$GA_4$ exhibited the strongest affinity for all AtGID1s in the GA binding assay (Table 2). Thus, $GA_4$ ($10^{-5}$ M) was used and added to the medium. As shown in FIG. 10A, in Assay A, yeast transformants formed colonies in the presence of GA for all AtGID1-AtDELLA pairs, while no colonies were formed in the cases of the other negative controls. β-galactosidase activity was detected for all the 15 pairs in Assay B as well. As described above, all AtGID1-AtDELLA interactions were detected in a GA-dependent manner; however, interactions between AtGID1b and some AtDELLAs were detected, albeit weakly, in the absence of GA (FIG. 11). These observations suggest that interactions between AtGID1 and AtDELLA occur in planta in a GA-dependent manner, but that AtGID1b-RGL1 interactions may occur in a GA-independent manner.

As shown in FIG. 10A, the level of enzymatic activity of β-galactosidase in the AtGID1-RGA pair was relatively intermediate and thus is suitable for comparison purposes; therefore, the dose response of the AtGID1-RGA interaction to various concentrations of $GA_4$ was tested by Assay B. AtGID1a-RGA and AtGID1c-RGA interactions were detected only in the presence of $GA_4$ above $10^{-7}$ M, while AtGID1b could interact with RGA even when $GA_4$ was present at $10^{-8}$ M (FIG. 10B).

As described above, by using the Y2H system, all AtGID1s were demonstrated to clearly interact with AtDELLA proteins. Next, whether AtDELLAs exert some kind of influence on the GA-binding activity of AtGID1s was examined in vitro. After labeled 16,17-dihydro-$GA_4$ and AtGID1s were combined, AtDELLAs were added to the solutions, and the GA-binding activity was measured. FIG. 10C clearly shows that the binding activity of AtGID1s increased after addition of AtDELLAs. The in vitro effect of AtDELLAs appeared to be independent of the type of DELLA, and RGA and GAI both showed a similar effect on GA-binding of AtGID1c (FIG. 10C). In addition, the binding affinity of AtGID1c-GA interaction after addition of DELLA proteins to the reaction mixture was examined. The Scatchard plot shows that the $K_d$ value for the binding between AtGID1c and 16,17-dihydro-$GA_4$ in the presence of RGA is $1.2 \times 10^{-8}$ M, while the value in the presence of GAI is $4.6 \times 10^{-8}$ M; thus, the values are reduced to about 1/100 as compared with the value in the absence of AtDELLA ($K_d = 1.9 \times 10^{-6}$ M; shown in FIG. 9C). Hence, AtGID1-GA binding is enhanced in the presence of AtDELLAs.

Example 8

Complementary Effect of AtGID1s on the Phenotype of Rice gid1-1

To prove that AtGID1s have the same functions as rice GID1 (OsGID1) in vivo, transformants overexpressing each AtGID1 gene under the control of the constitutive promoter of Act1 were produced with the rice gid1-1 background. Specifically, the full-length cDNAs for AtGID1s, including appropriate restriction sites at each end (SmaI site for AtGID1a/c; XbaI and SmaI sites for AtGID1b) were prepared by PCR, and inserted into a binary vector carrying the rice actin promoter (pAct1) and NOS terminator (Sentoku, N. et al. (2000) Develop. Biol., 220, 358-364). After confirmation of the insertion, pAct1-AtGID1 fragments were introduced into rice gid1-1 plants through *Agrobacterium*-mediated transformation.

Eight lines each were obtained for AtGID1a and AtGID1b, and 14 lines were obtained for AtGID1c. The gid1-1 dwarf phenotype was rescued in all transgenic plants carrying an AtGID1 clone (FIG. 12A). This suggests that AtGID1s functioned as GA receptors in rice. The height of AtGID1a plants was slightly lower than that of the other transgenic plants and wild-type plants (FIG. 12A). This trend was seen in almost all AtGID1a plants. The expression level of AtGID1a mRNAs in these transgenic plants was the same as that in the other AtGID1s (FIG. 12B). Thus, the GA receptor function of AtGID1a can be considered to be weaker than those of AtGID1b and AtGID1c, at least in rice cells. Furthermore, the GA response in these transformants carrying AtGID1s was further tested by exogenously treating with $GA_3$. In this experiment, a tillering plant of each line was divided into two seedling plants. $GA_3$ was given to one seedling plant once a day for five days, while a mock solution not including $GA_3$ was given to the other. These plants were confirmed to normally respond to the added GA, similarly to the response of the wild-type plant. Very similar results were obtained from two independent experiments.

Example 9

Expression of AtGID1s in Various Organs

The expression of the AtGID1 genes in various organs of *Arabidopsis*, specifically, in stems, flowers, siliques, leaves, roots, and imbibed seeds of plants of about 10-cm height (40 to 45 days after germination) was analyzed by semi-quantitative RT-PCR. Total RNA preparation and RT-PCR were carried out according to Kim et al. (Kim, Y.-C. et al. (2005) Plant Cell Physiol., 46, 1317-1325) using the specific primers listed in Table 3. The specificity of the primers to the above-described expression vectors has been confirmed. The appropriate number of PCR cycles was determined for each gene by trial experiments, using different numbers of PCR cycles at intervals of two cycles, so that the amount of each visualized product was within a certain dynamic range. Experiments were carried out independently at least twice. Similar results were obtained each time.

TABLE 3

Primers used in RT-PCR

| | | |
|---|---|---|
| AtGID1a, Fwd; | 5'-CAGATCAAGAGCAACCTCCTAG-3' | (SEQ ID NO: 17) |
| AtGID1a, Rev; | 5'-CCACAGGCAATACATTCACCTGTGTG-3' | (SEQ ID NO: 18) |
| AtGID1b, Fwd; | 5'-GAACCCTCGAGCTAACCAAACCTCTC-3' | (SEQ ID NO: 19) |
| AtGID1b, Rev; | 5'-GGAGTAAGAAGCACAGGACTTGACTTGC-3' | (SEQ ID NO: 20) |
| AtGID1c, Fwd; | 5'-CTGGCACTTCACCAAGTATTACTG-3' | (SEQ ID NO: 21) |
| AtGID1c, Rev; | 5'-GCCAATAGTGGCTTGCTCCAAG-3' | (SEQ ID NO: 22) |
| OsActin, Fwd; | 5'-TCCATCTTGGCATCTCTCAG-3' | (SEQ ID NO: 23) |
| OsActin, Rev; | 5'-GTACCCTCATCAGGCATCTG-3' | (SEQ ID NO: 24) |
| AtActin, Fwd; | 5'-CGTGTGTGACAATGGTACCGGTATGG-3' | (SEQ ID NO: 25) |
| AtActin, Rev; | 5'-CTGTGAACGATTCCTGGACCTGCCTC-3' | (SEQ ID NO: 26) |

(Fwd: forward primer; Rev: reverse primer)

As shown in FIG. 12C, the expression of the AtGID1 genes could be detected in various organs. This result was also supported by open access array databases such as NASCArrays (Craigon D J et al., Nucleic Acids Res. 32:D575-7, 2004) and Gene Atlas (Zimmermann P et al., Plant Physiol. 136: 2621-2632, 2004). This indicates that the three AtGID1s function in various organs of *Arabidopsis*.

INDUSTRIAL APPLICABILITY

The present invention provides gibberellin-binding proteins that mediate gibberellin response signals, and the genes encoding same. Plant differentiation and growth can be regulated by controlling the expression of the proteins of the present invention. For example, the growth rate can be increased by increasing the expression of the proteins of the present invention; conversely, by reducing the expression of the proteins of the present invention, plant height can be shortened and their lodging tolerance can be improved. The present invention is therefore useful in increasing the yield of crops and in generating ornamental plants with new aesthetic values.

The invention claimed is:

1. A method for binding a protein with gibberellin, which comprises the step of contacting the protein with gibberellin, wherein the protein is selected from the group consisting of:
   (i) a protein comprising the amino acid sequence of SEQ ID NO: 2,
   (ii) a protein comprising an amino acid sequence having 95% or higher identity to SEQ ID NO: 2 and has the activity of binding to gibberellin, and
   (iii) a protein having the activity of binding to gibberellin and is encoded by a nucleic acid that hybridizes to the complement of SEQ ID NO:1 at 65° C. in a solution containing 5×SSC, 7% (W/V) SDS, 100 µg/ml denatured salmon sperm DNA, 5×Denhardt's solution, followed by washing in 0.1×SSC at 65° C.

2. A method for detecting gibberellin binding, which comprises the steps of contacting a protein with gibberellin and detecting the binding between the protein and gibberellin, wherein the protein is selected from the group consisting of:
   (i) a protein comprising the amino acid sequence of SEQ ID NO: 2,
   (ii) a protein comprising an amino acid sequence having 95% or higher identity to SEQ ID NO: 2 and has the activity of binding to gibberellin, and
   (iii) a protein having the activity of binding to gibberellin and is encoded by a nucleic acid that hybridizes to the complement of SEQ ID NO:1 at 65° C. in a solution containing 5×SSC, 7% (W/V) SDS, 100 µg/ml denatured salmon sperm DNA, 5×Denhardt's solution, followed by washing in 0.1×SSC at 65° C.

3. A method for assaying a compound that regulates the interaction between gibberellin and a protein, which comprises the steps of:
   (a) contacting a test compound, gibberellin, and the protein; and
   (b) detecting the binding between gibberellin and the protein, wherein the protein is selected from the group consisting of:
   (i) a protein comprising the amino acid sequence of SEQ ID NO: 2,
   (ii) a protein comprising an amino acid sequence having 95% or higher identity to SEQ ID NO: 2 and has the activity of binding to gibberellin, and
   (iii) a protein having the activity of binding to gibberellin and is encoded by a nucleic acid that hybridizes to the complement of SEQ ID NO:1 at 65° C. in a solution containing 5×SSC, 7% (W/V) SDS, 100 µg/ml denatured salmon sperm DNA, 5×Denhardt's solution, followed by washing in 0.1×SSC at 65° C.

4. A method for selecting a compound that inhibits the interaction between gibberellin and a protein, which comprises the steps of:
   (a) contacting a test compound, gibberellin, and the protein;
   (b) detecting the binding between gibberellin and the protein; and
   (c) selecting a compound that inhibits the binding, wherein the protein is selected from the group consisting of:
   (i) a protein comprising the amino acid sequence of SEQ ID NO: 2,
   (ii) a protein comprising an amino acid sequence having 95% or higher identity to SEQ ID NO: 2 and has the activity of binding to gibberellin, and
   (iii) a protein having the activity of binding to gibberellin and is encoded by a nucleic acid that hybridizes to the complement of SEQ ID NO:1 at 65° C. in a solution containing 5×SSC, 7% (W/V) SDS, 100 µg/ml denatured salmon sperm DNA, 5×Denhardt's solution, followed by washing in 0.1×SSC at 65° C.

5. A method for binding a first protein with a DELLA protein, which comprises the step of contacting the proteins, wherein the first protein is selected from the group consisting of:
   (i) a protein comprising the amino acid sequence of SEQ ID NO: 2,
   (ii) a protein comprising an amino acid sequence having 95% or higher identity to SEQ ID NO: 2 and has the activity of binding to the DELLA protein, and
   (iii) a protein having the activity of binding to the DELLA protein and is encoded by a nucleic acid that hybridizes to the complement of SEQ ID NO:1 at 65° C. in a solution containing 5×SSC, 7% (W/V) SDS, 100 µg/ml denatured salmon sperm DNA, 5×Denhardt's solution, followed by washing in 0.1×SSC at 65° C.

6. An isolated and purified complex comprising gibberellin and a protein selected from the group consisting of:
   (i) a protein comprising the amino acid sequence of SEQ ID NO: 2,
   (ii) a protein comprising an amino acid sequence having 95% or higher identity to SEQ ID NO: 2 and has the activity of binding to gibberellin, and
   (iii) a protein having the activity of binding to gibberellin and is encoded by a nucleic acid that hybridizes to the complement of SEQ ID NO:1 at 65° C. in a solution containing 5×SSC, 7% (W/V) SDS, 100 µg/ml denatured salmon sperm DNA, 5×Denhardt's solution, followed by washing in 0.1×SSC at 65° C.

7. The complex of claim 6, which further comprises a DELLA protein.

8. An isolated and purified complex comprising a DELLA protein and a protein which selected from the group consisting of:
   (i) a protein comprising the amino acid sequence of SEQ ID NO: 2,
   (ii) a protein comprising an amino acid sequence having 95% or higher identity to SEQ ID NO: 2 and has the activity of binding to the DELLA protein, or
   (iii) a protein having the activity of binding to the DELLA protein and is encoded by a nucleic acid that hybridizes to the complement of SEQ ID NO:1 at 65° C. in a solution containing 5×SSC, 7% (W/V) SDS, 100 µg/ml denatured salmon sperm DNA, 5×Denhardt's solution, followed by washing in 0.1×SSC at 65° C.

* * * * *

UNITED STATES PATENT AND TRADEMARK OFFICE
CERTIFICATE OF CORRECTION

| | | |
|---|---|---|
| PATENT NO. | : 7,915,050 B2 | Page 1 of 1 |
| APPLICATION NO. | : 11/918378 | |
| DATED | : March 29, 2011 | |
| INVENTOR(S) | : Matsuoka et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 518 days.

Signed and Sealed this
Twenty-third Day of August, 2011

David J. Kappos
*Director of the United States Patent and Trademark Office*